US005792073A

United States Patent [19]
Keefe

[11] Patent Number: 5,792,073
[45] Date of Patent: Aug. 11, 1998

[54] SYSTEM AND METHOD FOR ACOUSTIC RESPONSE MEASUREMENT IN THE EAR CANAL

[75] Inventor: Douglas H. Keefe, Omaha, Nebr.

[73] Assignee: Boys Town National Research Hospital, Omaha, Nebr.

[21] Appl. No.: 732,642

[22] Filed: Oct. 1, 1996

Related U.S. Application Data

[63] Continuation-in-part of Ser. No. 599,467, Jan. 23, 1996.

[51] Int. Cl.$^6$ ........................................... A61B 5/12
[52] U.S. Cl. ........................................... 600/559; 73/585
[58] Field of Search ........................... 128/848, 897–898; 73/585; 600/552, 559

[56] References Cited

U.S. PATENT DOCUMENTS

| | | | |
|---|---|---|---|
| 4,374,526 | 2/1983 | Kemp | 128/746 |
| 4,884,447 | 12/1989 | Kemp | 73/585 |
| 5,372,142 | 12/1994 | Madsen et al. | 128/739 |
| 5,526,819 | 6/1996 | Lonsbury-Martin et al. | 128/746 |
| 5,594,174 | 1/1997 | Keefe | 73/585 |
| 5,651,371 | 7/1997 | Keefe | 128/746 |
| 5,664,577 | 9/1997 | Lonsbury-Martin et al. | 128/746 |

OTHER PUBLICATIONS

Ann Brown Modulation of the Hair Cell Motor: A Possible Souce of Odd–Order Distortion, J. Acoust. Soc. Am., vol. 96, pp. 2210–2215, 1994.

Primary Examiner—Francis Jaworski
Attorney, Agent, or Firm—Henderson & Sturm

[57] ABSTRACT

A system and method for measurement of acoustic response, such as occurs in the ear canal when double-evoked otoacoustic emission signals elicit an evoked response from the cochlea. A three sample stimulus includes a first signal, a time delayed second signal and the useful superposition of the first and second signals. The time delay is less than the maximum latency of the cochlear emission. Each signal elicits a cochlear response that includes a linear response, which is eliminated by subtracting the first and second individual signal responses from the response to the useful superposition signal. One class of signals arises when the time delayed signal is a scaled version of the first signal. The signals may be presented using a single acoustic source or separate acoustic sources. Appropriate selection of time delays greatly reduces nonlinear response due to probe distortion. Using two acoustic sources, probe distortion can be virtually eliminated. The invention also includes a noise coherence measurement to determine the relative levels of system response caused by random noise and nonlinear response. Real-time artifact rejection techniques simplify data collection.

101 Claims, 12 Drawing Sheets

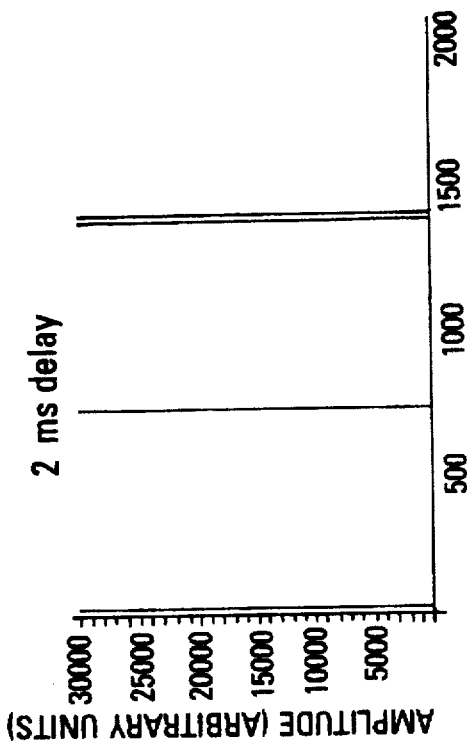
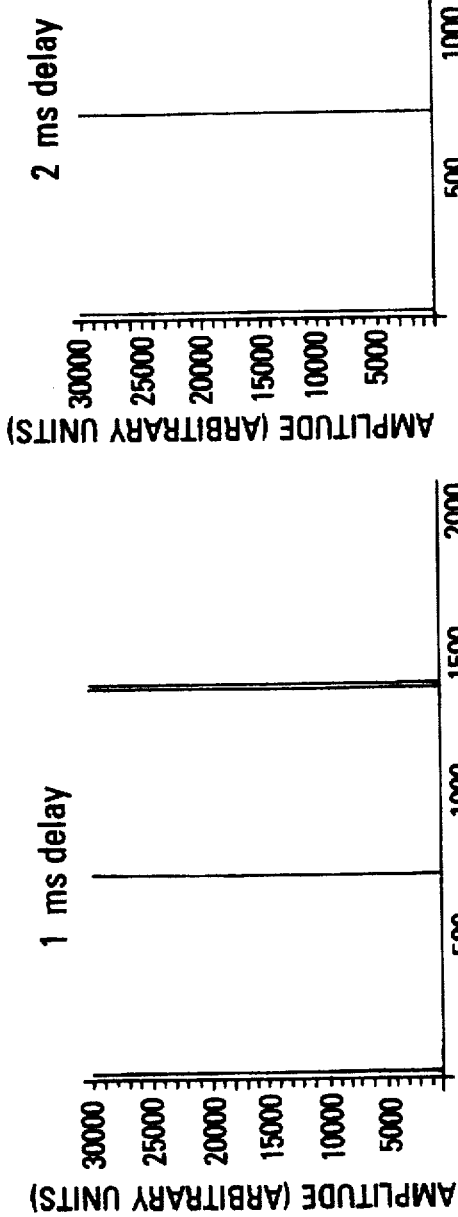
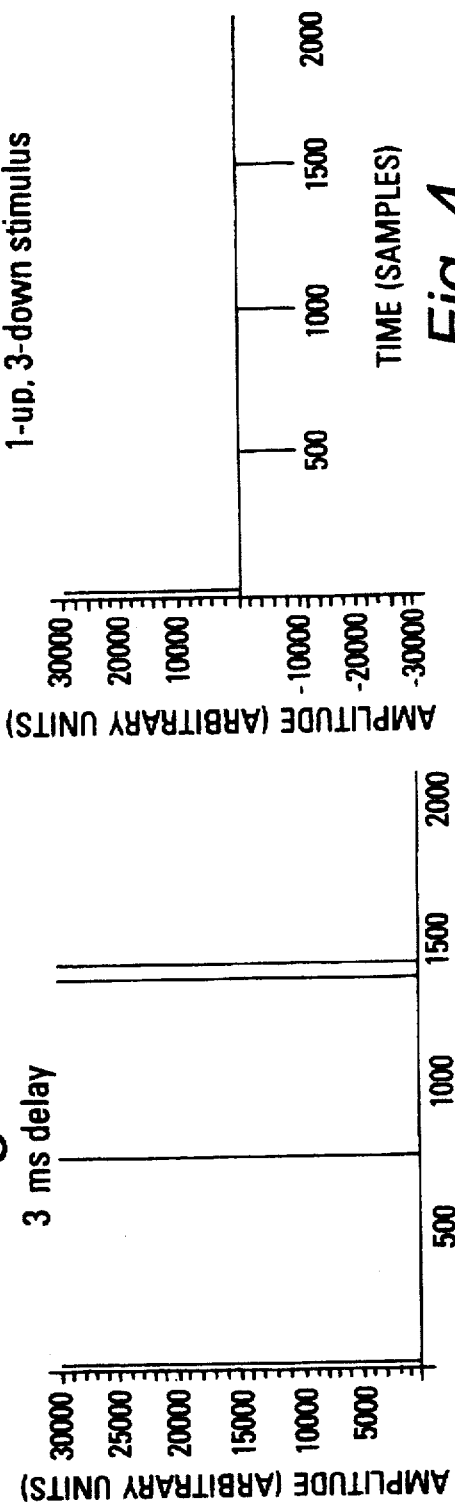

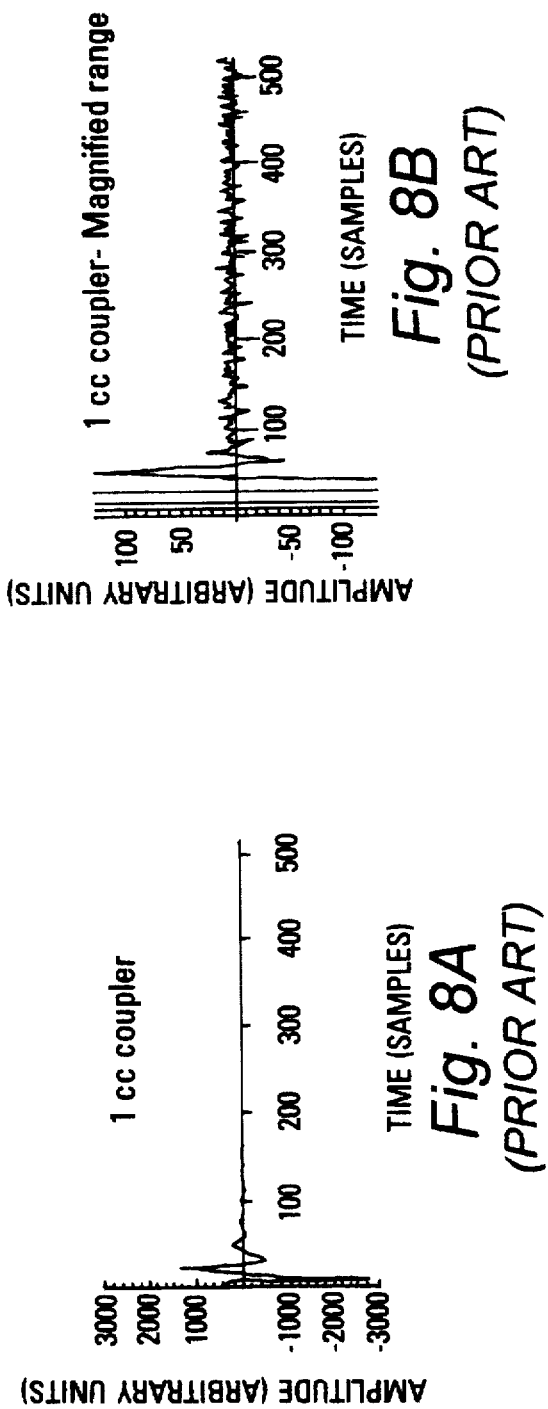
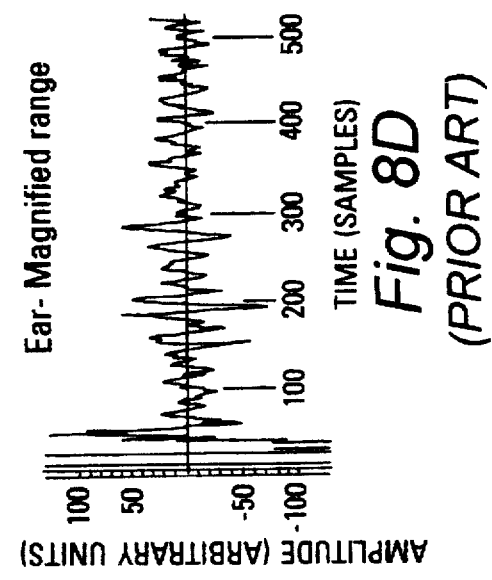
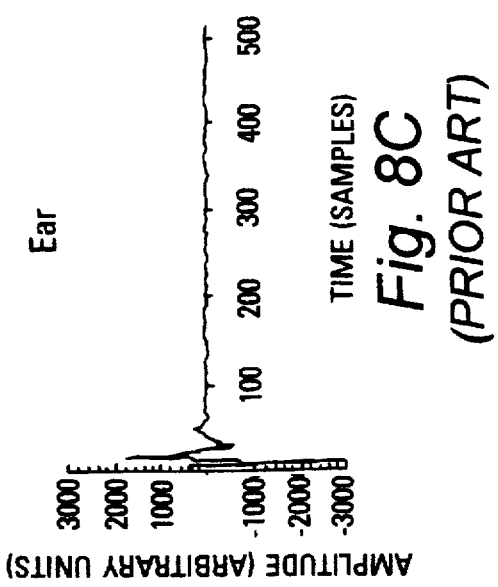
Fig. 8A (PRIOR ART)
Fig. 8B (PRIOR ART)
Fig. 8C (PRIOR ART)
Fig. 8D (PRIOR ART)

1/3 - octave averaged
Ear response (upper curves) and 1-cc coupler response (lower curves)
Signal: solid line
Signal +/- Noise: dashed line 1 ms delay 2 ms delay 3 ms delay Total responses--response to stimulus s1
2CEOAE responses-nonlinear response with zero time
delay between s1 and s2
Noise responses-random noise calculated from
nonlinear coherence

SYSTEM AND METHOD FOR ACOUSTIC RESPONSE MEASUREMENT IN THE EAR CANAL

CROSS REFERENCE TO RELATED APPLICATION

This application is a continuation-in-part of U.S. patent application Ser. No. 08/599,467, filed Jan. 23, 1996, entitled System and Method for the Measurement of Evoked Otoacoustic Emissions.

BACKGROUND OF THE INVENTION

1. Technical Field

The invention is related generally to the field of evoked otoacoustic emissions and nonlinear acoustic transfer functions measured in the ear canal and, more particularly, to a system and method for measuring evoked otoacoustic emissions and nonlinear power-based responses in the ear canal.

2. Description of the Prior Art

Cochlear Otoacoustic Emission Responses

Cochlear response measurements in the ear canal pre-date the discovery of otoacoustic emissions. The importance of measurements of the acoustic impedance of the ear from a location in the ear canal has been long known, beginning with measurements obtained in 1928 and described in "Measurement of the Acoustical Impedances of Human Ears," by W. West, *Post Office Electrical Engineers Journal*, 21:293–300, 1928. Subsequent research has led to techniques that provide information on the external, middle and inner ear. One such system, described in U.S. Pat. No. 3,294,193, issued in 1966 to Zwislocki, describes an instrument that measures a transfer function of the ear.

A subset of this response function provides measurements of reflected energy from the cochlea, because the mid-frequency part of the resistive component of the middle ear impedance is mainly due to the cochlear resistance, as first obtained by measurements in cats and rabbits, as described in "An Experimental Study of the Acoustic Impedance of the Middle Ear and Its Transmission Properties," A. Moller, *Acta Oto-Laryngol.*, 60:129–149, 1965, and *Auditory Physiology*, A. Moller, Academic Press, New York, 1983.

Early research had established the cochlear origin of subharmonic distortion products recorded in ear-canal pressure response measurements, as described in "On the Generation of Odd-Fractional Subharmonics," P. Dallos, *J. Acoust. Soc. Am.*, 40:1382–1391, 1966, and in *The Auditory Periphery*, P. Dallos, Academic Press, U.S.A., 1973. Dallos also commented on his early research into the source of acoustic emissions in Comment on 'Observations on the Generator Mechanism of Stimulus Frequency Acoustic Emissions—Two Tone Suppression' (D. T. Kemp and R. Chum) in *Psychophysical, Physiological and Behavioral Studies in Hearing*, page 42, E. deBoer and M. A. Viergever, editors, Delft University Press, 1980.

Following this early work by Dallos, otoacoustic emissions (OAE's) were discovered by D. Kemp, described in "Stimulated Acoustic Emissions From Within the Human Auditory System," D. T. Kemp, *J. Acoust. Soc. AM.*, 64:1386–1391, 1978. Kemp's discoveries initiated an active period of research continuing to the present on cochlear-based signals that are inferred from pressure measurements in the ear canal. Broadly speaking, OAE's are classified into spontaneous otoacoustic emissions (SOAE), which refer to cochlear-based responses in the ear canal in the absence of any external stimulus, and evoked otoacoustic emissions (EOAE), which arise in response to an acoustic stimulus delivered into the ear canal.

These evoked responses are categorized according to the type of stimulus. The stimulus frequency otoacoustic emission (SFOAE) is obtained using a sinusoidal signal, as described in "Observations on the Generator Mechanism of Stimulus Frequency Acoustic Emissions—Two Tone Suppression," D. T. Kemp and R. Chum, in *Psychophysical, Physiological and Behavioral Studies in Hearing*, pages 34–41, E. deBoer and M. A. Viergever, editors, Delft University Press, 1980. The SFOAE is a low-level signal measured in the ear canal at the frequency of the sine tone, which is based upon the property that the evoked emission has a saturating nonlinearity as the stimulus level is increased.

Other types of stimulus signals include a click-evoked otoacoustic emission (CEOAE) response, described in "Stimulated Acoustic Emissions From Within the Human Auditory System," J. *Acoust. Soc. Am.*, 64:1386–1391, 1978, U.K. Provisional Patent No. 5467/78, 1978 to D. T. Kemp, U.S. Pat. No. 4,374,526, issued Feb. 22, 1983 to Kemp ("Kemp (1983)"), and U.S. Pat. No. 4,884,447, issued Dec. 1, 1989 to Kemp ("Kemp (1989)"). These references describe a measurement that is the pressure response to the presentation of a single click (also termed pulse), or the differential pressure response pulse to the presentation of clicks delivered at two (or more) intensity levels. A click, or, equivalently, a pulse, is a wide-bandwidth, deterministic, short-duration signal. The duration is usually limited by the duration of the impulse response of the acoustic source transducer, since the electrical input signal to the source transducer is typically much shorter than this impulse response duration. The stimulus duration is typically 1–4 milliseconds (msec), whereas the overall duration of the CEOAE response is in the range of 10–40 msec. In the prior art of Kemp (1983), the duration of the CEOAE response is assumed to extend over a 20 msec interval, and to prevent overlapping of the responses from succeeding pulse stimuli, it is stated that the time interval between pulses should be at least 20 msec, corresponding to a presentation rate of 50 Hz. Time-gating of the response is recommended to remove the initial 5 msec of the total response, which is not included in the definition of the OAE response, and this initial portion of the response is thus excluded from the definition of the CEOAE response.

Distortion product otoacoustic emissions (DPOAE's or DP's) are OAE's measured in response to a stimulus comprised of two continuous, sinusoidal tones with frequencies $f_1$ and $f_2$. Information from the DPOAE includes the frequencies at which there are significant intensity levels, for example, at the $2f_1-f_2$ DP site. The term "site" refers to the location in the cochlea that is believed to generate the evoked emission although multiple sites may also be involved. The underlying cochlear mechanisms leading to latencies or time delays in CEOAE also produce latencies in the DPOAE responses, which can be measured in terms of the group delay, as can be appreciated by those skilled in the art, and interpreted to provide information on cochlear micromechanics. The term "latency" refers to the time delay in the evoked response to the stimulus, whereas the group delay is defined based upon the rate of change of the signal phase with frequency. To control for probe nonlinearity in DP measurements, it is typical to use two source probes. One probe outputs the sine tone at $f_1$, and the other probe outputs the sine tone at $f_2$. The use of two independent probes controls for the intermodulation distortion that would otherwise occur at sum and difference frequencies if a single probe were used.

As described in "A Review of Otoacoustic Emissions," R. Probst, B. L. Lonsbury-Martin, and G. K. Martin, *J. Acoust.*

Soc. Am., 89:2027-2067, 1991, current research indicates that these various OAE measurement systems are providing information from a common physiological origin, involving cochlear incromechanics and the mechanisms underlying signal transduction in the cochlea. Thus, advances in EOAE measurement techniques are aimed at providing more accurate, or more comprehensive, data regarding these cochlear mechanisms.

More complex stimuli have been used to measure EOAE's, including tone bursts created using short-duration, rectangular-windowed sinusoids (other windows including Gaussian have been used).

Linear Systems Analysis

While the cochlear response may be assessed using OAE's based upon ear-canal pressure measurements, it is also useful to represent the ear canal as an arbitrary acoustic termination whose response to a given stimulus can be represented as a transfer function. This section summarizes the linear-systems analysis of a one-dimensional acoustic system.

An arbitrary acoustic system, for example, the ear canal, is said to be linear if the output level of an acoustic response variable is proportional to the input level of the acoustic stimulus variable. For example, the acoustic stimulus might be the oscillatory volume velocity of air injected by an acoustic source into the ear canal, and the acoustic response variable might be the pressure measured in the ear canal by a microphone. If the system is linear, then the acoustic pressure doubles in amplitude when the acoustic volume velocity doubles in amplitude. When the acoustic source is a linear transducer, then its electrical input and its acoustic output, in this case, the acoustic volume velocity, are linearly related. For such a linear transducer, the acoustic pressure response is linearly proportional to the electrical input signal driving the acoustic source.

Linear transfer functions may be understood within an input-output system framework as the ratio of an output response to an input stimulus level. For example, the acoustic impedance is the ratio of the acoustic pressure in the ear canal to an acoustic volume velocity signal of unit amplitude. If the system is linear, then this transfer function is independent of stimulus amplitude, e.g., the acoustic impedance of a linear system is independent of stimulus level.

Linear transfer functions allow a power-based description of the acoustic response of the ear. This is not possible with pressure measurements alone. For this reason, they are also called power-based response functions. Any frequency-domain linear transfer function can be interpreted as the steady-state system output in frequency when the stimulus is sinusoidal with unit amplitude and zero phase. Any time-domain linear transfer function can be interpreted as the system output in time when the stimulus is an idealized impulse of unit amplitude, that is, a signal with flat power spectrum and very short duration.

Frequency-domain linear transfer functions include (acoustic) admittance, (acoustic) impedance, and the (pressure) reflection coefficient. All these functions are complex quantities of frequency. The admittance is the volume flow response at a given frequency to a unit pressure sinusoid at the same frequency. The impedance is the pressure response sinusoid to an input volume-flow sinusoid. Admittance and impedance are standing wave descriptions of the sound field whereas the reflection coefficient is a traveling wave description. The pressure reflection coefficient is the ratio of two sinusoids: the reflected pressure wave and an outgoing pressure wave associated with the stimulus.

Time-domain linear transfer functions include the time-domain impedance, the time-domain admittance, and the reflection function. The time-domain impedance is the pressure response as a function of time to a unit volume-flow impulse. It may be formally calculated from the impedance using the inverse Fourier transform. Similarly, the time-domain admittance is the volume-flow response to a unit pressure impulse, and is the inverse Fourier transform of the admittance. The (pressure) reflection function is the reflected pressure response as a function of time to an out-going incident impulse of pressure. It is formally related to the pressure reflection coefficient by the inverse Fourier transform.

The term "reflectance" is used to refer to either the reflection coefficient or reflection function. There are also volume-flow reflectances that are related by a factor of $-1$ to the pressure reflectance in the plane-wave representation, and by well-known factors in other separable coordinate system representations.

In the frequency domain, the impedance $Z(f)$ and admittance $Y(f)$ are related by $$Z(f)=1/Y(f) \qquad (1)$$

It is often convenient to represent these linear transfer functions in terms of their real and imaginary parts as follows:

$$Y(f)=G(f)+jB(f),$$
$$Z(f)=R(f)+jX(f), \qquad (2)$$

where $j=\sqrt{-1}$ and where $R(f)$ is the resistance, $X(f)$ is the reactance, $G(f)$ is the conductance, and $B(f)$ is the susceptance.

The measurement uses a probe assembly inserted into the earcanal in a leak-free manner. The probe assembly is comprised of one or more acoustic sources and one microphone, with an optional additional probe tube to control changes in static pressure within the ear canal. The preferred embodiment uses two acoustic sources. While in place in the ear canal, acoustic source 1 creates a volume velocity $u_1(t)$, acoustic source 2 creates a volume velocity $u_2(t)$, and the microphone measures a pressure response p(t). The corresponding frequency-domain variables are $U_1(f)$, $U_2(f)$, and $P(f)$, respectively. Lower-case letters denote time-domain variables, and upper-case letters denote frequency-domain variables.

The term "power-based responses" signifies that each of the above linear transfer functions (impedance, admittance, reflectance) can be used to calculate the power $\Pi_a$ absorbed by the ear. To introduce the power relations, it is assumed that only acoustic source 1 is utilized, so that $U_2(f)=0$. For the remainder of this section, the volume velocity of acoustic source 1 is denoted as u(t) in the time domain and as U(f) in the frequency domain. In this frequency domain representation, the power absorbed, time-averaged over the period of the oscillation, may be expressed in terms of the conductance, which is the real part of the admittance, or the resistance, which is the real part of the impedance, as follows:

$$\Pi_a(f)=\frac{1}{2}\ G(f)|P(f)|^2, \qquad (3)$$

$$\Pi_a(f)=\frac{1}{2}\ R(f)|U(f)|^2.$$

Since it is the pressure response at the microphone that is measured, then the top relation is more directly utilized: the absorbed power is proportional to the product of the conductance and the magnitude squared of the total pressure. Constant sound pressure level does not imply constant power level.

Except for small contributions from acoustic higher-order modes that are neglected herein, the total pressure and volume velocity at any location in the ear canal, including the tip of the probe assembly, may be separated into incident and reflected components:

$$P(f)=P_i(f)+P_r(f),$$

$$U(f)=U_i(f)+U_r(f). \quad (4)$$

Such higher order mode response may be represented as an inertance in series with the ear canal and a calibration waveguide. The pressure reflectance R(f) is a linear transfer function that is the ratio of reflected to incident pressure:

$$R(f) = \frac{P_r(f)}{P_i(f)}, \quad (5)$$

and the above set of equations may be expressed using a plane-wave coordinate representation in terms of the incident pressure $P_i(f)$ and reflectance by $$P(f) = P_i(f) \{1 + R(f)\}, \quad (6)$$

$$U(f) = \frac{P_i(f)}{Z_c} \{1 - R(f)\},$$

where, to good approximation, the characteristic impedance $Z_c$ of the ear canal is related to the equilibrium density of air $\rho$, the sound speed of air, and the cross-sectional area of the ear canal S via $$Z_c = \frac{\rho c}{S}. \quad (7)$$

If other coordinate systems were used to represent the incident and reflected waves, the specific form of Equation (6) would change in accordance with well-known coordinate transformations, e.g., those described in *Methods of Theoretical Physics*, Parts I and II, P. M. Morse and H. Feshbach (McGraw-Hill, New York, 1953). The power $\Pi_i(f)$ in the incident wave and power $\Pi_r(f)$ in the reflected wave are calculated from $$\Pi_i(f) = \frac{1}{2} S \frac{|P_i(f)|^2}{\rho c}, \quad (8)$$

$$\Pi_r(f) = \frac{1}{2} S \frac{|P_r(f)|^2}{\rho c}.$$

These equations and equation (5) imply that $$\Pi_r(f)=|R(f)|^2\Pi_i(f), \quad (9)$$

so that the energy reflectance, $|R(f)|^2$, defined as the squared magnitude of the pressure reflectance, is the ratio of reflected to incident power in the ear canal (or other one-dimensional acoustic waveguide). By conservation of energy, the incident power is equal to the sum of the reflected and absorbed power. Thus, the power absorbed in the ear canal is $$\Pi_a(f)=\Pi_i(f)\{1-|R(f)|^2\}, \quad (10)$$

so that one minus the energy reflectance is the ratio of absorbed to incident power. This equation and equation (3) provide three equivalent procedures for calculating absorbed power in a linear acoustic system.

Distortion and Noise Reduction in Hearing Test Systems

The purpose of any EOAE measurement is to extract the signal representing evoked cochlear energy, but the measured response is degraded by nonlinear distortion in the measurement apparatus and by random noise. Nonlinear distortion and random noise also degrade measurements of transfer functions in the ear canal. Contributors to random noise include physiological noise that is sensed by the microphone in the ear canal, mainly due to respiration, circulation and vocalizations, electrical noise in the instrumentation, and ambient environmental noise in the room in which the measurements are made. By averaging the response, it is usually possible to reduce the random noise components, although this depends somewhat on the long-term characteristics of the random noise, since changes in the physiologic state of the patient or human subject can elevate the noise floor.

Distortion may occur in the probe assembly due to nonlinearities in the microphone or nonlinearities in the source. Related distortion categorized for present purposes as "probe distortion" includes distortion in each digital-to-analog converter (DAC) or analog-to-digital converter (ADC). The most significant nonlinearity in the probe is typically associated nonlinearities in the acoustic source(s) 130 and 132, that are important as nonlinearities in transients near peak excitation levels. Nonlinear distortion is not significantly influenced by averaging. Nevertheless, an essential first step is to extract the deterministic portion of the total measured response from the randomly varying portion of the response.

This section describes a new technique to reduce random noise, denoted herein as "noise". Noise reduction is essential in practical measurement systems because EOAE's are so low in level. A variety of noise reduction techniques have been applied in CEOAE and DP measurement systems. CEOAE techniques have collected time averages in two or more sub-ensembles of responses, each sub-ensemble corresponding to a time-domain average of a number of individual click responses. The waveforms from any pair of sub-ensembles can be cross-correlated to calculate the reproducibility of the response, as discussed by Kemp (1989) and Probst et al., "A Review of Otoacoustic Emissions," *J. Acoust. Soc. Am.*, 89:2027–2067, 1991, but this technique is not sensitive to the frequency-specific character of physiologic noise, which occurs mainly at low frequencies for respiratory and circulatory noise. The cross-spectrum of two sub-ensembles, calculated in the frequency domain using the DFT of the response, has been used to calculate the CEOAE spectra, but this does not allow an independent estimate of the random noise level. Kemp (1989) proposes correlations between two ensembles of responses preceded by narrow-band filtering, which may imply a frequency-specific correlation.

One approach to measuring the random noise spectrum is to simply subtract the spectra calculated from a pair of sub-ensemble measurements, and convert this difference spectrum to a sound pressure level. This subtraction procedure does not allow an objective determination of the random noise level, as would be obtained by coherent spectral estimation techniques.

DP measurement systems have estimated noise by taking advantage of the frequency specificity of the DP response to two sinusoidal tones. When the response is transformed to the frequency domain using a DFT, each individual DP component resides in a separate spectral bin, whose center frequency is close to the DP frequency. Noise is estimated by comparing the level in the DP bin with the levels in the adjacent frequency bins that do not contain the DP.

Time averaging of the evoked response with artifact rejection and noise rejection is recommended by Kemp et al. (1986) and proposed by Kemp (1989). "Artifact rejection" in this prior art has been taken to include a differential substraction of responses, so as to eliminate the linear response, as in the linearly balanced technique of Kemp (1989), and includes the use of time gating. "Noise rejection" in this prior art is when the sound pressure level (SPL) exceeds some threshold during the portion of the signal after the first 5 ms. This is taken as evidence of a noise source external to the cochlear response. Time averaging is effective at attenuating noise, but has no benefits for reducing the nonlinear response output by the probe that is synchronous with the stimulus presentation rate. Artifact rejection, as used in this application, differs in meaning from that of Kemp (1989) and is defined below.

Different linear cancellation procedures have been utilized in an attempt to control for probe nonlinearity and other measurement-system distortion. One approach measures two responses, a first response to the stimulus at one level and a second response to the same stimulus, but at some higher level, typically on the order of 6–10 decibels (dB) higher. The low-level response is boosted or amplified by the same difference in level (6–10 dB in this example), and subtracted from the high-level response. If the system were linear, then the result would be a null response. Thus, the measured response after subtraction is due to the EOAE response and the synchronous residual probe nonlinearity. The residual probe nonlinearity can be significant and contaminates the beginning of the EOAE response. To eliminate this initial contamination, the EOAE response is typically nulled over the first 2–5 msec, as in Kemp (1983). However, eliminating the beginning of the EOAE response results in the elimination of the high-frequency content of the EOAE which is characterized by short latencies in this range. No techniques exist for these CEOAE or tone-burst EOAE systems to control for probe nonlinearity that are as effective as the two-source probe technique for the DPOAE measurements.

The standard subtraction technique in CEOAE systems, discussed in Kemp (1989), uses a single probe to produce four stimuli. The first three stimuli are three identical clicks and the fourth stimuli is a fourth click, but with the opposite polarity and three times the amplitude of the first three identical stimuli. The responses are summed to produce a response which would be zero if the cochlear EOAE behaved as an ideal linear response. This subtraction of the linear response is the "artifact rejection" of Kemp et al. (1986) and a specific embodiment of the linearly balanced technique of Kemp (1989). This is argued as reducing random noise, but the probe nonlinearity is not controlled.

Kemp (1989) defines the primary response to an ear-canal stimulus to be due to reflection from the ear canal and middle ear, and the secondary response to be indicative of the condition of the cochlea. The secondary response tends to occur after the primary response, but there exists overlap in time. The test instrumentation includes noise that can interfere with the detection of the secondary response, i.e., the cochlear response. Noise in this sense is any signal associated with the measurement system that is not due to the transduced cochlear signal, and will in general include random linear and nonlinear components and deterministic nonlinear components. This latter component is synchronous with the deterministic cochlear signal. All such components are part of the total primary and secondary responses, but the nonlinear components are particularly important in the early time interval following the stimulus presentation, because a large-amplitude stimulus produces larger amplitudes in the measurement-system distortion. Using a linearly balanced set of stimuli and summing the respective responses eliminates only the linear components in the primary response (ear-canal and middle ear responses, and measurement-system distortion), but the deterministic nonlinear component of the primary response is not eliminated. If this component is sufficiently large, then there remains significant overlap between the primary and secondary responses even after summing of the outputs. The practical recourse has been to utilize time gating to ensure separation of the latter part of the secondary cochlear response.

Each of the existing EOAE systems lacks the ability to easily measure a wideband response or suffers from the inability to control for probe nonlinearities. Similar difficulties exist for ear-canal transfer function measurements. Therefore it can be appreciated that there is a significant need for a system and method to measure acoustic responses in the ear canal while controlling for nonlinearities without the use of time-gating. Moreover, present theories do not allow the interpretation of click-evoked OAE responses within the framework of a distortion product-evoked OAE response model, and vice versa. A difficulty with present systems to measure ear-canal transfer functions at different stimulus levels is that measurement-system distortion is a significant source of error. The invention provides solutions to those problems and other advantages, as will be seen from the following discussion and accompanying figures.

SUMMARY OF THE INVENTION

The invention is embodied in a system and method for measuring power-based responses of the ear using a double-evoked stimulus set and related double-evoked subtraction of pressure responses. For example, the invention may be applied to evoked otoacoustic emissions by using a double-evoked otoacoustic emission stimulus and subtracting the responses in a manner that is nearly independent of probe distortion. In one embodiment the stimulus is a double click, while in another embodiment the stimulus signal is a double chirped signal. Signal processing techniques may be applied that unify the interpretation of otoacoustic emission responses in terms of the click-evoked and distortion product-evoked models. In addition, a nonlinear coherence technique is used to separate the deterministic and random components of the response, and leads to an objective measure of nonlinear signal-to-noise ratio appropriate for nonlinear measurements. A real-time artifact rejection technique permits the efficient extraction of the deterministic evoked response from non-stationary noise. A technique is described to measure nonlinear acoustic transfer functions in the ear canal and the power absorbed in the ear canal at two or more stimulus levels. The invention is applicable to the detection and diagnosis of cochlear and conductive impairments in the ears of humans across the age range from neonates, including premature infants, to adults.

BRIEF DESCRIPTION OF THE DRAWINGS

FIGS. 3 to 3C are waveforms illustrating the double-click evoked emission stimulus of the system of FIG. 1.

FIG. 4 is a waveform illustrating the conventional click evoked emission stimulus.

FIGS. 8A to 8D are waveforms of the evoked response to the conventional stimulus of FIG. 4.

DETAILED DESCRIPTION

1. Instrumentation

The invention provides a system and method to measure Double-Evoked Otoacoustic Emissions (2EOAE), whose place of origin is the cochlea, and nonlinear transfer functions in the ear canal and power absorbed in the ear canal at a plurality of stimulus levels.

The inventive system may be easily implemented on a conventional computer system in a variety of configurations of hardware and software that are not critical to the operation of the invention except as specifically described below.

Figure 1:
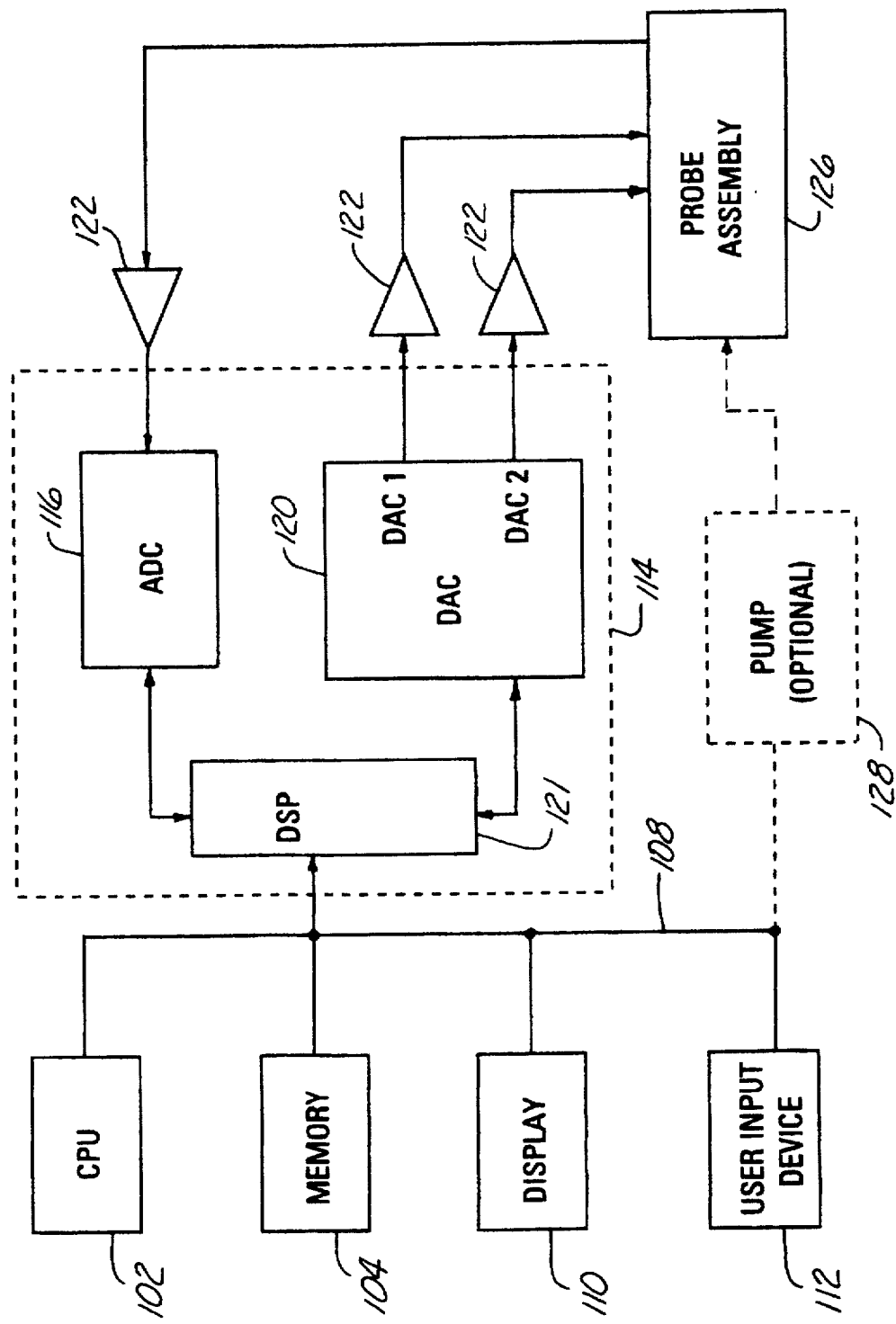
FIG. 1 is a functional block diagram of the system of the invention.

One preferred embodiment of the invention is in a system 100 illustrated in the functional diagram of FIG. 1. The system 100 includes a CPU 102, which is preferably a microprocessor available from Intel Corporation under the tradename Pentium; however, CPU 102 could be any microprocessor having at least the same computational power, such as those available from Intel Corporation under the tradename Pentium Pro, those available from IBM and Motorola under the tradename PowerPC, those available from Digital Equipment Corporation under the tradename Alpha, those available from Sun Microsystems under the tradename SPARC, those available from Silicon Graphics, Inc. under the tradename MIPS, etc. The preferred CPU operates under the operating system available from Microsoft Corporation under the tradename MS-DOS; again, other commercially available operating systems could be used in other implementations of the invention. A memory 104, which may include both random access memory (RAM) and read-only memory (ROM), is coupled to the CPU 102 by a bus 108. Bus 108 may carry power and control signals as well as data. A display 110 and user input device 112 are also coupled to CPU 102 by bus 108. Display 110 preferably is a conventional video display and user input device 112 is preferably a keyboard or a keyboard with an ancillary cursor control device, such as a mouse, trackball, pen, or the like. The operation of these conventional components in the context of this invention is neither critical to the invention nor outside the scope of conventional applications of such components. Other conventional components of the computer system, such as a disk drive, power supply, and the like are omitted here for the sake of brevity.

A hand-held portable system (not shown) might also be constructed, with an appropriately installed CPU, data acquisition system, and probe assembly (described below), which would serve to implement the inventive system. Data would be stored in temporary memory (not shown) and transferred to a remote computer system for further analysis.

It is also possible to practice the invention using (in whole or in part) "single board" or "single-chip" embodiments which combine software and/or firmware used in the preferred embodiment above into application-specific hardware and/or firmware.

System 100 also includes a data acquisition system 114, preferably an Ariel model DSP32C system with Ariel model Proport analog-to-digital converters (ADC) 116 and digital-to-analog converters (DAC) 120, and an AT&T brand digital signal processor (DSP) 121. DSP 121 digitally generates stimuli and processes signals received in response to the stimuli. In the preferred embodiment, system 100 uses either one or two outputs, labeled DAC1 and DAC2, from DAC 120. System 100 also includes filters 122 to filter the inputs to ADC 116 and the outputs from DAC 120. The preferred sample rate chosen for data acquisition system 114 is 16 kilohertz (kHz), which is sufficient for response measurements nearly up to 8 kHz. Filters 122 are lowpass filters with a preferred cutoff frequency 8 kHz. Higher sample rates may be used to acquire ear-canal responses above 8 kHz.

Figure 2:
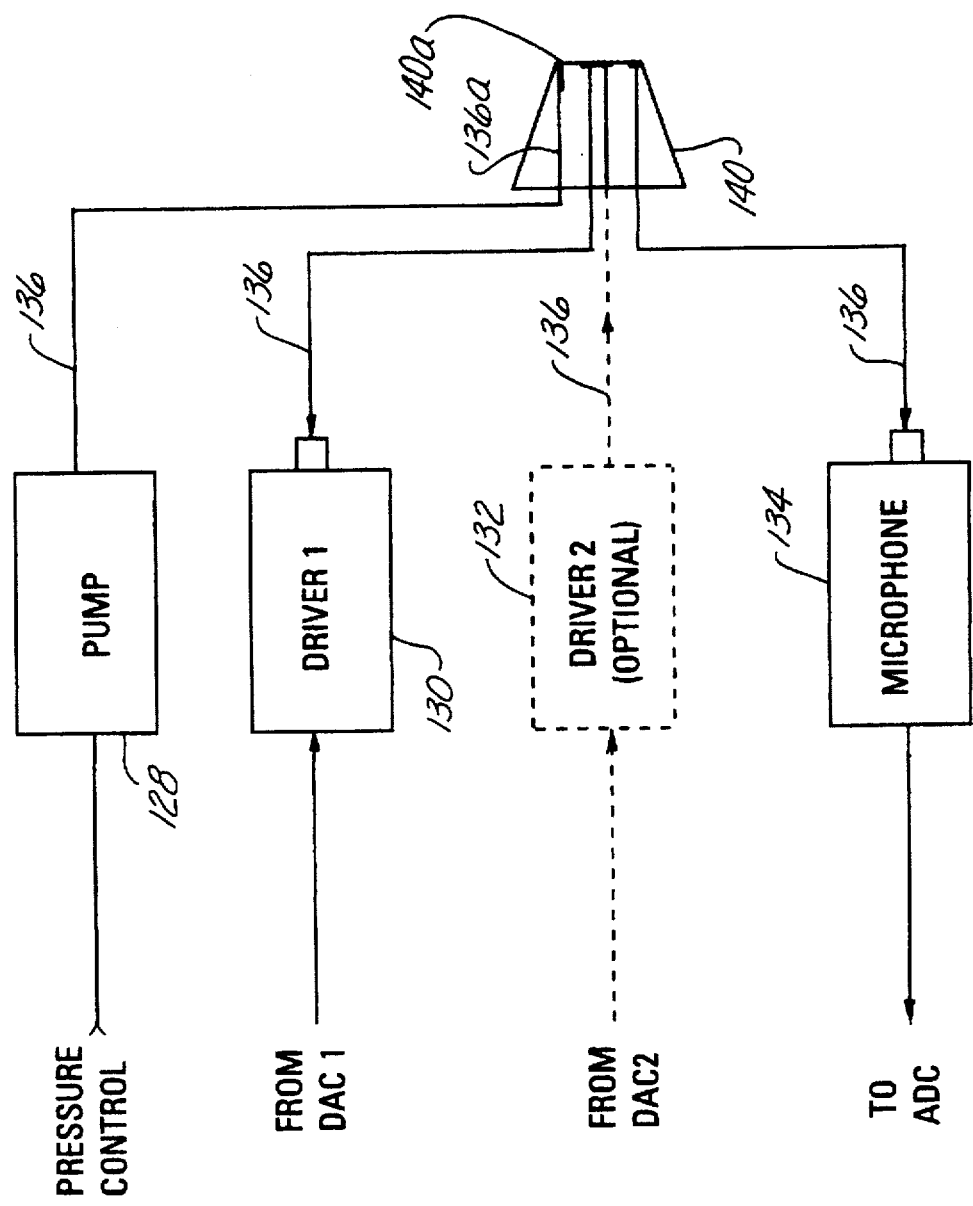
FIG. 2 is a functional block diagram of the probe assembly of the system of FIG. 1.

Data acquisition system 114 is coupled to a probe assembly 126, which is inserted into the subject's ear canal. Details of probe assembly 126 are shown in the functional block diagram of FIG. 2. Probe assembly 126 includes an acoustic source 130, called Driver 1, which is coupled to the DAC1 output of data acquisition system 114. In an alternative embodiment, probe assembly 126 includes an optional second acoustic source 132, called Driver 2, which is coupled to the DAC2 output of data acquisition system 114. Probe assembly 126 also includes a microphone transducer 134, which is coupled to the input of ADC 116. The acoustic outputs of drivers 130 and 132 and the acoustic input to microphone 134 are each connected to an eartip 140 by an acoustic conductor 136, such as a flexible tube. Acoustic conductors 136 all terminate at a probe tip 140a of the probe assembly 140 that is inserted into the ear canal.

Probe assembly 126 may be a commercially available product such as the Etymotic model ER-10C, which contains microphone 134, Driver 1 as one acoustic source 130, and Driver 2 and the second acoustic source 132. In an alternative embodiment, probe assembly 126 may contain only microphone 134 and Driver 1 as the single acoustic source 130. Some preliminary results described herein were obtained using the single-source alternative embodiment, that is, the stimulus delivered to acoustic source 130 using only DAC 120 channel DAC1. The subject in all cases was an adult male with normal hearing. Responses were also obtained in a conventional one cubic centimeter (1-cc) coupler (not shown) to compare the noise floor and probe nonlinearities.

CPU 102 includes an optional port to control the input to an optional static pressure pump 128 that is included in system 100. The varying static pressure is coupled via an external probe tube 136 (see FIG. 2) to probe assembly 126, which includes an internal probe tube 136a to couple variations in static pressure to the ear canal as well as other waveguides used in calibration, if desired.

2. Double-evoked Otoacoustic Emissions in Hearing Test Instruments

A. System Operation

Operation of system 100 may now be described in detail. The new class of stimuli is synthesized on CPU 102. The first step constructs an N-sample window with a deterministic waveform $s_1(t)$. Here, the time variable is denoted by t, but it is understood in a discrete-time implementation that the waveform is defined at each of N discrete time steps. The second step constructs an N-sample window with the waveform $s_2(t)$. The third step constructs an N-sample window with the superposition of these two waveforms, $s_{12}(t)=s_1(t)+s_2(t)$. The composite stimulus s(t) is formed as a 3N-sample window whose initial N samples in the first window contain, $s_1(t)$ whose intermediate N samples in the second window contain, $s_2(t)$ and whose final N samples in the third window contain $s_{12}(t)$. Without loss of generality, the initial, intermediate and final windows may be permuted.

The pressure response in the ear canal is measured to this 3N-sample stimulus, s(t) and time-averaged in the preferred embodiment through multiple presentations of the stimulus. The response is partitioned into three N-sample windows, defined as the response $p_1(t)$ to the stimulus $s_1(t)$, the response $p_2(t)$ to the stimulus $s_2(t)$, and the response $p_{12}(t)$ to the stimulus $s_{12}(t)$.

The stimulus has the property that $$s_{12}(t)-[s_1(t)+s_2(t)]=0, \quad (11)$$

and the linear response of the ear or coupler is eliminated by forming the distortion pressure response $$p_D(t)=p_{12}(t)-[p_1(t)+p_2(t)]. \quad (12)$$

This is an extremely broad class of evoked responses that depend upon the specific choices of $s_1(t)$, $s_2(t)$ and $s_{12}(t)$. This trio of stimuli is called the double evoking stimulus set, or the 2E stimulus set. When a single driver is utilized, this 2E stimulus set differs from the linearly balanced set of stimuli used by Kemp (1989) in that the stimuli in the linearly balanced set algebraically sum to zero, whereas the 2E stimulus set relies on a difference. This has the advantage that the polarity of the stimulus contribution of $s_1(t)$ to $s_{12}(t)$ is matched to the individual polarity of $s_1(t)$, thus allowing an improved cancellation of measurement-system distortion. The subtraction of quantities occurring in both equations (11) and (12) is called the 2E subtraction technique. A desirable reduction in probe distortion is achieved by specific choices of $s_1(t)$ and, $s_2(t)$ with $s_{12}(t)$ constrained in value by Equation (11). One novel family of stimuli is that for which $s_2(t)$ is equal to $s_1(t)$, but delayed in time and scaled in amplitude, that is, $s_1(t)$ and $s_2(t)$ take the form $$s_1(t)=a(t), \quad (13)$$

$$s_2(t)=\epsilon a(t-\tau), \quad (14)$$

where the amplitude ratio $\epsilon$ has a positive or negative value and the relative time delay is $\tau$. The resulting response $p_D(t)$ is called the Double-Evoked Otoacoustic Emission (2EOAE). It is sometimes convenient to refer to $p_D(t)$ as the 2E pressure response. The waveform a(t) is an arbitrary N-sample array of values. The time delay is chosen to be within the range of the EOAE duration (<20 msec) conventionally, but can be measured over larger times. The only constraint on a(t) is that the substantively non-zero response of both a(t) and a(t−τ) lie within the N-sample window of each. This means that the delay τ cannot be too large compared to the overall duration of the N-sample window. This is not a problem in practice, as τ ranges in values from 1–10 msec, with preferred embodiments in the 0–2 msec range, whereas the window duration is at least 20 msec. The stimulus $s_{12}(t)$ takes the form $$s_{12}(t)=s_1(t)+s_2(t)=a(t)+\epsilon a(t-\tau). \quad (15)$$

The signal a(t) is superposed with a delayed copy of itself (re-scaled in amplitude), such that the evoked OAE response to a(t) overlaps the evoked OAE response to a(t−τ) and the nonlinear interaction in the overlap region is controlled by the relative amplitude $\epsilon$. The novel aspect is the subtraction technique for the distortion response $p_D(t)$, which contains a nonlinearly evoked OAE that includes overlapping cochlear reflections to overlapping signals. As previously discussed, Kemp and Chum (1980) and Kemp (1986) described a double-click stimulus with overlapping responses, but the subtraction procedure of Equation (12) was not used to obtain a response and time-gating over the initial 6 msec of the lower-level click response was needed. The use of masker clicks of opposite polarities in this prior art may introduce probe distortion for peak overloading that is asymmetrical between positive and negative polarity clicks. The extent of the distortion increases with increasing click level and may be important for levels used in hearing screening. The stimuli in the Kemp and Chum (1980) double-click procedure do not sum to zero. In contrast, Equation (12) is used without time-gating with a procedure that controls for the probe distortion introduced individually by each source outputting a click. The distortion response $p_D(t)$ thus contains a nonlinearly evoked OAE that includes overlapping cochlear reflections to overlapping signals.

There remains arbitrariness in the choice of a(t). One interesting choice is where a(t) is a click, that is, a shortduration signal whose spectral bandwidth is broad. Short duration signifies that the signal duration is less than the impulse response of acoustic source 130 in probe assembly 126. This leads to the Double Click-Evoked Otoacoustic Emission (2CEOAE). The generation of the 2CEOAE stimulus is discussed in detail below.

Another interesting choice is where a(t) has a duration that is long compared to the impulse response of acoustic source 130 in probe assembly 126, and which is on the order of the duration of evoked OAE responses. That is, the N samples comprising a(t) correspond to a time interval in the range of 20–40 msec. Such stimuli may, without loss of generality, be expressed as a click waveform (i.e., a shortduration waveform) that is allpass filtered. The allpass filter varies the phase of the signal, which influences the temporal distribution of energy, but the spectrum of the filtered signal is precisely the same as the spectrum of the click. Two sub-classes of allpass filters result in chirp waveforms and maximum likelihood sequences, but other choices exist as well.

The preferred embodiment of long-duration signals is the chirp waveform, whose allpass filter group delay, defined below, increases or decreases uniformly with frequency. This class of chirp stimuli leads to the Double Chirp Distortion Product (2ChDP). The generation of the 2ChDP stimulus is discussed in detail below. Alternative embodiments use allpass filters whose group delays vary in a more complicated manner with frequency, including a quasi-random variation of group delay with frequency.

The 3N-sample stimulus s(t) may be output only by acoustic source 130 or by both acoustic sources 130 and 132, each driven by a signal generator and stimulus sequence. In the single-source embodiment, each of the N-sample sub-windows is output by acoustic source 130. In the preferred embodiment that $s_2(t)$ is a time delayed, re-scaled copy of $s_1(t)$, this time delay between $s_2(t)$ and $s_1(t)$ in the jointly presented window $s_{12}(t)$ reduces the level of probe distortion due to peak overload. If the time delay $\tau$ is chosen sufficiently large, then the peak value of $s_{12}(t)$ may be constructed to be much closer to the peak of $s_1(t)$ or $s_2(t)$. This reduction in peak overload during the subtraction of responses to form the distortion pressure leads to a reduction of probe distortion that is nonlinear and synchronous with the cochlear response. Examples are presented below.

Measurement-system distortion, including probe distortion, is significantly reduced when the 2E stimulus sequence is partitioned into two sequences, each of which is output under the control of a digital signal processor (DSP) by a separate digital-to-analog converter (DAC) to a separate acoustic source located within the probe assembly in proximity to a single microphone. This is called the double-source embodiment. The microphone response is digitized using an analog-to-digital converter and acquired by the DSP.

In this double-source embodiment, the overall stimulus presented in the ear canal s(t) consists of repetitions of the 3N-sample sample sequence stimulus s(t) composed of:

the N-sample sequence $s_1(t)$, followed by the N-sample sequence $s_2(t)$, followed by the N-sample sequence $s_{12}(t)$ Channel 1 of the DAC drives Acoustic Source 1 with the 3N-sample signal:

$s_1(t)$ for the initial N samples, zero values for the middle N samples, $s_1(t)$ for the final N samples.

Channel 2 of the DAC drives Acoustic Source 2 with the 3N-sample signal:

zero values for the initial N samples, $s_2(t)$ for the middle N samples, $s_2(t)$ for the final N samples.

these outputs from these two acoustic sources are summed in the ear canal signal. This embodiment has the desirable feature that each acoustic source presents an iso-level stimulus.

In the double-source embodiment of system 100, $s_1(t)$ is output by acoustic source 130, and $s_2(t)$ is output by acoustic source 132. In the presentation of $s_{12}(t)$, defined as the superposition of $s_2(t)$ and $s_1(t)$, $s_1(t)$ is output by acoustic source 130 and $s_2(t)$ is simultaneously output by acoustic source 132. Thus, each of the acoustic sources 130 and 132 outputs only one signal at one level, and the 2E subtraction technique substantively eliminates the distortion of each source from the output distortion response. This is in contrast to the prior art of CEOAE's and tone-burst EOAE's, which use only a single source and which do not maintain constant level from that source. The stimulus sequence output by acoustic source 130 is not linearly balanced, because it includes two presentations of $s_1(t)$ which sum to $2s_1(t)$. Similarly, the stimulus sequence output by acoustic source 132 is not linearly balanced, because it includes two presentations of $s_2(t)$ which sum to $2s_2(t)$. The corresponding linear combination of pressure responses relies on the acoustic mixing of the outputs of each of the two acoustic sources 130 and 132 in the ear canal.

Some obvious extensions to this general formalism may be noted. One is that static pressurization of the ear canal may be included as a variable. The EOAE is measured at various static pressures, which provides information on the cochlear signal in the presence of external modifications to the middle ear, via changes in pressurization.

Another is that the multi-stimulus construction and subtraction technique is not limited to the use of two elementary signals but may be extended to three or more elementary signals. The above described a stimulus s(t) created by joining sub-stimuli $s_1(t)$, $s_2(t)$ and $s_{12}(t)$. Three or more time-delayed copies of a(t) may be used in the construction of these stimuli, the only constraint being that a linear combination of stimulus sum to zero. It is also possible to consider sequences combining $s_{123}(t)$, $s_{12}(t)$, $s_{23}(t)$, $s_{13}(t)$, $s_1(t)$, $s_2(t)$ and $s_3(t)$ in a manner that a linear combination of the stimuli sum to zero. Here, $s_{123}(t)$ denotes the superposition of $s_1(t)$, $s_2(t)$, and $s_3(t)$, etc. For this case of three sub-stimuli, there also exist single-source, double-source and triple-source variants that control more completely for probe distortion.

B. Double-Click-Evoked Otoacoustic Emissions

A short-duration signal $s_1(t)$ is defined by Equation (3) above where a(t) is a short-duration, broadband waveform (click). A second short-duration signal $s_2(t)$ is defined by Equation (14) above as a time-delayed version of $s_1(t)$ with amplitude scaled by $\epsilon$. The constant e may take on arbitrary positive or negative values. A negative value inverts the polarity of the click. The composite signal $s_{12}(t)$ is defined by Equation (15).

The acoustic pressure responses to the stimuli $s_1(t)$, $s_2(t)$ and $s_{12}(t)$ are $p_1(t)$ $p_2(t)$ and $p_{12}(t)$, respectively. The Double-Click-Evoked Otoacoustic Emission (2CEOAE) is defined by the response $$p_D(t)p_{12}(t)-[p_1(t)+p_2(t)]. \qquad (16)$$

This equation is precisely equivalent to Equation (12) for the case that $s_1$ is a click. This is in contrast to the click-evoked OAE in which a stimulus s is presented at two amplitude levels, notated by $s(t, L_1)$ and $s(t, L_2)$, where $L_2=L_1+\Delta L$. The pressure responses at levels $L_1$ and $L_2$ are $p(t, L_2)$ and $p(t, L_1)$, and the click-evoked OAE is $$\Delta p = p(t, L_2) - p(t, L_1). \qquad (17)$$

The 2CEOAE of system 100 manipulates the time delay $\tau$ between clicks as an independent variable, and there is no time-gating of the response with respect to the onset of the stimulus, as there is in prior art, click-evoked OAE techniques. A further advantage is that any linear response of the system is canceled in calculating the 2CEOAE.

It is useful to calibrate the measurement system by applying the stimulus to the probe when inserted into a cylindrical tube. Any peak distortion in the probe can be measured and the spectral amplitude of the stimulus can be adjusted to eliminate the low-frequency energy that is predominantly responsible for overloading the source transducer.

The 2CEOAE measurement procedure has an advantage over the standard CEOAE measurement procedures (Kemp (1989)) since the level of the signal is not varied. Since the peak values associated with $s_1(t)$ are well-separated in time from the peak values associated with $s_2(t)$, then any probe nonlinearity will tend to be equivalent in the single-click and double-click conditions and will thus tend to cancel when Equation (16) is used to calculate the 2CEOAE response. In contrast, the clock-evoked OAE paradigm varies the level of the stimulus, so that any probe nonlinearity does not cancel when Equation (17) is used to calculate the response. This is a critical difference for measuring evoked emissions with latencies less than 5 msec, i.e., high-frequency EOAES, and low-frequency emissions, which are significantly limited by probe distortion.

EXAMPLE I

Sample waveforms for the 2CEOAE stimulus are illustrated in FIGS. 3A to 3C where different time delays $\tau$ are illustrated in each figure. It should be noted that FIGS. 3A to 3C and other figures illustrate time varying waveforms. The amplitude of these waveforms is given in counts on the ADC 116 (see FIG. 1) and are thus displayed in arbitrary units. The time scale is given in terms of samples in ADC 116. FIG. 3A illustrates the three signals, $s_1(t)$, $s_2(t)$, and $s_{12}(t)$ with a delay of $\tau=1$ msec. FIGS. 3B and 3C have identical amplitudes, but time delays $\tau$ of 2 msec and 3 msec, respectively. The scaling factor is $\epsilon=1$ in all three examples of FIGS. 3A to 3C. The waveforms in FIGS. 3A to 3C are taken directly from the output of the DAC1 (see FIG. 1). A variant of the 2CEOAE, using both DAC1 and DAC2, will be discussed below. There are 2048 samples in each composite waveform, corresponding in an overall duration of 128 msec for the sample rate of 16 kHz. Consider the 3 msec time delay stimulus of FIG. 3C. The first third of the waveform in FIG. 3C is $s_1(t)$ with a duration of 682 samples, the middle third of the waveform in FIG. 3C is $s_2(t)$ with the same duration of 682 samples, and the last third of the waveform in FIG. 3C is $s_{12}(t)$ (i.e., $s_{12}(t)=s_1(t)+s_2(t)$) with a duration of 682 samples, terminated by two additional samples with a zero value. These latter two samples are present in these pilot data and their influence is negligible, but the preferred embodiment has the duration of each of the three sub-windows precisely identical. After the subtraction processes in Equation (16) are carried out, the 2CEOAE responses have a duration of D=43 msec, and the CEOAE response has a duration of 32 msec.

The 2CEOAE stimuli illustrated in FIGS. 3A to 3C are contrasted with the conventional linearly balanced set of stimuli illustrated in FIG. 4 measured using the techniques in Kemp (1989). In FIG. 4, each of the stimuli in the set are separated in time so that only one click occurs within the maximum latency for the evoked response from the ear. As discussed above, the time interval between stimuli in Kemp (1989) is at least 20 msec. As such, the stimulus in FIG. 4 comprises four separate stimuli that each have a corresponding evoked OAE response from the ear. In contrast, the 3N sample stimulus s(t) generated by system 100, and illustrated in FIGS. 3A to 3C, have three independent stimuli, but the third stimulus includes two clicks presented with the time delay $\tau$ that is less than the maximum latency time for the evoked response from the ear.

C. 2CEOAE Variants

There are two variants of the measurement procedure, using only acoustic source 130 (see FIG. 2) or both acoustic sources 130 and 132. A single acoustic source can be used with sufficiently large time delay, $\tau$ because the response to the joint presentation of $s_1(t)$ and $s_2(t)$, followed by subtraction of each of the single responses to $s_1(t)$ and $s_2(t)$, produces negligible distortion artifact. The presence of delay offsets the peak values associated with $s_1$ and $s_2$, thereby making the subtraction process effective. In the case of zero delay, the two clicks coalesce into a single acoustic click of twice the amplitude, thereby producing much greater amounts of peak clipping in the single acoustic source. This undesirable property is similar to the technique of Kemp (1989), who subtracts responses based upon clicks of different amplitudes. The double-source variant in which $s_1(t)$ is input to acoustic source 130 and $s_2(t)$ is input to acoustic source 132 substantively eliminates peak clipping distortion. This is the preferred embodiment, although at slightly increased complexity and cost for probe assembly 126 (see FIG. 2).

This double-source variant has a surprising, and significant, degenerate case, when the time delay between the clicks is zero ($\tau=0$), and when the relative click amplitude is unity ($\epsilon=1$). The two click stimuli again coalesce into a single click of twice the amplitude, assuming, without loss of generality, that the two acoustic sources 130 and 132 are identical. By the use of separate acoustic sources 130 and 132 for $s_1(t)$ and $s_2(t)$, the differential subtraction embodied in Equation (16) absolutely eliminates probe nonlinearity that is synchronous to the stimulus window. More generally, measurement-system nonlinearity is eliminated that is within each of the two DAC channels of the measurement system. The measurement-system nonlinearity that remains is due to between-channel distortion, which is much less significant in practical applications. For example, there might be between channel transmission within a given probe assembly from the acoustic source coupling tube to the microphone coupling tube, but such transmission is a linear response, and thus cancels in the 2E subtraction technique. These remarks are applicable not only to the 2CEOAE variant but to any 2E pressure response produced via the 2E subtraction technique using a double-source variant. This allows measurement of a CEOAE without the need for nulling out (i.e., time-gating) the initial 2–5 msec of the response, and allows for much wider bandwidth measurements of CEOAE's.

D. Double-Chirp Distortion Product Stimulus

The operation of system 100 may now be described in detail for the case of a double-chirp stimulus, resulting in the double-chirp-evoked distortion product (2ChDP). The double chirped stimulus signal is synthesized by system 100 and delivered to the ear. The double chirp stimulus has significant advantages over both the conventional two frequency DP stimulus and the conventional click stimulus. Conventional distortion product systems use a pair of sinusoidal signals with frequencies $f_1$ and $f_2 > f_1$ to evoke distortion products at frequencies including $2f_1-f_2$ and other frequencies that are linear combinations of the two stimulus frequencies.

Such conventional DP systems have the advantage that the strongly evoked signals are widely separated in frequency from those in the stimulus, so that they can easily be extracted. They have the disadvantage that the response is obtained at only a single pair of stimulus frequencies, which must be varied to obtain a broad bandwidth response. Typically, special frequencies are used for $f_1$ and $f_2$ whose periods are exact subharmonics of the number of samples N in the window. Such limitations of frequency simplify the digital generation of the stimuli. For example, a 1000-sample window may be used to continuously generate a sine wave whose period is 1000 samples, 500 samples, 250 samples, or any other period that is an exact sub-harmonic of the window period. While this simplifies the synthesis of stimuli, it severely constrains frequency selectivity. This problem is compounded by the property that the DP response may fluctuate significantly if the stimulus frequencies are co-varied by small amounts, for example, in the vicinity of a SOAE site. This means it would be desirable to have a broader range of frequency selectivity in DP measurements. This is made possible with 2ChDP measurements. Transient DP measurement systems using the 2E stimulus set are discussed below.

Click-evoked OAE measurement systems have good frequency selectivity, but the linear response overlaps somewhat in time from the nonlinear response, and, even with appropriate time-domain averaging, there may be limitations in the bandwidth of the evoked OAE response that can be measured when compared to DP systems.

Techniques using chirp-based distortion products by system 100 share advantages with both DP and click-evoked OAE measurement systems. The double chirp stimulus uses a repetitive, but non-continuous, signal well-suited to time-averaging. Compared to a short-duration pulse, a chirp has a greater signal-to-noise ratio and a reduced crest factor, thereby reducing nonlinearities in acoustic source 130. The crest factor is the ratio of the peak to RMS amplitude of the signal.

A wideband multi-chirp stimulus can be created with controllable crest factor whose strongly-evoked cochlear response components are separable from those of the stimulus. Furthermore, such a stimulus has desirable group delay properties of DP measurements. This is achieved using a double chirp, that is, designing a stimulus that is a linear superposition of two chirps. The 3N sample stimulus is defined by Equations (13) to (15) above. The signal s(t) is defined by Equation (13) where a(t) is a chirp signal. The signal $s_2(t)$ is defined by Equation (14) above as a time-delayed version of $s_1(t)$ with amplitude scaled by $\epsilon$. The composite signal $s_{12}(t)$, defined by Equation (15), is the superposition of $s_1(t)$ and $s_2(t)$. However, as previously discussed, system 100 is not limited to stimuli $s_1(t)$ and $s_2(t)$ that are scaled replicas of each other.

E. Linear and Log Chirp Design

Figure 5:
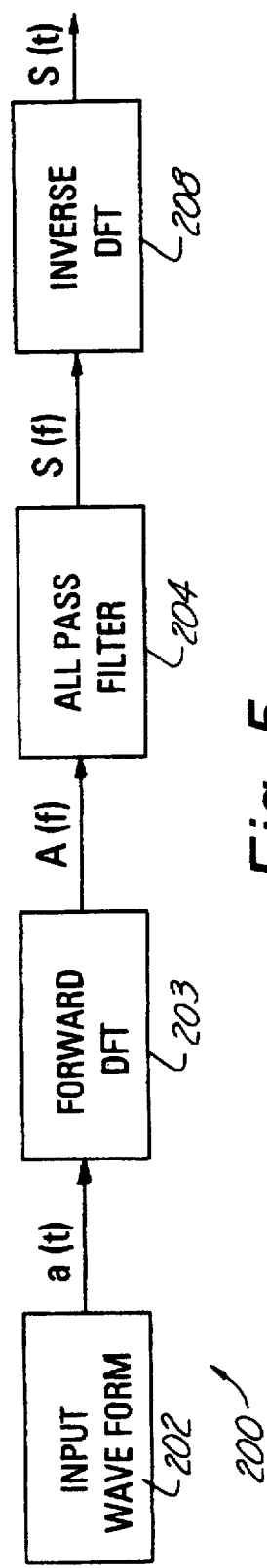
FIG. 5 is a functional block diagram of a chirping circuit of the system of FIG. 1.

The design procedures for producing chirps with linear and logarithmic group delay are summarized in this section. This is illustrated in the functional block diagram of FIG. 5 where a chirping circuit 200 includes an input waveform 202 representing the signal a(t). The signal a(t) is processed by a discrete Fourier transform (DFT) 203 to convert the signal a(t) into a frequency domain signal A(f). An allpass filter 204 processes the frequency domain signal A(f) to produce a chirp whose spectrum contains the same energy as the original signal a(t), but whose energy is spread out in time due to the phase shifting. As will be described in detail below, allpass filter 204 can have a linear dependence on frequency to produce a linear chirp or a logarithmic dependence on frequency to produce a log chirp. Other allpass filter designs are also admissible.

Since the 2ChDP is a particular embodiment of the 2EOAE stimulus design, the initial signal a(t) may be specified in the time domain or, using its DFT 203 A(f), the signal may be specified in the frequency domain. The preferred embodiment of a(t) is a short-duration signal similar to a click. This short-duration signal is filtered by allpass filter 204, and transformed to a time-domain signal using an inverse discrete Fourier Transform (DFT$^{-1}$) 208. The chirped signal is essentially a time-stretched band limited impulse. The chirping circuit 200 is intended merely to illustrate the processing steps that are performed by system 100 to generate the time-stretched band-limited impulse.

Allpass filter 204 is expressed in the frequency domain by $C(f)=e^{j\Theta(f)}$ where the phase response $\Theta(f)$ varies with frequency f or, equivalently, radian frequency $\omega=2\pi f$, and where the unit imaginary number is j based upon a time dependence $e^{j\omega t}$. The group delay $\tau$ of the allpass filter is defined by $$\tau = -\frac{1}{2\pi}\frac{d\Theta(f)}{df}. \tag{18}$$

In a discrete-time implementation based upon a duration of N samples at a sample period of T, the group delay must be in the range of 0–D, where the window duration is D=NT. The k-th discrete frequency is $f_k=k/D$ where k varies from 0, . . . , (N–1). Suppose the upper frequency desired in the stimulus is $f_u$, which is less than $(2T)^{-1}$. Allpass filter 204 of the linear chirp is expressed by $$\Theta = -\beta\frac{f_k^2}{2f_u}D, \tag{19}$$

$$\tau = \beta\frac{f_k}{f_u}D.$$

As $\beta$ varies from 0 up to 1 (or, from 0 down to –1), the corresponding maximum group delay varies from 0 to the window duration D, and the crest factor is uniformly decreased. For positive $\beta$, the group delay of the linear chirp linearly increases with increasing frequency. For negative $\beta$, the relationship is reversed.

The stimulus S(f) is specified as the product of linear chirp allpass filter 204 with an amplitude response A(f) that is a real, non-negative quantity, and is constrained to be zero for frequencies above $(2T)^{-1}$. More generally, it is useful to specify A(f) such that it is non-zero only within the passband of acoustic source 130 (see FIG. 2), and it can be further varied with frequency to optimize the signal-to-noise ratio, the crest factor of the stimulus or measured response, or other desired quantity. The inverse DFT (DFT$^{-1}$) of S(f)= A(f)C(f) is the chirp waveform s(t) used as $s_1(t)$ in a double-chirp stimulus presentation.

The log chirp is constructed using allpass filter 204 whose parameters are selected so that the group delay is proportional to the logarithm of the frequency. Its phase function $\Theta$ may be expressed as $$\Theta = 2\pi\alpha D f_k \left[\log_{10}\left(\frac{f_k}{f_c}\right)-1\right]. \tag{20}$$

The center frequency $f_c$ is the geometrical mean of the lowest ($f_l$) and highest $f_u$ frequencies present, $f_c=\sqrt{f_l f_u}$. The group delay is calculated to be $$\tau = -\alpha D \log_{10}\left(\frac{f_k}{f_c}\right), \tag{21}$$

thus verifying that the group delay varies logarithmically with frequency. When $\alpha$ is positive, the group delay at high frequencies is less than that at low frequencies; when $\alpha$ is negative, these relationships are reversed. The group delay equals zero at the center frequency.

The chirp amplitude A(f) must be of finite bandwidth and avoid the logarithmic singularity at zero frequency. There is a low-frequency transition regime (just above $f_l$) in which the chirp amplitude is increased from zero to unity gain. There is a high-frequency transition regime (just below $f_u$) in which the chirp amplitude is decreased from unity gain down to zero. The chirp amplitude A(f) may otherwise be smoothly varied within the passband, as desired. The total group delay range T(g) is $$T_g = |\alpha| D \log_{10}\left(\frac{f_u}{f_l}\right). \quad (22)$$

Since the number of octaves in the passband is $N_{oct} = \log_2 (f_u/f_l)$, it follows that $$T_g = 0.301|\alpha| D N_{oct} \quad (23)$$

which implies that $|\alpha|$ should be less than $(0.301 N_{oct})^{-1}$ so that $T_g$ is less than $D$. In practice, the log chirp has a shorter duration than this limit so that the EOAE response is contained within the sampling window.

After the inverse DFT, the log chirp can be arbitrarily rotated within the buffer of N samples to align its onset near the beginning of the buffer, thus translating the absolute zero of the center-frequency group delay to any convenient value.

F. Double-Chirp Distortion Product Measurement

System 100 allows the delivery of two chirp signals to the ear to elicit a 2ChDP emission from the cochlea. In this embodiment, either one acoustic source 130 or two acoustic sources 130 and 132 are used to generate the respective chirp signals, as discussed above in the single-source and double-source embodiments of the general 2EOAE measurement. The 2ChDP stimulus offers the dual benefits of broad frequency response not available with the conventional DPOAE technique and good control over probe nonlinearities. The basic idea is to present two log chirps, $s_1(t)$ and $s_2(t)$, with a well-defined relationship between group delay and level. The log chirp is selected in the presently preferred embodiment because it is well known that the tonotopic organization of the cochlea is logarithmic in frequency. Nevertheless, system 100 is intended to encompass the linear chirp stimulus as well as other chirp designs and other allpass filters. Intuitively, each log chirp resembles, over extremely short time scales, a swept sine wave. If two sine waves are swept simultaneously, such that their frequency ratio $m=f_2/f_1>1$ is maintained constant, then a swept DP response will be evoked. In the presently preferred embodiment, three stimuli are used, $s_1(t)$, $s_2(t)$, and their superposition, $s_{12}(t)=s_1(t)+s_2(t)$, and the three corresponding ear-canal pressure responses $p_1(t)$, $p_2(t)$ and $p_{12}(t)$, respectively, are measured. The linear component of the pressure response is subtracted out using Equation (12) above to form $p_d(t)$. The response $p_D(t)$ is the 2ChDP. It is the nonlinear signal that remains from the joint presentation of two chirps, after subtracting out the individual responses to each chirp.

In contrast to the conventional DP measured with a pair of sine tones, the 2ChDP is defined at all frequencies in the measurement bandwidth. In standard usage, the amplitude spectrum of chirp $S_1(f)$ is $A_1(f)=A(f)$, and that for chirp $S_2(f)$ is $A_2(f)=\epsilon(f)A(f)$ where $\epsilon$ is the scaling factor. The sub-class of stimuli with constant $\epsilon$ has interesting properties. A positive value of $\epsilon$ makes the polarity of $s_2(t)$ the same as $s_1(t)$, whereas a negative value of $\epsilon$ produces stimuli with opposite polarity. The chirps differ in level by $\Delta L = 20 \log |\epsilon|$. This enables the amplitude spectrum of the overall signal to be adjusted as desired, but a well-defined spectral level difference is produced that is constant across frequency. This is consistent with common DP measurement paradigms.

How does one further emulate DP measurement paradigms, in which a fixed ratio $m = f_2/f_1$ is maintained between the stimulus frequencies, while $f_1$ is varied? The solution is that the group delay $\tau_1$ of chirp $s_1(t)$ at frequency $f_1$ should be equal to the group delay $\tau_2$ of chirp $s_2(t)$ at frequency $f_2$. It follows that these group delays take the form $$\tau_1(f) = -\alpha D \log_{10}\left(\frac{mf}{f_c}\right), \quad (24)$$

$$\tau_2(f) = -\alpha D \log_{10}\left(\frac{f}{f_c}\right),$$

where the discrete index k of the frequency bin has been suppressed.

The corresponding allpass phase functions, $\Theta_1$ and $\Theta_2$, are needed to construct the stimuli $s_1(t)$ and $s_2(t)$, respectively, and are calculated from $$\Theta_1(f) = 2\pi\alpha Df\left[\log_{10}\left(\frac{mf}{f_c}\right) - 1\right], \quad (25)$$

$$\Theta_2(f) = 2\pi\alpha Df\left[\log_{10}\left(\frac{f}{f_c}\right) - 1\right].$$

Thus, the signal $s_1(f) = A_1(f)e^{j\Theta_1(f)}$, and the signal $s_2(f) = A_2(f)e^{j\Theta_2(f)}$.

While the correspondence of the 2ChDP with the DP measurement paradigm has been stressed, it is also interesting to contrast its properties with other forms of EOAE responses. Evoked-OAE responses typically rely on the subtracted response to a stimulus presented at different levels, whereas the 2ChDP response is a subtracted response to a set of stimuli whose levels are maintained. It has been argued that DPOAE measurements, also called DP measurements, have better signal-to-noise properties than CEOAE measurements because DPOAE responses do not rely on subtracting out the signal response at different levels. The 2ChDP measurement of system 100 shares this desirable property with DPOAE systems.

EXAMPLE II

Figure 6A:
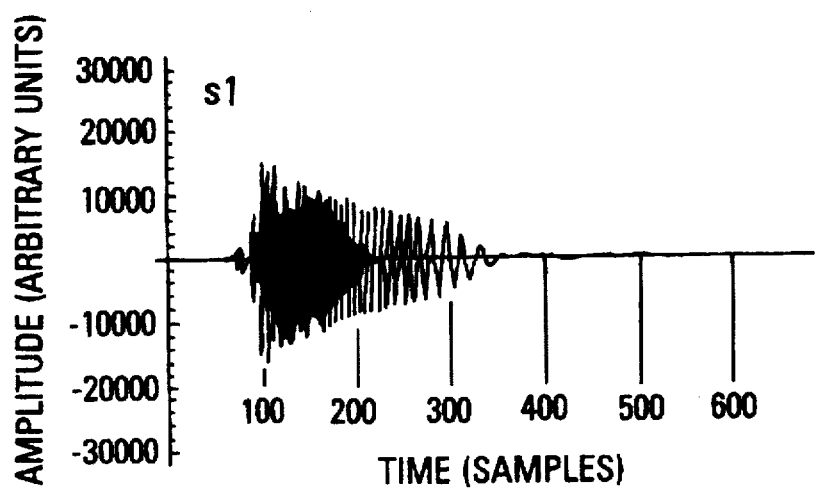
FIGS. 6A to 6C are waveforms illustrating the chirped stimuli generated by the chirping circuit of FIG. 5.
Figure 6B:
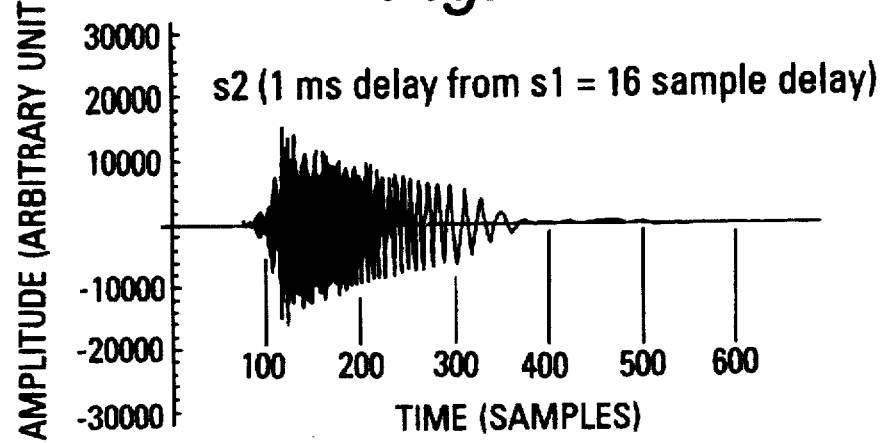
Figure 6C:
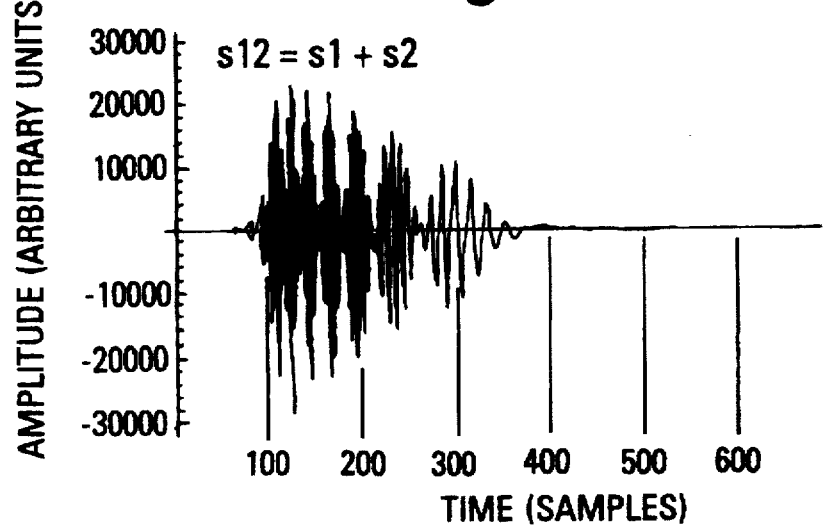

An example of a log chirp stimulus set is illustrated in FIGS. 6A to 6C. The amplitude spectrum $A(f)$ was constant from 500–7800 Hz, with a smooth, half-Hamming window in the spectral domain at frequencies below 500 and above 7800 Hz. The high-frequency roll-off prevented any aliasing difficulties, although both the ADC 115 and DAC 120 have excellent anti-aliasing filters 122. This Hamming window in the frequency domain leads to smooth onset and decay properties in the time-domain waveform. The relative amplitude was set to unity ($\epsilon=1$), and the log chirp coefficient was $\alpha=0.15$. A time delay $\tau=1$ msec was used for $s_2(t)$ relative to $s_1(t)$. Although the peak amplitudes are only slightly less than those of corresponding click waveforms, there is much more energy in the chirp waveforms because the energy is spread out temporally.

FIG. 6A illustrates the first chirp waveform $s_1(t)$ generated at the output of the DAC 1. FIG. 6B illustrates the second chirp waveform $s_2(t)$ generated at the output of the DAC 1. As discussed above, a 1 msec time delay was selected for $s_2(t)$ relative to $s_1(t)$. FIG. 6C illustrates the combination chirp waveform $s_{12}(t)$ generated at the output of the DAC 1. Some amplitude modulation effects are visible in the $s_{12}(t)$ waveform. The individual chirp waveforms $s_1(t)$ and $s_2(t)$ can be generated only by the DAC 1 coupled to acoustic source 130 (see FIG. 2) or generated using both acoustic sources 130 and 132 with the chirp waveform $s_1(t)$ being generated by the DAC 1 coupled to acoustic source 130 while chirp waveform $s_2(t)$ is generated by the DAC 2 coupled to acoustic source 132. In this latter embodiment, the combination chirp waveform $s_{12}(t)$ is generated acoustically as a result of the independently generated outputs of acoustic source 130 and acoustic source 132.

It will be appreciated by those skilled in the art that the 2ChDP response defined in Equation (16) differs from the frequency specific response in ordinary DP measurements. When the magnitude of the 2ChDP response is converted to sound pressure level (SPL), so removing the phase information, the response is similar to that of a broadband CEOAE measurement. It is the phase information that enables the tracking of frequency-specific distortion products such as $2f_1-f_2$. Each of these frequencies is swept in the chirp stimulus, so that each distortion product is swept in the 2ChDP response. The phase of the signal can be used to construct individual trajectories of distortion-product components over time. Useful techniques for calculating such trajectories include wavelet analysis or time-frequency analysis. Wavelet analysis can reduce noise while simultaneously controlling the time and frequency signal attributes, as described by G. Strang and T. Nguyen, "Wavelets and Filter Banks", (Wellesley-Cambridge Press, Wellesley), 1996. Time-frequency analysis is the preferred embodiment, and a useful time-frequency analysis technique is the Choi-Williams transform, "Improved time-frequency representation of multicomponent signals using exponential kernels," *IEEE Transactions on Acoustics, Speech and Signal Processing*, Vol. 37, No. 6, 862–871 (1989). Other time-frequency transforms (or distributions) with satisfactory properties might alternatively be employed, including those discussed by Leon Cohen, "Time-Frequency Analysis", Prentice-Hall, New Jersey (1995). Since the 2ChDP response is broadband, it becomes possible to calculate each distortion product trajectory, whose frequency is $mf_1+nf_2$ for integers measurement and n, with significant spectral energy. It is in this way that an equivalence in the representations of double click-evoked and distortion product-evoked responses is constructed. The latency of each trajectory is influenced not only by the group delay of the allpass filter but also by the frequency-specific latency of the otoacoustic emission, involving travel-time to the cochlear reflection site (or sites), and back.

G. 2ChDP Variants

The 2ChDP procedure offers significant advantages over existing systems. The set of stimuli may be output by the single acoustic source 130 (see FIG. 2), and probe nonlinearity is partially controlled for by the 2E subtraction process. This variant is similar to the linear cancellation procedures used in CEOAE systems, but can be superior due to the lower crest factor of the chirp stimulus. As described below, there is no need to null out the beginning of the 2ChDP response. Thus, system 100 offers an advantage over conventional systems in that the short latency response can provide useful information about high frequency EOAE.

The second, and preferred, embodiment is to use two acoustic sources 130 and 132 in the double-source variant. The first acoustic source 130 outputs the first stimulus $s_1$ and the second acoustic source 132 outputs the second stimulus $s_2$. This controls for intermodulation distortion created by joint presentation of both stimuli using only the single acoustic source 130. This variant is similar to some DPOAE measurement systems that implement two separate acoustic sources, but has the additional advantage of wideband response, as discussed above.

H. The Dechirped 2ChDP Response

Figure 7:
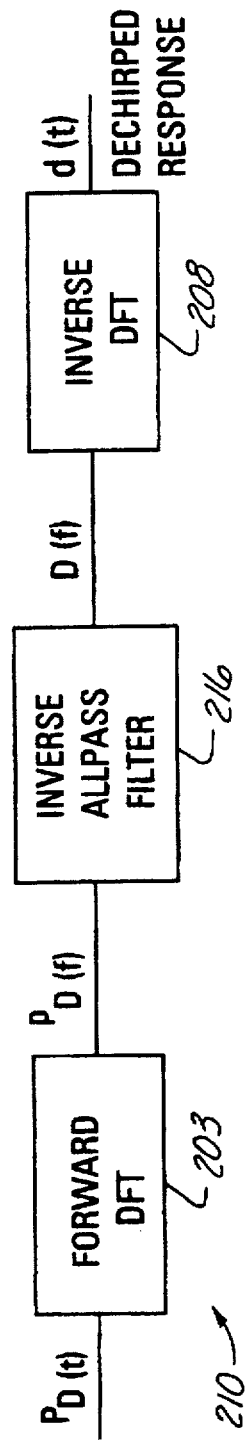
FIG. 7 is a functional block diagram of a dechirping circuit to dechirp the response evoked by the allpass filtered signal of FIG. 5.

The 2ChDP response $p_D(t)$ cannot be easily interpreted because the stimuli have been filtered by allpass filter 204 (see FIG. 5), and the responses share this characteristic. One solution is to remove the influence of allpass filter 204 using dechirping circuit 210, shown in FIG. 7. Dechirping circuit 210 includes forward DFT 203 to convert the $p_D(t)$ from the time domain to the frequency domain. Dechirping circuit 210 then processes the frequency domain response signal by applying an inverse allpass filter 216 with the characteristic $e^{-j\Theta(f)}$ to the frequency domain response. Inverse DFT 208 converts the output of inverse allpass filter 216 from a frequency domain response to a time domain response. This time domain response is denoted as the dechirped response, and represents the response to an equivalent click stimulus.

This operation is analyzed for the example of the log chirp stimulus. The log chirp stimuli are transformed using forward DFT 214 to the frequency domain with transforms denoted by $S_1(f)$ and $S_2(f)$. Suppose the inverse allpass filter $e^{-j\Theta(f)}$ 216 is chosen. Equation (25) implies the following simple relationship between the group delays and the phase functions (a similar relationship can be readily obtained for the linear chirp):

$$\begin{aligned} \tau_2(f) &= \tau_1(f) + \tau, \\ \theta_2(f) &= \theta_1(f) - 2\pi f \tau, \\ \tau &= \alpha D \log m. \end{aligned} \quad (26)$$

For example, double-chirp stimuli are constructed with time delays $\tau$ of 1, 2 and 3 msec. Using Equation (26) above, the corresponding DP frequency ratios are m=1.4, 2.0 and 2.9, respectively. The 1 msec delay case is most closely related to frequency ratios used in typical DP experiments. There is no limitation in using even smaller time delays to produce DP frequency ratios between 1.0 and 1.4.

It follows that the dechirped stimuli $D_1$ and $D_2$, respectively are $$D_1(f) = e^{-j\theta_1} S_1(f) = A(f),$$

$$D_2(f) = e^{-j\theta_1} S_2(f) = \epsilon A(f) e^{-2j\pi\tau}. \quad (27)$$

The impulse response of the filter $A(f)$ is $a(t)$ so that the dechirped time-domain stimuli are $$\begin{aligned} d_1(t) &= a(t), \\ d_2(t) &= \epsilon a(t-\tau), \end{aligned} \quad (28)$$

where $d_i(t)$ is the inverse DFT of $D_i(f)$ for i=1 or 2. The form of the latter equation is due to the time-shift properties of the DFT. The dechirped stimulus $d_{12}$ corresponding to the composite stimulus $s_{12}(t)$ is $$d_{12}(g) = a(t) + \epsilon a(t-\tau). \quad (29)$$

If $\epsilon$ (f) varies with frequency, then the second term in the above is the convolution of $\epsilon$ (t) with $a(t-\tau)$, where $\epsilon$ (t) is the inverse DFT of $\epsilon$ (f).

In application, ear-canal responses are measured using the double-chirped stimulus, and it is the measured microphone response that is dechirped using the inverse allpass filter.

An important conclusion is that the dechirped, double-chirp stimuli in the time domain are isomorphic to a pair of two short-duration pulses that vary in relative latency and level. This time-domain representation of the 2ChDP response allows data analysis within the framework of a response evoked by a pair of equivalent clicks. The form of Equation (29) is equivalent to the general 2EOAE form of Equation (15), as expected.

This exemplifies the novel relationship between DP measurements and evoked OAE measurements that differs in form from previous discussions comparing DP's and click-evoked OAE's. The dual to the frequency-domain DP response is the time-domain double-click response. DP measurements use a stimulus composed of two sine tones, and the parallel in the time domain uses two clicks.

Discussion

A feature of the 2CEOAE response that is not shared by the click-evoked response, is that the 2CEOAE response may be chirped to define an equivalent distortion-product response. The argument is precisely the inverse of that given earlier. The 2CEOAE responses are forward transformed using the DFT, allpass filtered using $e^{j\Theta_1}$ and then plotted versus the group delay $\tau_1$. Alternatively, the phase reference of $\Theta_2$ may be adopted. Time-frequency representations and wavelet transformations may also be used to identify the equivalent DP trajectories in a two-dimensional time-frequency space. This introduces a new way to link understanding of distortion-product and click-evoked OAE's.

While the stimuli in the 2ChDP and 2CEOAE have a dual relationship between the chirped and dechirped conditions, their nonlinear responses may not be simply related. By comparing both 2ChDP and 2CEOAE responses under both conditions, the nature of the cochlear nonlinearity can be probed as regards its spectral and temporal distortion.

Both the 2ChDP and 2CEOAE methods have signal processing advantages over existing DP and evoked OAE methods that may lead to clinical applications, in particular, improved detection and diagnosis of cochlear impairments in neonatal and adult humans. In addition, the measurement of conductance and other components of impedance and reflectance would enable detection of conductive impairments, so that a combined system might be useful for simultaneous detection and diagnosis of both conductive and cochlear hearing impairments.

I. Double-evoked DPOAE Measurement 2E stimuli may be used to measure distortion product otoacoustic emissions (DPOAE), denoted as 2DPOAE's. As discussed above, such DPOAE's are one measure of the nonlinear response of the cochlea, in which the stimulus is comprised of the superposition of sine tones at a pair of frequencies, $f_2$ and $f_2$.

A 2DPOAE measurement uses a 2E stimulus of the form of Equation (11). Again, the elementary stimuli are as follows: $s_1(t)$ is a sine tone at frequency $f_1$, $s_2(t)$ is the sine tone at frequency $f_2$, and $s_{12}(t)$ is the simultaneous presentation of these sine tones. As before, $p_1(t)$ is the pressure response to $s_1(t)$, $p_2(t)$ is the pressure response to $s_2(t)$, and $p_{12}(t)$ is the pressure response to $s_{12}(t)$. The corresponding continuous 2EOAE pressure response is the 2DPOAE, typically evaluated at combination-tone frequencies including 2$f_1-f_2$. The 2DPOAE differs from the conventional DPOAE in that the 2E subtraction of responses in Equation (12) is used to calculate $p_d$, which in this instance is the 2DPOAE.

The 2DPOAE also provides measurements of SFOAE responses in the $f_1$ and $f_2$ frequency bins, due to mutual suppression effects when $f_1$ and $f_2$ are presented simultaneously versus individually.

Regarding the 2DPOAE implementation, the overall durations of $s_1$, $s_2$ and $s_{12}$ need to be sufficiently long that the non-zero portion of the transient stimulus is fully contained in each stimulus, and it is an option to zero-pad each stimulus so that the responses associated with these stimuli also decay to their background noise-dominated range of values. The preferred embodiment is to use separate sources to output $s_1$ and $s_2$, so that probe and other measurement-system distortion effects are minimized.

It may be useful to use $\tau$ in the range of $\pm 5$ ms, and to choose $\epsilon$ such that the amplitudes of the transient cochlear excitation associated with $s_1$ and $s_2$ are approximately equal, as can be estimated using well-known cochlear models. For example, when $f_2 \approx 1.2 f_1$ it is convenient to choose the relative amplitude $\epsilon$ to be on the order of 0.3.

Variations in the time delay are equivalent to a phase difference between the sinusoidal tones, and the relative amplitude between the sinusoidal tones is arbitrary. The following choices may be advantageous. Variations in $\tau$ test the temporal nonlinear interactions between the cochlear responses to the primary frequencies $f_1$ and $f_2$. It may be useful to examine the transient 2DPOAE response using time-frequency representation or wavelet analysis.

The 2DPOAE may be measured as a function of static pressurization of the ear canal.

J. Generalizations

Time-frequency analysis and wavelet analysis have been introduced as useful techniques to further analyse the 2ChDP and the chirped 2CEOAE. Time-frequency analysis and wavelet analysis can also be employed to analyse the general class of 2E responses defined by Equation (12) that are measured using the double-evoking stimulus set of Equation (11). This 2E stimulus set makes no assumptions on the form of the stimulus waveforms comprising the set. In fact, the wavelet transform can be regarded as a type of time-frequency analysis with frequency bins that are logarithmically spaced in frequency. Such methods allow the extraction of individual time-frequency trajectories of specific components of the overall 2E response.

3. Nonlinear Coherence in Hearing Test Instruments

There exist well-known techniques for obtaining independent estimates of signal and random noise levels from experimental data. These techniques are referred to as coherence estimation methods, as described in Bendat, *Nonlinear System Analysis and Identification From Random Data*, 2nd ed. Wiley, New York, (1990) ("Bendat (1990)"). These are based upon the use of cross-spectral and autospectral processing in the frequency domain using independent ensembles of responses. Intuitively, the random noise is uncorrelated with the deterministic stimulus used to evoke a response. It follows that the random noise and the evoked deterministic response in the ear canal are incoherent. These techniques can be applied to the general case of a measured 2E pressure response, and are thus applicable to each particular embodiment. Because the 2E pressure response is nonlinear, it is necessary to define a nonlinear coherence.

The signal level, expressed in decibels, is equal to ten times the common logarithm of the signal autospectrum, and the noise level is similarly related to the noise autospectrum. The autospectrum is defined in Bendat (1990), and corresponds to what is often called in signal processing the "power" or "energy" calculated from the noise autospectrum. This terminology is not used herein, because the term "power" is reserved for the physical concept of power. The purpose of coherence estimation is to obtain separate estimates of the signal autospectrum and the noise autospectrum.

Coherence estimation is formulated in the frequency domain. It is convenient to adopt a separate notation in this section. At frequency f, the stimulus input to acoustic source 130 (see FIG. 2) is X(f), and the response output measured by microphone 134 is Y(f). It is assumed that microphone 134 has linear response and negligible internal noise. The linear transfer function between stimulus and response is H(f). This transfer function takes account of the frequency response of acoustic source 130 and microphone 134, and the linear response of the external, middle and inner ear to stimulus presentation at the probe tip 140a. The signal H(f)

X(f) linearly contributes to the measured output Y(f). There are two additional outputs that are assumed. One is random measurement noise R(f), due to acoustic source transducer noise, physiologic and environmental noise. The signal R(f) is uncorrelated with X(f). Another is a nonlinear distortion signal D(f), that has two components, nonlinearity in the probe and nonlinearity in the ear (i.e., the EOAE).

The output signal is $$Y(f)=H(f)X(f)+R(f)+D(f). \tag{30}$$

The technique of cross-spectral estimation, described in Bendat (1990), is used to calculate the coherence. The technique depends upon the existence of separate ensembles of measurements. Ensemble averaging is used, such that $G_{uv}$ denotes the cross-spectrum between any pair of signals U(f) and V(f), and $G_{uu}$ denotes the autospectrum of U(f).

The cross-spectrum $G_{xy}$ of the input and output signals is calculated from Equation (30) to be $$\begin{aligned}G_{xy}(f) &= H(f)G_{xx}(f) + G_{xr}(f) + G_{xd}(f) \\ &= H(f)G_{xx}(f) + G_{xd}(f),\end{aligned} \tag{31}$$

The cross-spectrum of the input signal with the noise is zero, $G_{xr}=0$, since R(f) is uncorrelated with the input signal. $G_{xd}$ is the cross-spectrum of the input with the nonlinear distortion signal D(f). This represents the relationship between the stimulus and the synchronous nonlinear response associated with the measurement system. The frequency response function $\hat{H}(f)$ of the system is defined as $$\hat{H}(f) = \frac{G_{xy}}{G_{xx}} = H(f) + \frac{G_{xd}}{G_{xx}}. \tag{32}$$

This demonstrates that the frequency response of the system is biased by the presence of distortion, since $\hat{H}(f)$ does not equal H(f).

Examples of calculations of the nonlinear coherence function are given for the general case for this system in Maki, "Interpretation of the coherence function When Using Pseudorandom Inputs to Identify Nonlinear Systems," Trans. Biomed. Engr. BME-33:775–779, 1986. In the present invention, a subtraction procedure is carried out to remove the linear response of the system. Applying this subtraction procedure to the nonlinear coherence analysis results in a much simpler nonlinear coherence function than in the prior art. This is accomplished by subtracting the linear system response, H(f)X(f), from both sides of Equation (30), defining the new nonlinear variable $\tilde{Y}(f)$ by $$\tilde{Y}(f)=Y(f)-H(f)X(f)=R(f)+D(f). \tag{33}$$

Thus, the cross-spectrum $\tilde{G}_{xy}$ of X(f) with $\tilde{Y}(f)$ $$\tilde{G}_{xy}=G_{xy}-HG_{xx}=G_{xd}. \tag{34}$$

The autospectrum of $\tilde{Y}(f)$ is $$\tilde{G}_{yy}=G_{dd}+G_{rr}, \tag{35}$$

since the noise is uncorrelated with the deterministic distortion. Equation (35) states that the total measured output autospectrum, after subtracting off the linear response, is the sum of the distortion signal autospectrum and the noise autospectrum.

The nonlinear coherence function $\gamma^2$ is defined by $$\gamma^2 = \frac{|\tilde{G}_{xy}|^2}{\tilde{G}_{xx}\tilde{G}_{yy}} \tag{36}$$

and quantifies the ratio of the output nonlinear power $\tilde{G}_{yy}$ that is coherent with the input power $G_{xx}$. The nonlinear coherence varies between zero and unity. A calculation of this coherence from the above definition leads to the following relation:

$$\gamma^2 = \frac{G_{dd}}{G_{dd}+G_{rr}}. \tag{37}$$

The nonlinear coherence is equal to the ratio of the distortion autospectrum to the sum of the distortion and the noise autospectra. Equation (37) will be used to define the distortion signal-to-noise ratio, the coherent distortion autospectrum and the noise autospectrum. Before defining these quantities, the method of calculating the nonlinear coherence from the sampled data is summarized.

The nonlinear coherence is implemented using Equation (36). The autospectra are calculated by a sum (i.e., ensemble average) over K statistically independent measurements of the underlying variables $X_i$ and $\tilde{Y}_i$, i ranging from 1, . . . , K. An important simplification occurs because the input variable is the stimulus $X(f)=S_1(f)$, which is precisely known. The cross-spectrum and autospectra are calculated using $$\tilde{G}_{xy}(f) = (1/K)\sum_{i=1}^{K} X_i^*(f)\tilde{Y}_i(f) = (1/K)S_1^*(f)\sum_{i=1}^{K} \tilde{Y}_i(f), \tag{38}$$

$$\tilde{G}_{yy}(f) = (1/K)\sum_{i=1}^{K} |\tilde{Y}_i(f)|^2,$$

$$G_{xx}(f) = (1/K)\sum_{i=1}^{K} X_i^*(f)X_i(f) = |S_1(f)|^2,$$

where the asterisk denotes the complex conjugation operation. The random-error variances of the autospectra and cross-spectrum are proportional to 1/K. Thus, increasing the number of averages increases the accuracy of the spectral estimation. It is obvious that the choice $X(f)=S_2(f)$ is equally applicable.

One important fact is that averaging over frequency is equivalent to averaging over ensembles, since random noise is uncorrelated across frequencies. Thus, the variance of estimating the auto- and cross-spectra can be reduced by averaging over adjacent frequencies. It is typical for hearing applications to average over the log frequency axis. The results below demonstrate that ⅓-octave averaging is sufficient to obtain adequate signal-to-noise, but octave averaging provides for even larger signal-to-noise, and is sometimes desirable for hearing screening applications and might be desirable for some clinical applications in hearing.

The resulting nonlinear coherence, with the substitutions $S_1(f)=X(f)$ and $P_D(f)=\tilde{Y}(f)=P_{12}(f)-[P_1(f)+P_2(f)]$, is "(1/K)" to the right side of the equation as follows:

$$\gamma^2(f) = (1/K)\frac{\left|\sum_{i=1}^{K} P_D(f)\right|^2}{\sum_{i=1}^{K} |P_D(f)|^2}. \tag{39}$$

Equation (42) is the desired result for the coherence, calculated from the sampled pressure signal in the ear canal or coupler.

The nonlinear signal-to-noise ratio, termed the distortion-to-noise ratio DNR is defined in terms of coherence by $$DNR = \frac{\gamma^2}{1-\gamma^2}. \tag{40}$$

Thus, the signal-to-noise ratio is large when the coherence approaches unity, and small when the coherence approaches zero. The DNR evaluates to $$DNR = \frac{G_{dd}}{G_{rr}}, \tag{41}$$

which is precisely the intuitive notion of nonlinear signal to noise.

It follows from Equations (35) and (37) that the coherent distortion autospectrum $G_{dd}$ is calculated from the product of the coherence function and the total autospectrum $\tilde{G}_{yy}$.

This concludes the decomposition of the measured nonlinear response into a deterministic component and a random component. An EOAE measurement system can provide both absolute reproducibility ($\gamma^2=1$) and meaningless data. If the coherence is close to unity, then the random noise power is negligible, but there remain two components to distortion, probe and cochlear distortion. In practice, measurements in a calibration tube, for example, a 1-cc coupler, quantifies the distortion power due to probe and other system nonlinearities. When any type of EOAE response is measured (CEOAE, DPOAE, 2ChDP or 2CEOAE), the nonlinear coherence should be high and the distortion power should be significantly larger than that in the calibration tube, in order to validate that a response has a physiologic component.

A final complication is to account for impedance differences between the coupler and the ear canal, so that the distortion in both the coupler and ear are compared with respect to acoustic power absorption.

The criterion for deciding that an EOAE is present may be chosen in the manner outlined below. Measurements are obtained in a 1-cc coupler or other calibration cavity that mimics some properties of the ear, and also in the ear. The nonlinear coherence is calculated so that confidence limits are constructed using well-known techniques for detecting a deterministic signal in the presence of random noise, as discussed in Bendat (1990). The fractional sub-division of the octave can be varied to increase the number of ensemble averages, and thereby, more easily attain a given confidence limit. Multiple regression, or, equivalently, analysis of variance, is performed to test whether the EOAE response exceeds that of the calibration cavity response. If a significant difference exists, then well-known multiple comparison tests can optionally be used to identify particular octaves or sub-octaves in which EOAE responses are significantly larger than probe distortion responses.

4. Artifact Rejection in Hearing Test Instruments

Artifact rejection is defined herein to be the elimination of exceptionally noisy data from the measured response. Such exceptional events are due to large-amplitude spikes in physiologic and environmental noise, and occasional glitches in the electronics. These represent non-stationary noise. The methods of time averaging and ensemble averaging are conventionally used to remove stationary noise components, but it is preferable to detect the existence of exceptional events before the corresponding responses are included in the averaging process. Such a technique can be designed to operate in real time, which means sufficiently rapidly that responses containing such artifacts can be detected and excluded during the process of data acquisition. Such a realtime artifact rejection method is of undoubted importance in hearing screening and related clinical applications, because valid data may be acquired in much shorter times by the exclusion of bad responses. Moreover, a real-time artifact rejection technique may lead to the acquisition of valid data when all other techniques fail. Because it is able to capture individual "good" responses even in the presence of large-amplitude, but intermittent, noise. Alternatively, the artifact rejection technique can be applied after all data are acquired, by storing all responses in memory.

A. Real-Time Technique

The real-time technique is implemented on the DSP 121 (see FIG. 1), which is the real-time controller of stimulus output via the DAC 120, response input via the ADC 116, time-averaging of responses, and communication with the CPU 102. The DSP 121 acquires the current buffer of response data from the ADC 116 and compares it, sample by sample, to the previous buffer of data that is stored in the DSP memory (not shown).

The real-time artifact rejection technique takes as input the pressure responses measured by a probe assembly in the ear canal using a microphone, and an input that can be varied in real time that controls the threshold level for rejecting data as invalid. Its outputs include judgments of whether each buffer of data is valid or not, and, if valid, the buffer is also output by the technique. As such, there is no explicit reference to how these pressure responses are subsequently used. Thus, the technique is applicable to any acoustic measurement technique that repetitively outputs an acoustic stimulus and measures the response. The stimulus may be output by one or more acoustic sources in a probe assembly inserted into the ear canal, or by one or more acoustic sources in the free field or at some other arbitrary location specified with reference to the ear canal. The pressure response may be measured by a microphone in the ear canal or at some other location relevant to a test of hearing.

It can be understood that a technique to extract a deterministic response of known validity from a repetitively output acoustic stimulus (or stimulus set) has wide applicability to tests of hearing. Such applications include the measurements of evoked otoacoustic emissions, distortion products, transfer functions of the ear including impedance, admittance and reflectance, sound power absorbed by the ear, and an ear-canal pressure response used to interpret an auditory brainstem response measurement or other auditory neurophysiological response, or a behavioral response measurement such as a threshold measurement. In these latter cases, the validity of the ear-canal pressure response may be used as a criterion to help judge whether or not the simultaneously measured neurophysiological response is valid. Alternatively, the behavioral threshold response measurements might be accepted only for stimuli such that the ear-canal pressure response indicates low noise.

The technique of artifact rejection depends upon the comparison of a vector of currently measured responses with a vector of stored measured responses. The task is to determine whether the currently measured response contains valid data or not. Since the stimulus is repetitively output, the response of a deterministic system in the absence of noise should be constant, in the absence of any sensitivity of the deterministic system to changes in initial conditions. The presence of background noise, including time-varying physiologic noise, can significantly degrade the measured response. The stored measured response is taken to be representative of the response of the ear in the presence of relatively low background noise. The currently measured response is compared to the stored measured response. If the two responses are sufficiently similar, then the currently measured response is considered valid data, and, as such, can be used to calculate a time-average response over valid data sets. Otherwise, the currently measured response is invalid, and considered to be unreliable due to noise artifacts. It is discarded and not used to calculate the time-average response. The real-time aspect of this invention is to determine the degree of similarity, and hence, whether or not the currently measured response is valid, during the process of data acquisition.

Prior art real-time systems do exist in which peak levels of the currently measured response are used with a threshold criterion to test for the presence of artifact (Kemp 1989). However, significant physiologic noise may be present, but not exceeding the threshold criterion used. Also, if a probe assembly is used, the probe may move within the ear canal, and the measured response, although invalid, might be accepted by a peak-level test. The proposed technique can successfully cope with this problem. The ability to compare the currently measured response with a stored response that is representative of a low-noise response gives a more sensitive method of artifact rejection. As such, fewer time averages are needed to achieve a given level of signal to noise. This is of particular importance for hearing tests on neonates and young infants, who tend to have much larger levels of physiologic noise with larger changes in general physiologic state.

Both the stored and currently measure responses are vectors whose elements are the set, or any sub-set, of responses at discrete times or discrete frequencies. The preferred embodiment in real time is in the time domain, so the vectors are simply the digitized time series (i.e., waveform), or some subset of the digitized time series. Alternatively, the currently measured response may be comprised of one or more sub-buffers, each of which is a response to the same acoustic stimulus. Then, the stored measured response may be one of the sub-buffers in the currently measured response which is compared to another of the sub-buffers in the currently measured response.

Any prior art technique to calculate the similarity of two time series may be used in this technique. One choice of similarity is the norm of the difference of the two vectors, using any convenient norm. The smaller the norm of the difference, the more similar are the stored and currently measured responses.

Any prior art technique to classify the relative similarities obtained into two categories, valid and invalid, may be used. One choice is to test whether the similarity is less than some threshold, and, if so, to accept the currently measured response as valid. Otherwise, it is invalid. This type of threshold is quite different from the peak threshold criteria in the prior art. Another choice is to assign a probability function for data validity that varies with the measure of relative similarity. The more similar the two responses, the more probable that the currently measured response is valid. The decision rule is thereby stochastic, weighted by the chosen probability function.

There are alternative embodiments for the stored measured response in addition to those discussed above, for example the stored measured response may be the previously judged valid response. If the currently measured response is classified as valid, then it may be copied as the stored measured response for subsequent tests of validity. To begin data acquisition, the stored and currently measured response in one embodiment are the first and second data buffers acquired. If the currently measured response is determined to be invalid, both data buffers are discarded and new data are loaded into the stored and currently measured response buffers. This is to ensure that the stored measured response does not contain data with significant artifacts.

Another embodiment is one in which the stored measured response is a function of two or more of the previously judged valid response buffers. This might be a running average, calculated as the running sum divided by the number of valid buffers acquired, or a time-weighted average in which the most recently acquired buffers are more highly weighted than less recently acquired buffers. The latter embodiment is advantageous since the physiologic noise floor can fluctuate significantly during data acquisition due to changes in physiologic state, and due to noise sources associate with respiration and blood circulation.

Another real-time refinement is to allow the operator of the hearing test instrument to adjust during data acquisition the parameters governing the classification into valid or invalid responses. For example, the operator may increase or decrease the threshold value used in a threshold classification embodiment, or the relative shape in the probability function in a stochastic classification embodiment. This allows the operator to control for variability between subjects in physiologic and other noise, state-dependent physiologic changes during the acquisition of data on a particular subject, or the degree of recency to use in the time-weighted average embodiment.

B. Examples and Discussion

EXAMPLE III

2CEOAE Response

The conventional CEOAE responses and the 2CEOAE responses of system 100, time-averaged over 128 presentations, were measured using procedures described above, and digitally filtered below 400 Hz to attenuate low-frequency noise. The conventional CEOAE responses, using the Kemp (1989) 1-up, 3-down linearly balanced stimulus set of FIG. 4, are illustrated in FIGS. 8A to 8D.

The electrical input was in the up-state for 2 samples, or 125 μs. FIG. 8A illustrates the waveform response to the conventional CEOAE stimuli in the 1-cc coupler. FIG. 8B is the identical response with the vertical sale magnified. FIG. 8C illustrates the response to the conventional CEOAE stimuli in the ear. FIG. 8D is the identical response with the vertical scale magnified.

The probe nonlinearity was clearly present in both the 1-cc coupler (FIG. 8A and 8B) and in the ear (FIGS. 8C and 8D) over the initial 64 samples (approximately 4 msec). It is this early part of the CEOAE that is conventionally nulled in order to obtain a meaningful response.

Figure 9A:
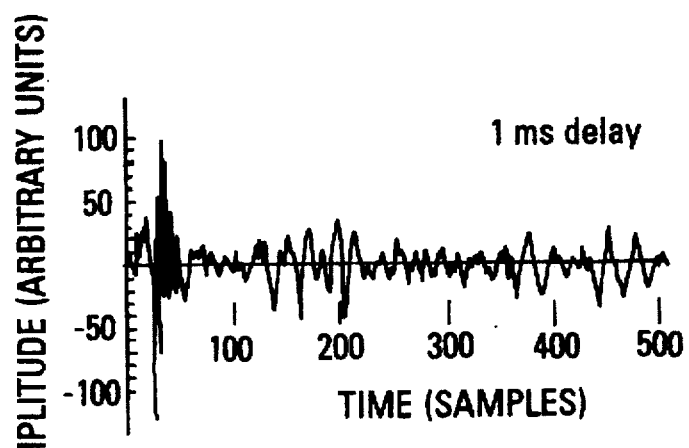
FIGS. 9A to 9C are waveforms of the double-click evoked emission stimulus response of the system of FIG. 1 to the stimulus of FIGS. 3A to 3C.
Figure 9B:
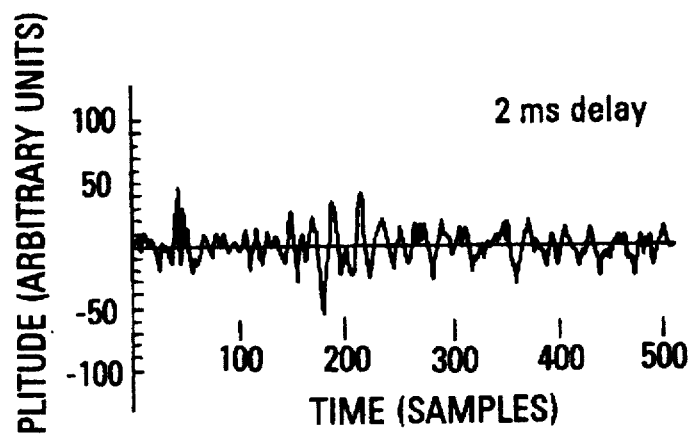
Figure 9C:
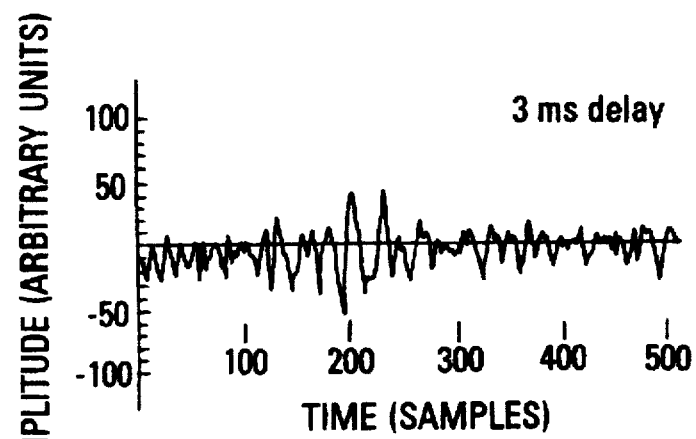

The response to the 2CEOAE stimulus of system 100 is significantly different from that of the conventional CEOAE. The 2CEOAE responses of system 100 in the ear were also significantly larger than those in the 1-cc coupler. The 2CEOAE stimuli of system 100 are illustrated in FIGS. 3A to 3C for time delays ranging from 1–3 msec. The responses in the ear to the 2CEOAE stimuli of FIGS. 3A to 3C are illustrated in FIGS. 9A to 9C, respectively. As seen in FIGS. 9A to 9C, the probe distortion in the early latency response is significantly reduced compared with the conventional CEOAE responses shown in FIGS. 8A to 8D.

The more interesting comparison emerges across the range of time delays used to construct the stimuli. For a 1 msec time delay, there is a large-amplitude spike in the response at early latencies, shown in FIG. 9A, which corresponds to probe distortion. This same effect was observed in the 1-cc coupler responses. As the time delay increases to 2 and 3 msec, the probe distortion completely disappears, as shown in FIGS. 9B and 9C. Even at a time delay of 1 msec, the probe distortion is only 3% in peak amplitude of the probe distortion in the conventional CEOAE measurement of FIG. 8C. The conclusion is that the probe nonlinearity is reduced by a factor of 30 in the 2CEOAE measurement relative to that in the conventional CEOAE measurements.

EXAMPLE IV

2ChDP Response

Figure 10A:
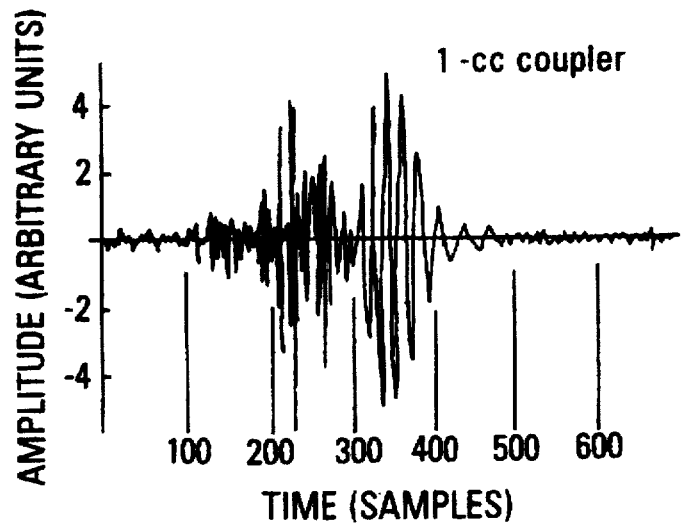
FIGS. 10A to 10B are waveforms of the double chirped evoked emission stimulus response of the system of FIG. 1 to the stimulus of FIG. 6A.
Figure 10B:
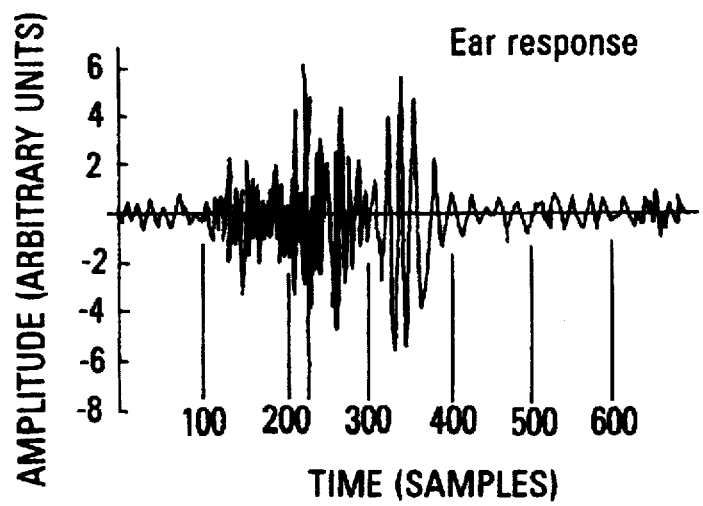

The 2ChDP responses using the stimuli of FIGS. 6A to 6C are illustrated in FIGS. 10A and 10B for the measurement in the 1-cc coupler and in the ear, respectively. These measurements differed from the preceding 2CEOAE measurements in that the responses were lowpass filtered using a Krohn-Hite analog filter (not shown) with a cutoff frequency of 400 Hz before digitization by the ACD 116 (see FIG. 1). These responses were 64 averages of each of two sub-ensembles of responses. The response in the ear was significantly larger than that in the coupler—note the different amplitude scales in FIGS. 10A and 10B.

Figure 11A:
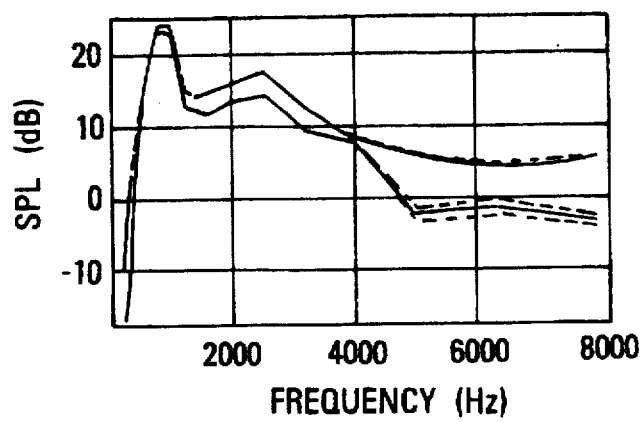
FIGS. 11A to 11C are power spectra of the double chirped evoked emission stimulus responses of the system of FIG. 1 to the stimulus of FIGS. 6A to 6C.
Figure 11B:
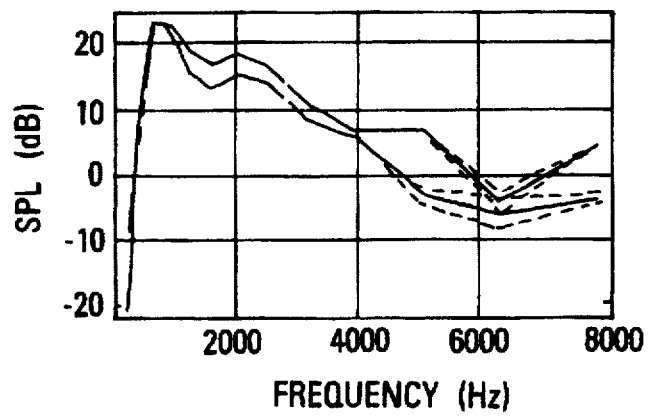
Figure 11C:
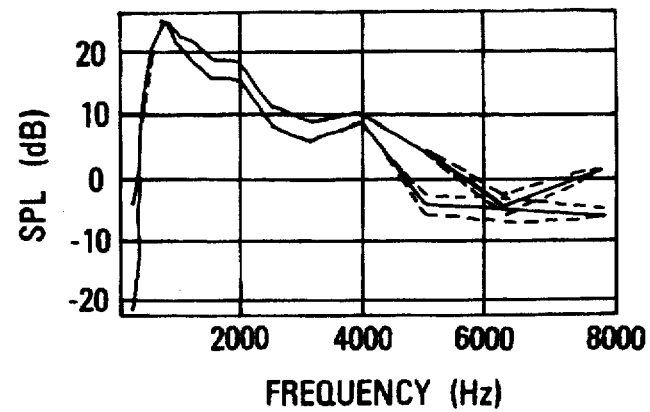

The chirp spectra were calculated along with the distortion signal-to-noise ratio DIVR. FIGS. 11A to 11C plot the 2ChDP spectra (dB SPL) in solid lines using the relation, SPL=20 log($P_D/P_o$) where $P_o=2\times10^{-5}$Pa. The dashed lines above and below the solid line plot 20 log [($P_D/P_o$) (1+1/$\sqrt{DNR}$)$^{\pm \frac{1}{2}}$], respectively. The three plots of FIGS. 11A to 11C illustrate the 2ChDP response for 1 msec, 2 msec, and 3 msec time delays, respectively. There are two sets of measurements on each of the three plots of FIGS. 11A to 11C. One set corresponds to the ear measurement and the other to the 1-cc coupler measurement. The 1-cc coupler measurements, along with its noise range, were always lower in level than the ear measurements.

The nonlinear coherence method discussed above effectively de-coupled the separate influences of random noise from probe distortion. The signal-to-noise ratio was always larger for the ear measurements than the coupler measurements, because the EOAE response was larger. The coupler measurements demonstrated that probe distortion was significant, particularly at low frequencies (500–2000 Hz). This is illustrated in FIGS. 11A to 11C by the near intersection of the responses from the 1-cc coupler and the ear, indicating that the response is not caused by the ear, but by probe nonlinearities. From 5000–8000 Hz, the coupler measurements indicate that random noise was a significant limiting factor, because the dashed lines are observed to deviate from the mean. This directly shows the reduction in distortion noise power to random noise power.

Figure 12A:
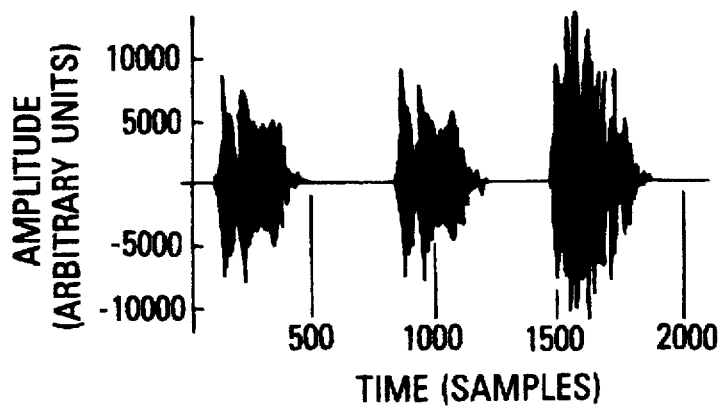
FIG. 12A is a waveform of the double chirped evoked emission stimulus response of the system of FIG. 1 to the chirped stimulus of FIG. 6C.
Figure 12B:
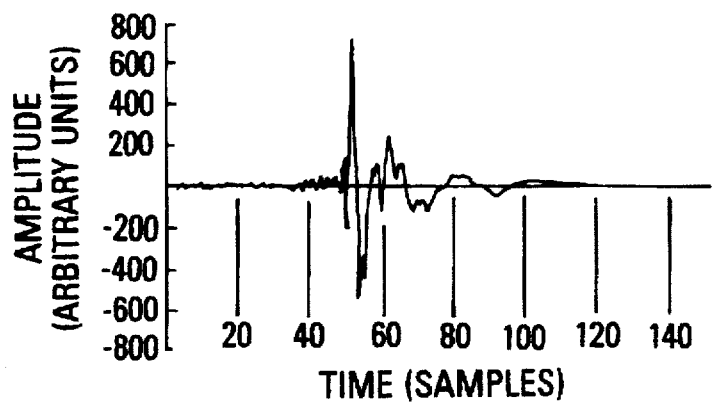
FIGS. 12B to 12D are dechirped responses to the double chirped evoked emission stimulus response of the system of FIG. 1 to the chirped stimulus of FIG. 6C.
Figure 12C:
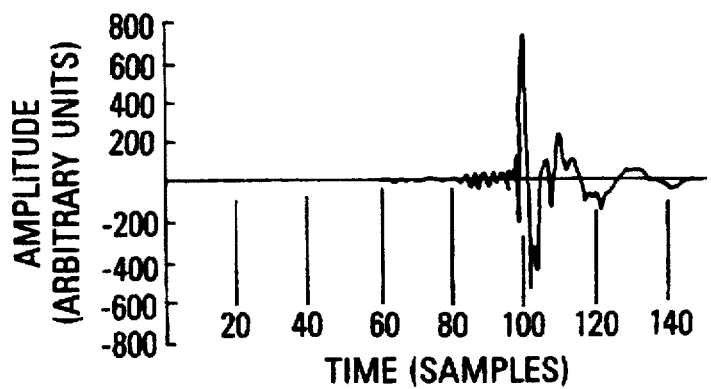
Figure 12D:
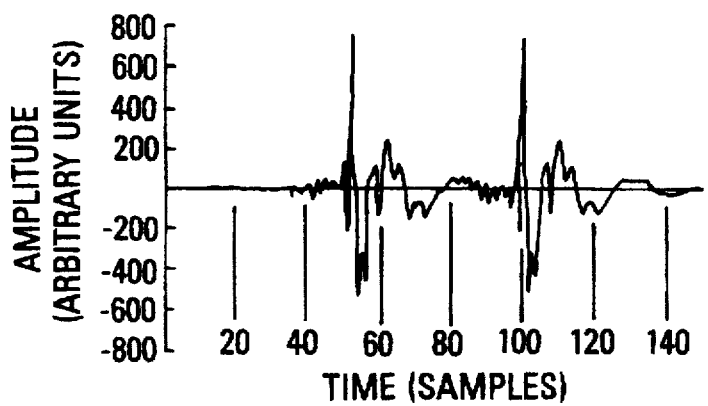
Figure 13A:
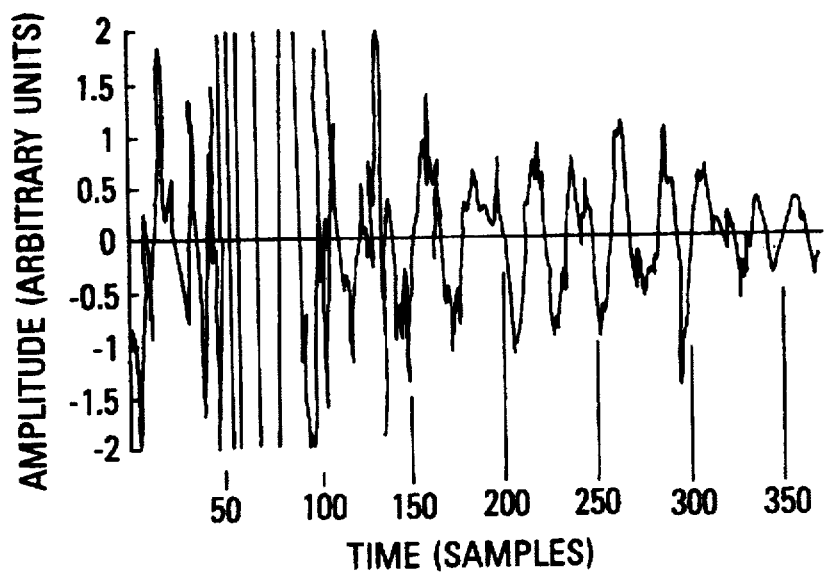
FIG. 13A is waveforms of the difference response illustrating the nonlinear response to the chirped stimulus of FIG. 6C.

The most interesting feature of these plots is the structure of the 2ChDP emission as the inter-stimulus time delay is varied. With a 1 msec time delay, the 2ChDP emission, shown in FIG. 11A, was clearly present from the third octave above 1 kHz to the third octave just below 8 kHz. With 2 and 3 msec time delays, the 2ChDP emission, shown in FIGS. 11B and 11C, respectively, was present at slightly lower frequencies (in the 1 kHz third-octave) because of a reduction in probe distortion, but there was a notch in the 2ChDP emission at 6.3 kHz. These results are very promising because they have been obtained with a single source, for which probe distortion effects were significant. FIGS. 12A to 12D show intermediate states in the signal processing by system 100. The plot in FIG. 12A illustrates the 2ChDP chirp response in the ear for time delay $\tau=3$ msec. The plots of FIGS. 12B to 12D show the dechirped responses to the dechirped stimuli over their initial 150 samples (approximately 9.4 msec). The equivalent peak amplitude of 800 millipascals (mPa) corresponds to a peak equivalent level of 92 dB SPL. The 3 msec (i.e., 48 sample) delay is obvious in the equivalent $d_{12}$ response waveform. The actual peak levels in the ear canal were much lower due to the use of the chirp stimulus. The difference response to the 2E subtraction $d_D(t)=d_{12}(t)-[d_1(t)+d_2(t)]$ is illustrated in the plot of FIG. 13A. There is a large-amplitude response at early latencies in the dechirped response. This is a manifestation of probe nonlinearity, which would be reduced by using a pair of acoustic sources 130 and 132 (see FIG. 2). Nevertheless, the probe distortion is sufficiently small to have enabled adequate detection of the 2ChDP emission in FIG. 11C over a broad range of frequencies.

Figure 13B:
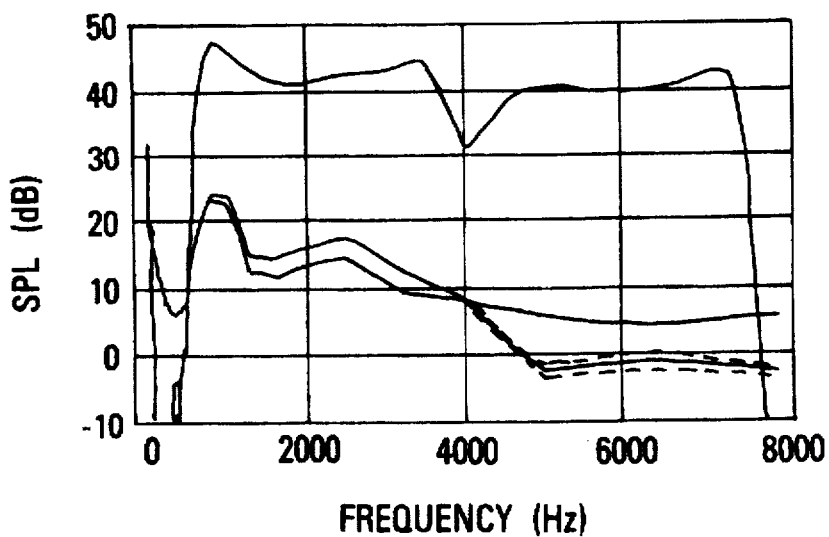
FIG. 13B is power spectra of the double chirped evoked emission stimulus responses of the system of FIG. 1 to the stimulus of FIG. 6C.

The plot in FIG. 13B re-draws the 2ChDP spectrum for time delay $\tau=1$ msec along with the total ear-canal level (narrow-band spectrum rather than ⅓-octave averaged) produced by the $S_1(f)$ stimulus. At low frequencies near 800 Hz, there is a maximum in the ear-canal level of 48 dB SPL that correlates to the peak distortion in the probe nonlinearity.

EXAMPLE V

Double-Source, Zero Time-Delay Variant of 2CEOAE Response

The 2CEOAE stimuli were constructed with equal amplitude ($\epsilon=1$) and zero time delay ($\tau=0$), but a double-source configuration was used. This means that each acoustic source 130 and 132 (see FIG. 2) outputs an identical click simultaneously that is acoustically mixed within the ear canal or coupler to form a single click. It was predicted that this stimulus with the subtraction method described above leads to reduced probe distortion as well as the ability to measure an OAE without the use of conventional time-gating.

Figure 14A:
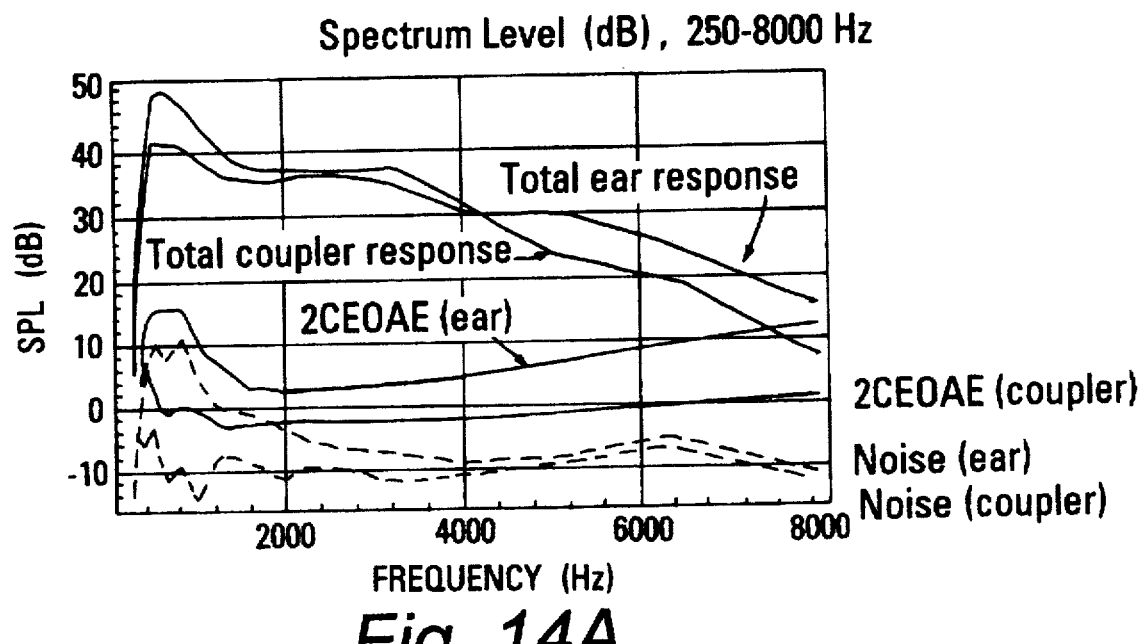
FIGS. 14A and 14B are power spectra of the double-clicked evoked emission stimulus responses of the system of FIG. 1 to a double-source single click.
Figure 14B:
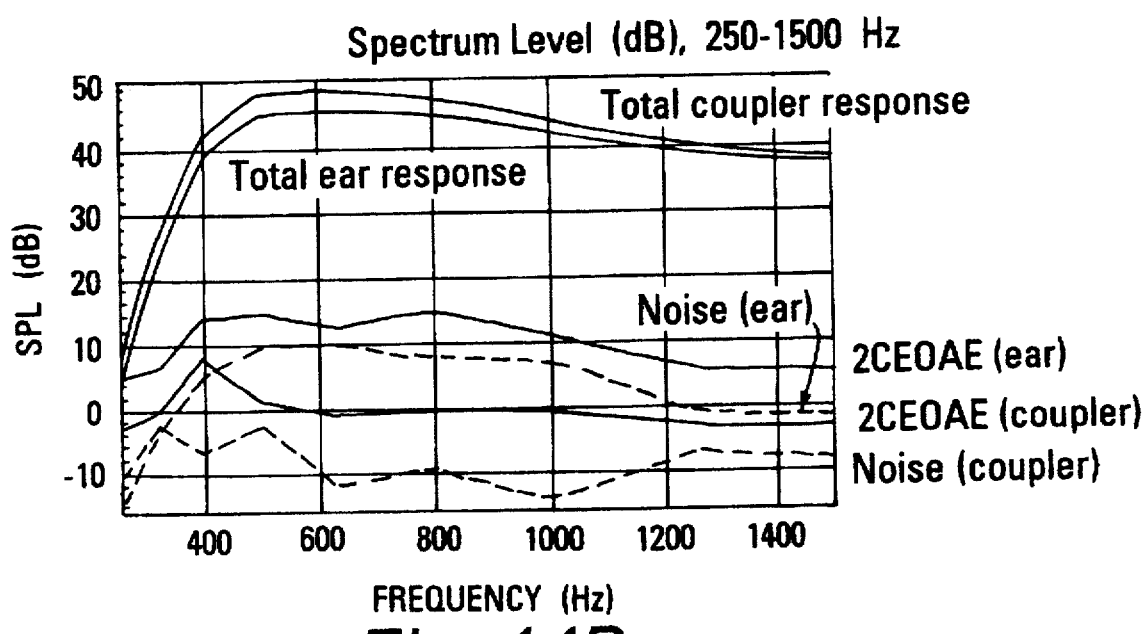

The results in FIGS. 14A and 14B confirm this prediction. The plot of FIG. 14A shows the SPL versus frequency from 250–8000 Hz for six response functions. All response functions are averaged over each ⅓-octave as part of the nonlinear coherence method of noise reduction. The largest-SPL pair (solid lines) are the total responses to the stimulus $s_1(t)$ presented in the ear canal and the 1-cc coupler. The 2CEOAE pair (solid lines) are the total distortion signal measured in the ear canal and the coupler. The noise SPL pair (dashed lines), calculated using the noise autospectrum from the coherence analysis described above, show the random noise in the ear canal and coupler. This representation of the noise level is a contrasting representation of the data to the distortion signal to noise level presented in FIGS. 11A to 11C. The plot of FIG. 14B shows the same six response functions plotted over the low frequency range from 250–1500 Hz.

A valid response in the adult ear was obtained from 250–8000 Hz, because this response exceeds the noise level in the ear in each ⅓-octave and exceeds the deterministic probe distortion in the 2CEOAE coupler response. This coupler response is at least 4 dB above its noise level at all but a single ⅓-octave (near 300 Hz). There is no need for time-gating in calculating this response. The double-source 2CEOAE response is obtained at both higher and lower frequencies than that reported in the prior art for CEOAE responses. The excellent signal-to-noise obtained at low frequencies is due to the elimination of significant amounts of probe distortion, whereas at high frequencies is due to the fact that time-gating was not applied to the CEOAE response, which results in the elimination of the short-latency, high-frequency cochlear responses.

Discussion

This demonstrates the advantage of the techniques provided by system 100. Such advantages are important in clinical applications of click-evoked otoacoustic emission measurement systems, and should be particularly important for testing infants, since the physiologic noise is much higher in infants than adults.

System 100 provides new sets of stimuli that overcome significant drawbacks of the existing technology. The techniques used to reduce probe nonlinearities permit the measurement of short latency responses that could not previously be analyzed. Furthermore, the novel techniques for analyzing nonlinear coherence provide an accurate quantitative measure of random noise and distortion noise. This can provide a stopping criterion for data acquisition such that a specified distortion signal-to-noise ratio is obtained.

C. Non-Real-Time Technique

Artifact rejection can operate along similar lines in a non-real-time implementation. The difference is that all data buffers are acquired and stored in memory. Only those buffers are retained for time averaging that are judged to be valid based upon the relative similarity to a stored buffer of valid data.

5. Nonlinear Transfer Functions of the Ear in Hearing Test Instruments

A. Nonlinear Transfer Functions

The "linear" transfer functions described at the beginning of this application may be extended to the nonlinear regime by measurement of a plurality of acoustic responses in the ear canal at different stimulus levels. Because the term "linear" is no longer appropriate in the context of nonlinearities in the cochlear and middle-ear, the transfer function (impedance, admittance or reflectance) at a given stimulus level is denoted as an iso-level transfer function. Since the system is no longer assumed linear, then the iso-level transfer functions measured at two different stimulus levels are typically unequal. A set of iso-level transfer functions obtained at two or more stimulus levels is termed a nonlinear transfer function. This aspect of the invention concerns the measurement of these nonlinear power-based acoustic response functions in the ear canal in the context of measurement techniques using double-evoking stimuli.

From the plurality of responses at different stimulus levels, it is possible to measure the reflectance in time or frequency domains at various levels to obtain a nonlinear reflectance, and, similarly, to measure the admittance and impedance in time or frequency domains. Any system and method to measure reflectance, admittance or impedance can be used for each iso-level transfer function. By varying stimulus level, a plurality of reflectance, admittance or impedance functions are thereby obtained. The concept of linear transfer function is thus generalized to a nonlinear transfer function.

Four nonlinear, power-based, double-evoked response sets are defined. The first is the plurality of iso-level transfer functions of the ear obtained at various stimulus levels, i.e., the nonlinear transfer function. The second is a differential measurement of any two iso-level transfer functions, obtained by calculating their difference. This differential transfer function is zero for any linear system, and typically non-zero for any nonlinear system. The third is the plurality of responses of iso-level power absorbed by the ear, obtained using any of Equations (3) or (10), or by any substantively equivalent relation. The fourth is the differential absorbed nonlinear power defined below.

The first nonlinear response is well known using single-evoking stimuli in published literature in the case of non-linear impedance (D. Jurzitza and W. Hemmert, "Quantitative measurements of simultaneous evoked otoacoustic emissions," *Acustica* 77:93–99, 1992), and for nonlinear reflectance in (C. A. Shera and G. Zweig, "Noninvasive measurement of the cochlear traveling-wave ratio," *J. Acoust. Soc. Am.* 93:3333–3352, 1993), (J. B. Allen, G. Shaw and B. P. Kimberly, "Characterization of the nonlinear ear canal impedance at low sound levels," *Abstracts of the 18th Midwinter Research Meeting of the ARO*, Association for Research in Otolaryngology, Des Moines, page 190, 1995), and (D. H. Keefe, "Otoreflectance system for linear and nonlinear response measurements of the middle and inner ear," *Abstracts of the 18th Midwinter Research Meeting of the ARO*, Association for Research in Otolaryngology, Des Moines, page 5, 1995). All four nonlinear response sets for single-evoking stimuli are also discussed in this latter reference and (D. H. Keefe, "System and Method for Measuring Acoustic Reflectance," U.S. Patent Application, 1994) for the cases of nonlinear impedance and nonlinear admittance in both time and frequency domains. Single evoking stimuli are those whose stimulus amplitude is varied to obtain a nonlinear response, and which utilize a single signal generator driving a single acoustic source in the ear canal.

In the approach of Shera and Zweig, which is further developed in (G. Zweig and C. A. Shera, "The origin of periodicity in the spectrum of evoked otoacoustic emissions," *J. Acoust. Soc. Am.* 98:2018–2047, 1995), the ear-canal pressure is assumed to have two components, a component that varies slowly with frequency controlled by the middle-ear components of the reflectance and a component that varies more rapidly with frequency that is controlled by the cochlear components of the reflectance. There is no direct measurement of reflectance in the ear canal, but the oscillation of the cochlear reflectance component is identified in its effects on the oscillations with frequency of the ear-canal pressure associated with the evoked otoacoustic emission.

The problem addressed by this invention is the calculation of a nonlinear power-based response using the 2E class of stimuli based upon individual presentations of stimuli $s_1(t)$ and $s_2(t)$, and presentation of $s_{12}(t)=s_1(t)+s_2(t)$. Stimuli are delivered at low to sufficiently moderate sound pressure levels to ensure that the response of the middle ear is linear, except for effects related to the onset of the middle-ear reflex that are controlled for.

While any 2E stimulus set may be used, the double-source embodiment is preferred in which $s_1(t)$ is output by acoustic source 130 and $s_2(t)$ is output by acoustic source 132. In the presentation of $s_{12}(t)$, which is the superposition of $s_1(t)$ and $s_2(t)$, the $s_1(t)$ part of $S_{12}(t)$ is output by acoustic source 130 and the $s_2(t)$ part of $s_{12}(t)$ is output by acoustic source 132. While the structure of $s_1(t)$ and $s_2(t)$ may be artitrary (subject to their having the same duration), the embodiment of Equations (13) and (14) is preferred in which $s_2(t)$ is a time-delayed, rescaled copy of $s_1(t)$. At a finer level of specificity, the preferred embodiment is that there exists no time delay between $s_1(t)$ and $s_2(t)$, i.e., $\tau=0$ in Equation (14).

Techniques exist to measure the iso-level impedance in the cat ear canal in (J. B. Allen, "Measurement of eardrum acoustic impedance," in *Peripheral Auditory Mechanisms*, eds. J. Allen, J. Hall, A. Hubbard, S. Neely and A. Tubis (Springer-Verlag, New York), 1985) and in the human ear canal in (D. H. Keefe, R. Ling and J. C. Bulen, "Method to measure acoustic impedance and reflection coefficient," *J. Acoust. Soc. Am.* 91:470–485, 1992), (D. H. Keefe, J. C. Bulen, K. H. Arehart, and E. M. Burns, "Ear-canal impedance and reflection coefficient in human infants and adults," *J. Acoust. Soc. Am.* 94:2617–2638, 1993), (Keefe, 1994). These techniques use single-microphone measurements of ear-canal pressure and pressure measurements in a set of one or more calibration waveguides. These techniques may be generalized using the 2E stimulus/response framework. For example, both the calibration and ear-canal measurements may be carried out using the same 2E stimulus set $\{(s_1(t), s_2(t), s_{12}(t)\}$ as inputs to the DAC's.

The definition of nonlinear response functions depends upon the choice of the traveling-wave representation via reflectance or the standing-wave representation via impedance or admittance. All nonlinear response functions are defined, beginning with the reflectance representation, and the properties of traveling-wave versus standing-wave representations are then contrasted in the nonlinear regime.

B. Nonlinear Traveling Waves

There exists nonlinearity in both the ear and in the probe assembly (and related instrumentation in the measurement system). For a given electrical stimulus, for example, $s_1(t)$, the probe assembly creates an incident pressure signal $p_i(t, 1)$ propagating away from the probe. A notation is adopted such that the first argument denotes the time or frequency variable, and the second argument denotes the m-th stimulus, where m takes on the values 1, 2 or 12, corresponding to the electrical stimulus $s_1$, $s_2$ or $s_{12}$, respectively. This incident pressure response to electrical stimulus $s_1$ is measured by the microphone in the probe assembly most directly by inserting the probe assembly into a cylindrical waveguide whose cross-sectional area S is the same as, or at least similar to, that of the ear canal to be tested, and whose length is sufficiently long that no reflection from the end of the cylindrical waveguide arrives back at the probe during the duration of the measurement. Alternatively, the incident pressure signal is defined after carrying out the calibration of an arbitrary iso-level reflectance measurement technique by means that are obvious to one skilled in the art.

Transforming to the frequency domain for convenience, the probe assembly is placed in the ear, the electrical stimulus $s_1(f)$ is input to acoustic source 1, and the ear-canal pressure P(f, 1) is measured. It is noted that the ear-canal pressure P(f, 1) is written as $P_1(f)$ elsewhere; the change in notation is useful in the traveling-wave discussion because subscripts denote the incident and reflected components. Similarly, P(f, 2)=$P_2(f)$ and P(f, 12)=$P_{12}(f)$. This measured pressure can be conceptually decomposed using Equation (4) into an incident pressure $P_i(f, 1)$ and reflected pressure $P_r(f, 1)$ by $$P(f, 1) = P_i(f, 1) + P_r(f, 1). \tag{42}$$

The ear-canal reflectance is measured using any convenient iso-level reflectance technique and is denoted as $R_1(f)$ at stimulus level 1, so that the reflected pressure in the ear is calculated using Equation (5), which takes the form $$R_1(f) = \frac{P_r(f, 1)}{P_i(f, 1)}, \tag{43}$$

so that the reflected pressure response to stimulus $s_1$ is $$P_r(f, 1) = R_1(f) P_i(f, 1). \tag{44}$$

The stimulus $s_2(t)$ is input to the probe assembly and its reflected pressure $P_r(f, 2)$ is calculated by the analog to the above equation, i.e., $$P_r(f, 2) = R_2(f) P_i(f, 2). \tag{45}$$

The ear-canal reflectance $R_2(f)$ and incident pressure $P_i(f, 2)$ are those measured by the iso-level reflectance measurement technique using stimulus $s_2$. Finally, the stimulus $s_{12}(t)$ is input to the probe assembly and the reflected pressure $P_r(f, 12)$ is calculated from $$P_r(f, 12) = R_{12}(f) P_i(f, 12). \tag{46}$$

The ear-canal reflectance $R_{12}(f)$ and incident pressure $P_i(f, 12)$ are those measured by the iso-level reflectance measurement technique using stimulus $s_{12}(t)$.

A wide class of iso-level transfer function techniques, substantively all of them, can be considered to have a calibration and evaluation phase. The purpose of the calibration phase is to objectively characterize the equivalent circuit of the one or more source transducers and on or more pressure transducers in the probe assembly. There exist well known acoustic transfer function techniques that use two or more pressure transducers at separate, but specified, locations in the system of interest (the ear canal) or within an external waveguide that is coupled to the ear canal entrance. The transfer functions between each pair of pressure transducers are used with a model of acoustic propagation in the ear canal or external waveguide to calculate the iso-level transfer functions. There also exist acoustic transfer function techniques that use a single pressure transducer in the probe assembly, and for which a number of well-known calibration procedures exist based upon preliminary measurements in a set of one or more calibration waveguides, often a set of one or more cylindrical tubes closed at their far ends. These calibration measurements are often used with a model of acoustic propagation in each of the calibration waveguides to calculate the equivalent circuit parameters. Such models may, or may not, incorporate visothermal losses within each of the calibration waveguides, but the dimensions of each waveguide must be specified for use in the model.

These iso-level transfer functions include iso-level reflectance, impedance and admittance functions. The equivalent circuit of an iso-level reflectance technique includes the incident pressure associated with each of one or more source transducers and the source reflectance of the probe assembly. The equivalent circuit of an iso-level impedance technique includes the Thevenin pressure associated with each of one or more source transducers and the Thevenin impedance of the probe assembly. The equivalent circuit of an iso-level admittance technique includes the Norton volume velocity associated with each of one or more source transducers and the Norton admittance of the probe assembly. Given the particular choice of equivalent circuit parameters associate with the probe assembly consisting of one or more acoustic sources and one or more pressure transducers, the purpose of the evaluation phase is to calculate the desired iso-level transfer function of the ear using the equivalent circuit parameters determined from the calibration phase, and the measured pressure response in the ear canal.

To make the above formal discussion more concrete, the preferred embodiments will be introduced for iso-level measurements of reflectance, impedance and admittance in the frequency domain. The corresponding treatment in the time domain is analogous, although the equivalent circuit parameters may be indirectly represented in the time domain by pressure responses measured in a set of one or more calibration waveguides, as discussed in Keefe (1994) and Keefe, "Wind-instrument reflection function measurements in the time domain", *J. Acoust. Soc. Am.* 99, 2370–2381 (1996). Erratum: *J. Acoust. Soc. Am.* 100, 3985 (1996) (Keefe, 1996).

While any convenient iso-level reflectance technique can be used to measure the three ear-canal reflectances corresponding to stimuli 1, 2, and 12, respectively, the preferred embodiment is the technique in Keefe (1994), Keefe (1995), and Keefe (1996). The additional measurements needed for this technique are described. The 2E stimulus set is delivered in modified form using the probe assembly into a single calibration tube, which in the preferred embodiment is a cylindrical tube with smooth, rigid walls that is closed at its far end. The corresponding 2E response is measured in the calibration tube. The modification to the 2E stimulus set from that used in the ear-canal measurement is required because the response to each of $s_1(t)$ and $s_2(t)$ has much longer duration in the calibration tube than in the ear canal. By appending additional samples with zero values to both $s_1(t)$ and $s_2(t)$, it is ensured that the calibration-tube responses $p_1(t)$ and $p_2(t)$, respectively, completely decay to the level of random noise before the next non-zero stimulus is presented. The single-tube reflectance technique requires only the incident and first-reflected responses from the calibration-tube measurement, which occur at relatively short delays dependent upon the length of the calibration tube and the effective duration of $p_1(t)$ and $p_2(t)$.

The inputs to the calibration step in this reflectance technique are the length and diameter of the calibration tube, a model of acoustic propagation in the tube that includes viscothermal losses, and the measured pressure response in the tube. The length must be sufficiently long so that the incident acoustic response in the tube is separable from the first-reflected acoustic response in the tube, corresponding to propagation from the probe assembly to the closed end and back. The output are the calibration data needed to evaluate the reflectance in the ear canal when the identical probe assembly delivers the identical stimulus. This evaluation step in the reflectance technique further requires the pressure response measured in the ear canal.

This reflectance technique is applied in a three-fold manner (i.e., for stimuli $s_1(t)$, $S_2(t)$ and $s_{12}(t)$) for each pressure response measured in the calibration tube and in the ear canal.

The double-evoked otoacoustic reflected pressure response (2EOR) is defined by analogy with the 2EOAE response by $$\Delta P_r(f) = P_r(f, 12) - [P_r(f, 1) + P_r(f, 2)]. \qquad (47)$$

The 2EOR cannot be calculated from a simple linear combination of ear-canal responses, because it relies on a calibration procedure implicit in any iso-level reflectance technique. Assume, for the moment, that the measurement system has linear response. It follows that the incident pressure is strictly proportional to the stimulus amplitude so that $$\frac{P_i(f, 1)}{P_i(f, 12)} = \frac{S_1(f)}{S_1(f) + S_2(f)}, \qquad (48)$$

$$\frac{P_i(f, 2)}{P_i(f, 12)} = \frac{S_2(f)}{S_1(f) + S_2(f)}.$$

The nonlinear part of the total pressure in the ear canal would then be determined by the nonlinear part of the reflected pressure alone, which follows from the above equation and Equation (49):

$$\Delta_0 P_r(f) = P_i(f, 12) \left\{ \begin{array}{l} [R_{12}(f) - R_1(f)] \frac{S_1(f)}{S_1(f) + S_2(f)} + \\ [R_{12}(f) - R_2(f)] \frac{S_2(f)}{S_1(f) + S_2(f)} \end{array} \right\}. \qquad (49)$$

The subscript 0 on $\Delta P_r(f)$ denotes the form of $\Delta P_r(f)$ under the assumption that the measurement system is linear.

The nonlinear change in the reflected pressure is proportional to the nonlinear change in reflectance; $\Delta_o P_r(f)=0$ if the ear response is also linear. If this assumption were valid that the measurement system response is linear, there would be no advantage in using the set of three stimuli $\{s_1, S_2, S_{12}\}$ as compared to a set of two identical stimulus waveforms delivered at different stimulus levels, as utilized by Jurzitza and Hemmert (1992), Keefe (1994), Keefe (1995) and Allen et al. (1995) for various power-based response functions. This can be seen by setting $S_2(f)=S_1(f)$, so that the corresponding iso-level reflectances are equal, $R_1=R_2$ (actually, the mean of these two reflectances is the optimal estimate in the presence of random measurement noise), and the above equation simplifies to $$\Delta_o P_r(f) = P_i(f, 12)[R_{12}(f) - R_1(f)]. \qquad (50)$$

This would be the differential nonlinear reflectance measured using two stimulus levels using an ideal measurement system.

The advantage of the present invention comes when there exists nonlinear distortion in the measurement system, so that neither is the incident pressure strictly proportional to the stimulus level, nor is the nonlinear part of the total ear-canal pressure due solely to the nonlinear part of the reflected pressure. Nevertheless, the iso-level transfer functions in Equations (44) to (46) remains valid in this more realistic case; these are combined to calculate the 2EOR in Equation (47). However, Equations (48) to (50) are no longer valid.

In the preferred double-source embodiment, any probe distortion produced independently by acoustic source 1 or acoustic source 2 is canceled in the 2EOR, so that the deterministic nonlinear response is due only to the reflected response of the ear. This is an important new property associated with the utilization of the 2E stimulus sequence in measurements of nonlinear evoked reflectance. The word "emission" is avoided because the representation is explicitly in terms of a reflected cochlear signal.

The interpretation of the 2EOR depends on the specific choice of $s_1$ and $s_2$. The preferred embodiment defines $s_2(t)$ to be a duplicate of $s_1(t)$ re-scaled in amplitude by $\epsilon$:

$$s_2(t) = \epsilon s_1(t), \qquad (51)$$

The value of $\epsilon$ is an arbitrary positive or negative number. The stimulus waveform $s_1(t)$ may be chosen to be a wideband transient signal whose overall duration is constrained to be less than the duration of the N-sample window. Particular choices of $S_1(t)$, and thus $s_2(t)$, include a click, defined as an electrical signal whose duration is much shorter than the impulse response of the acoustic source, or a chirp. If a chirp is used, created by applying time-stretching via an allpass filter to an original stimulus signal of short duration, then each pressure response may be time-compressed, if desired, using the inverse allpass filter so that the resulting signals are again of short duration. This is described in Keefe, 1996.

A pressure reflectance may be defined as the ratio of the 2EOR pressure response to the incident pressure at a reference stimulus level. This reference stimulus is taken to be $s_{12}(t)$, although alternative embodiments are straightforward to define at reference stimulus levels of $s_1$ or $s_2$. This reflectance is called the nonlinear otoreflectance (ORN), and is denoted by $\Delta R(f)$. It is defined in the standard traveling-wave representation as the ratio of the nonlinear reflected pressure to the incident pressure by $$\Delta P_r(f) = P_i(f, 12)\Delta R(f) \tag{52}$$

and is calculated using Equations (44) through (47) by $$\Delta R(f) = \left[\frac{1}{1+\epsilon} R_{12}(f) - \frac{P_i(f, 1)}{P_i(f, 12)} R_1(f)\right] + \left[\frac{\epsilon}{1+\epsilon} R_{12}(f) - \frac{P_i(f, 2)}{P_i(f, 12)} R_2(f)\right]. \tag{53}$$

The corresponding linear otoreflectance (ORL) is the iso-level pressure reflectance $R_{12}(f)$ measured using the stimulus $s_{12}$.

The nonlinear otoreflectance is a complex quantity $|\Delta R(f)|e^{-j\Delta\Phi(f)}$ whose phase $-\Delta\Phi(f)$ contains information on the nonlinear phase change in reflectance, which might be expressed as a group or phase delay, or related function. The nonlinear reflected power $\Delta\Pi_r(f, 12)$ may be defined as $$\Delta\Pi_r(f, 12) = \Pi_i(f, 12)|\Delta R(f)|^2, \tag{54}$$

which may be compared to the iso-level reflected power at stimulus level $s_{12}$ (see Equation (9)):

$$\Delta\Pi_r(f, 12) = \Pi_i(f, 12)|R_{12}(f)|^2. \tag{55}$$

In practice, the two acoustic sources may be chosen to have similar sensitivities and similar overload characteristics. Similar sensitivities means that an electrical input signal of unit amplitude produces outputs from the two sources that are similar in level. Similar overload means that the peak overload levels of the sources are also similar. Differences in sensitivities can be accounted for in terms of relative calibration of stimulus levels, such that the relative acoustic levels of the signals output in the ar canal can be accurately specified, if desired. Even small differences in peak overload levels, or other nonlinear response characteristics of the sources, may be quite important in measuring the nonlinear response of the ear, because this signal is also small.

With this preliminary discussion, two ranges of values for the gain $\epsilon$ of source 2 relative to source 1 are of particular interest:

(i) $\epsilon=1$, and, (ii) $\epsilon<<1$.

For case (i), the acoustic outputs from sources with similar sensitivities, taken without loss of generality to be equal sensitivities after suitable calibration, are equal, except for differences in distortion produced. When $s_{12}(t)$ is applied, the acoustic signal in the ear canal is approximately doubled in amplitude, corresponding to a change in SPL of 6 dB. Since $s_1(t)$ and $s_2(t)$ are substantively identical, then $R_1$ and $R_2$ are substantively independent measurements of the same iso-level reflectance $R_<$ (the subscript $<$ denotes the reflectance measured at the lower level), which is calculated as the mean value:

$$R_<(f) = \frac{P_i(f, 1)}{P_i(f, 12)} R_1(f) + \frac{P_i(f, 2)}{P_i(f, 12)} R_2(f) \tag{56}$$

The nonlinear otoreflectance in Equation (53) simplifies to $$\Delta R(f) = R_{12}(f) - R_<(f). \tag{57}$$

In practice, the reflectance is nearly linear at relatively high stimulus levels, so that it is convenient to rewrite the above for the reflectance at the lower stimulus level in terms of the reflectance at the higher stimulus level $R_>=R_{12}$, so that $$R_<(f) = R_>(f) - \Delta R(f). \tag{58}$$

In case (ii), the relative gain $\epsilon$ is chosen to be much smaller than unity, so the acoustic source 2 outputs the same waveform as acoustic source 1, but at much lower level. This configuration is convenient for measuring the differential, i.e., nonlinear otoreflectance with extremely low distortion. The baseline measurement level is varied by varying the level of $s_1$. Acoustic source 1 may be operating at an excitation level for which its distortion is significant. If its amplitude were changed from 1 to $(1+\epsilon)$, its distortion would be increased. In contrast, the use of two sources means that the distortion of acoustic source 1 is maintained at a fixed level, and it is acoustic source 2 that contributes the differential increase in gain. The double-evoked subtraction technique controls for distortion in the nonlinear otoreflectance measurement by use of the double-source embodiment.

This is a differential power-based measurement, because the nonlinear increment of power is measured relative to the baseline amplitude of $s_1(t)$, which can be varied over a fairly broad range, e.g., in 10 dB increments. For example, choosing the amplitude ratio $\epsilon=0.1$, corresponding to an $s_2$ amplitude that is $-20$ dB lower than the $s_1$ amplitude, allows an iso-level measurement of power response at the $s_1$ amplitude level and the differential measurement of power response in the neighborhood of this level.

C. Nonlinear Standing Waves

The separation of the acoustic quantities into incident and reflected signals is lost in a standing-wave representation, but the measurement of nonlinear admittance and impedance remains well defined.

The double-evoking (2E) stimulus set $\{s_1, s_2, s_{12}\}$ is used to collect the respective set of pressure responses $\{P(f, 1), P(f, 2), P(f, 12)\}$ in the ear, and is also used to calibrate the iso-level admittance or impedance measurement system for each of the three stimuli. The double-source embodiment is preferred. The preferred embodiment of the choice of stimulus set is the same as for nonlinear reflectance, i.e., one chooses $s_2(t)=\epsilon s_1(t)$, with $\epsilon=1$ or $\epsilon<<1$. In case (i) with $\epsilon=1$, the measurement of $Y_1(f)$ using $s_1$, and $Y_2(f)$ using $s_2=s_1$, result in two measurements of the same admittance. Its value $Y_<(f)$ is calculated from weighted average of the total ear-canal pressure response $P(f, 1)$ to stimulus 1, and the total ear-canal pressure response $P(f, 2)$ to stimulus 2, by $$Y_<(f) = \frac{P(f, 1)}{P(f, 12)} Y_1(f) + \frac{P(f, 2)}{P(f, 12)} Y_2(f). \tag{59}$$

The approximation becomes an equality in the limit that the probe distortion is small.

The total volume velocity $U_m(f)$ for the m-th stimulus condition is related to the admittance and pressure for the m-th stimulus condition by $$U(f, m) = P(f, m)Y_m(f). \tag{60}$$

Applying the double-evoked subtraction to the volume velocity results in the nonlinear distortion component of volume velocity $U_D(f)$, which is defined by $$\begin{aligned} U_D(f) &= U_{12}(f) - [U_1(f) + U_2(f)] \\ &= P(f, 12)Y_{12}(f) - [P(f, 1)Y_1(f) + P(f, 2)Y_2(f)] \\ &= P(f, 12) [Y_{12}(f) - Y_<(f)]. \end{aligned} \tag{61}$$

The associated nonlinear admittance $\Delta Y(f)$ is defined by $$\Delta Y(f) = \frac{U_D(f)}{P(f,12)} = Y_{12}(f) - Y_<(f). \tag{62}$$

To measure nonlinear impedance in an experiment with $\epsilon=1$, a parallel analysis gives $$\begin{aligned} P_D(f) &= P_{12}(f) - [P_1(f) + P_2(f)] \\ &= U(f,12)Z_{12}(f) - [U(f,1)Z_1(f) + U(f,2)Z_2(f)] \\ &= U(f,12)[Z_{12}(f) - Z_<(f)], \end{aligned} \tag{63}$$

where the weighted mean of the impedance $Z_<(f)$ at the stimulus level $S_1 = S_2$ is $$Z_<(f) = \frac{U(f,1)}{U(f,12)} Z_1(f) + \frac{U(f,2)}{U(f,12)} Z_2(f). \tag{64}$$

Thus, the associated nonlinear impedance $\Delta Z$ is $$\Delta Z(f) = \frac{P_D(f)}{U(f,12)} = Z_{12}(f) - Z_<(f). \tag{65}$$

The use of two acoustic sources and the double-evoked subtraction results in a nonlinear admittance or impedance that is independent of the probe distortion separately produced by each source. This is in contrast to the single-source method of measuring nonlinear admittance or impedance, which is contaminated by probe distortion. As with nonlinear reflectance (see Equation (58)) for the case $\epsilon=1$, the best manner to represent the nonlinear admittance or impedance is to denote the responses measured at the higher stimulus level by $Y_> = Y_{12}$ and $Z_> = Z_{12}$ so that the responses at the lower stimulus level are written as:

$$Y_<(f) = Y_>(f) - \Delta Y(f),$$

$$Z_<(f) = Z_>(f) - \Delta Z(f). \tag{66}$$

The analysis of case (ii) such that $\epsilon \ll 1$ for admittance and impedance proceeds in a parallel manner to that for reflectance. This choice of relative gain provides a differential measurement of nonlinear admittance or nonlinear impedance in a manner.

While any convenient iso-level impedance or admittance technique can be used to measure the three ear-canal impedances (or admittances) corresponding to stimuli 1, 2, and 12, respectively, the preferred embodiment is the technique in Keefe (1994), Keefe (1995), and Keefe (1996). The additional measurements needed for this technique are identical to those described above for the preferred embodiment of the iso-level reflectance technique. The only difference is that reflectance calibration measurements in the calibration tube and reflectance evaluation measurements in the ear canal must be converted into impedance (or admittance) calibration and evaluation measurements, respectively. This conversion is straightforward based upon relationships between traveling-wave and standing-wave descriptions of acoustic waves given in Keefe (1994) and Keefe (1996).

Before introducing the double-evoked subtraction procedure for calculating the power absorbed by the ear, the relationship of stimulus level to absorbed power is discussed. For example, assume that the acoustic ear-canal response is measured under two conditions, one with an electrical input to the acoustic source transducer of unit amplitude leading to a pressure response $P(f)$, and the other with an electrical input of amplitude $A$ leading to a pressure response $AP(f)$. The corresponding power absorbed in the linear system is denoted $\Pi_a(f,A)$ at frequency $f$ and stimulus amplitude $A$. The two experiments lead to the following absorbed power measurements:

$$\Pi_a(f,1) = \frac{1}{2} G|P(f)|^2, \tag{67}$$

$$\Pi_a(f,A) = \frac{1}{2} GA^2|P(f)|^2.$$

It follows that $$\Pi_a(f,A) = A^2 \Pi_a(f,1) \tag{68}$$

The stimulus-weighted power difference $\Delta\Pi a(f)$ defined by $$\Delta\Pi_a(f) = \Pi_a(f,A) - A^2\Pi_a(f,1), \tag{69}$$

has the property that it is identically zero for any idealized linear system, so that it is a measure of nonlinear power absorption.

The standing-wave representation is convenient because of the simple expressions for absorbed power. These iso-level expressions using Equation (3) are given below in terms of the iso-level conductance $G_m$ at the m-th level for the three stimulus levels:

$$\pi_a(f,1) = \frac{1}{2} G_1(f)|P(f,1)|^2 \tag{70}$$

$$\pi_a(f,2) = \frac{1}{2} G_2(f)|P(f,2)|^2$$

$$\pi_a(f,12) = \frac{1}{2} G_{12}(f)|P(f,12)|^2.$$

The usual double-evoked subtraction rule applied to power would be to form the difference, $\Pi_a(f,12) - [\Pi_a(f,1) + \Pi_a(f,2)]$, but this does not sum to zero for an ideal linear system. Assume that the measurement system has no distortion. By analogy with Equation (69), the nonlinear absorbed power is defined by $$\Delta_0\Pi_a(f) = \Pi_a(f,12) - \left( \left| \frac{S_{12}(f)}{S_1(f)} \right|^2 \Pi_a(f,1) + \left| \frac{S_{12}(f)}{S_2(f)} \right|^2 \Pi_a(f,2) \right). \tag{71}$$

For the preferred embodiment with $S_2(f) = \epsilon S_1(f)$, the above simplifies to $$\Delta_0\Pi_a(f) = \Pi_a(f,12) - \left( \left| \frac{1+\epsilon}{1} \right|^2 \Pi_a(f,1) + \left| \frac{1+\epsilon}{\epsilon} \right|^2 \Pi_a(f,2) \right). \tag{72}$$

In the presence of measurement-system distortion, the double-evoked nonlinear power $\epsilon\Pi_a(f)$ is defined by $$\Delta\Pi_a(f) = \Pi_a(f,12) - \left( \left| \frac{P(f,12)}{P(f,1)} \right|^2 \Pi_a(f,1) + \left| \frac{P(f,2)}{P(f,12)} \right|^2 \Pi_a(f,2) \right). \tag{73}$$

Consider case (i) such that $\epsilon = 1$. Then, the levels of $S_1(f)$ and $S_2(f)$ are equal (for equal source sensitivities, as is assumed without loss of generality), and the pair of calculations of absorbed power, $\Delta\Pi_a(f,1)$ and $\Delta\Pi_a(f,2)$ are independent estimates of the low-stimulus-level power $\Delta\Pi_a(f,<)$. As described above, case (ii) with $\epsilon \ll 1$ leads to a nonlinear differential measure, in the present example, of power absorption.

The specific value of $\epsilon$ may be adjusted sufficiently small in value to reduce probe distortion to acceptable levels, but sufficiently large in value that the differential measurement of pressure exceeds the pressure amplitude associated with sources of noise. In particular, it may be useful to choose $s_2(t) = \epsilon s_1(t-\tau)$, that is, delayed in time by $\tau$ in the range 0–10 msec in addition to the re-scaling in amplitude by $\epsilon$. It is also possible to consider stimulus sets of three or more stimuli, as long as the corresponding distortion pressure response is obtained by subtracting out the linear response of the system such that the signal in each acoustic source used is substantively iso-level.

Both linear and nonlinear response functions can be measured at various levels of static pressure in the ear. The probe assembly may include an additional port to control changes in the static pressure of the ear canal. The nonlinear, acoustic power-based response in the ear canal is measured using two acoustic sources as a function of changes in static pressure over the range employed in tympanometry. For example, the admittance can be measured as a function of frequency and static pressure, and operationally defined in the iso-level regime as well as the nonlinear regime. Such data may be useful in assessing the interaction between conductive and cochlear impairments.

The present system uses a probe assembly with one or more sound sources and one microphone. Well-known techniques exist to measure the acoustic transfer function of an unknown termination using two or more microphones, where the transfer function is calculated in terms of the cross-spectrum between pairs of microphones and knowledge of the transmission characteristics of the waveguide between each pair of microphone positions. The waveguide can be the ear canal or an external tube of known geometry (for example, cylindrical or conical) that is coupled to the ear canal.

The present double-evoked stimulus/response technique is applied using a system that measures the transfer function and nonlinear absorbed power. It can be appreciated that the transfer function measured at each stimulus level can be measured using a probe with two or more microphones using the technique summarized in the previous paragraph, and that a double-evoked nonlinear transfer function can thereby be obtained. such generalizations are within the scope of the present invention.

D. Clinical Applications

Such iso-level power-based responses as impedance, admittance and reflectance have proven to be useful for the screening, detection and diagnosis of hearing problems related to middle-ear pathology. It can be appreciated that measurement of both the iso-level and nonlinear power-based responses combining impedance, admittance and reflectance responses with nonlinear reflected pressure responses may be useful in areas related to the screening, detection and diagnosis of hearing problems related to both middle and inner ear pathologies.

While the invention has been shown and described in connection with various embodiments thereof, it is apparent that many modifications, additions and substitutions may be made which are within the scope of the appended claims.

I claim:

1. A system for the generation of a double-evoking otoacoustic emission stimulus signal in an ear canal and the measurement of the resulting double-evoked otoacoustic emission, comprising, a signal generator operative to generate a double-evoking stimulus set comprising a first stimulus signal having a first arbitrary waveform, a second stimulus signal having a second arbitrary waveform having the same duration as the first arbitrary waveform, and a third stimulus signal which is the superposition combination of the first and second stimulus signals, the output of said signal generator being first, second and third electrical stimulus signals corresponding to said first, second and third stimulus signals, a probe assembly insertable into the ear canal, said probe assembly including a single source transducer coupled to the signal generator to receive the first, second and third electrical stimulus signals and operative to emit into an ear canal a double-evoking acoustic stimulus set including first, second and third acoustic signals corresponding to said first, second and third electrical stimulus signals, thereby to stimulate in the ear canal a double-evoked acoustic pressure response set including first, second and third acoustic pressure responses to said first, second and third acoustic signals respectively, said probe assembly including an acoustic pressure transducer insertable into the ear canal and operative to detect and convert said double-evoked acoustic pressure response set to a double-evoked electrical response set including first, second and third electrical response signals corresponding to said first, second and third acoustic pressure responses, and a processor coupled to the acoustic pressure transducer to receive the double-evoked electrical response set and operative to determine therefrom an evoked cochlear response to the double-evoking acoustic stimulus set, the double-evoked electrical response set including a linear portion and a nonlinear portion called the double-evoked otoacoustic emission, said processor being operative to subtract the first electrical response signal and the second electrical response signal from the third electrical response signal to substantially eliminate said linear portion.

2. The system of claim 1 wherein said second arbitrary waveform is substantially identical to said first arbitrary waveform except that it is delayed in time and scaled in amplitude.

3. The system of claim 2 wherein said delay time ranges from 0 to 10 milliseconds.

4. The system of claim 2 wherein double-evoked electrical response set is a double-evoked electric click response set and the first and second stimulus signals are first and second click signals.

5. The system of claim 1 wherein said first and second waveforms are identical.

6. The system of claim 1 wherein the signal generator includes a digital-to-analog converter to generate said double-evoking stimulus set.

7. The system of claim 1 wherein said acoustic pressure transducer is a microphone contained within said probe assembly.

8. The system of claim 1 wherein said double-evoking stimulus set comprises an arbitrary number, more than two, of stimulus signals, each having an arbitrary waveform, and the various superposition combinations of those stimulus signals having the same duration.

9. The system of claim 8 comprising said arbitrary number, more than one, of source transducers in said probe assembly.

10. The system of claim 1 in which the first and second stimulus signals are first and second chirp signals, respectively, the first chirp signal having a first group delay, and the second chirp signal having a second group delay, the first and second group delays having a predetermined relationship.

11. The system of claim 10 in which said second chirp signal is substantially identical to said first chirp signal, but delayed in time and scaled in amplitude.

12. The system of claim 11 in which the first and second chirp signals are linear chirp signals with the first and second group delays each being a linear function of frequency.

13. The system of claim 11 in which the first and second chirp signals are logarithmic chirp signals with the first and second group delays each being a logarithmic function of frequency.

14. The system of claim 11 in which the first chirp signal is related to the second chirp signal such that each frequency of the second chirp signal at each given point in time is a fixed multiple of each respective frequency of the first chirp signal at the given point in time.

15. The system of claim 11 wherein said acoustic pressure transducer is operative to convert said double-evoked acoustic pressure response set to a double-evoked electrical chirp response set, and further comprising an inverse allpass filter operatively associated with said processor to convert the double-evoked electrical chirp response set into a dechirped electrical response set including first, second and third dechirped electrical response signals indicative of a dechirped cochlear response.

16. The system of claim 1 further comprising a pump coupled to said probe assembly to control statis pressure in the ear, said computer processor determining said evoked cochlear response at an arbitrary value of static pressure in the ear.

17. A system for the generation of a double-evoking otoacoustic emission stimulus signal in an ear canal and the measurement of the resulting double-evoked otoacoustic emission, comprising, a signal generator operative to simultaneously generate two stimulus sets:

a first double-evoking stimulus set comprising a first stimulus signal $s_1(t)$ having a first arbitrary waveform, a zero values signal having the same duration as $s_1(t)$, and $s_1(t)$, and a second double-evoking stimulus set comprising a zero values signal having the same duration as $s_1(t)$, a second stimulus signal $s_2(t)$ having a second arbitrary waveform having the same duration as $s_1(t)$, and $S_2(t)$, the output of said signal generator being first and second electrical stimulus sets, said first electrical stimulus set including first, second and third electrical stimulus signals corresponding to the three signals of said first double-evoking stimulus set, and said second electrical stimulus set including fourth, fifth and sixth electrical stimulus signals corresponding to the three signals of said second double-evoking stimulus set, a probe assembly insertable into the ear canal, said probe assembly including first and second acoustic source transducers, the first source transducer being coupled to the signal generator to receive the first, second and third electrical stimulus signals and operative to emit into an ear canal a first double-evoking acoustic stimulus set including first, second and third acoustic signals corresponding to said first, second and third electrical stimulus signals, and the second source transducer being coupled to the signal generator to receive the fourth, fifth and sixth electrical stimulus signals and being operative to emit into the ear canal a second double-evoking acoustic stimulus set including fourth, fifth and sixth acoustic signals corresponding to said fourth, fifth and sixth electrical stimulus signals, thereby to stimulate in the ear canal a double-evoked acoustic pressure response set including first, second and third acoustic pressure responses to the summation in the ear canal of said first and second double-evoking acoustic stimulus sets, said probe assembly including an acoustic pressure transducer insertable into the ear canal and operative to detect and convert said double-evoked acoustic pressure response set to a double-evoked electrical response set including first, second and third electrical response signals corresponding to said first, second and third acoustic pressure responses, and a processor coupled to the acoustic pressure transducer to receive the double-evoked electrical response set and operative to determine therefrom an evoked cochlear response to the double-evoking acoustic stimulus set, the double-evoked electrical response set including a linear portion and a nonlinear portion called the double-evoked otoacoustic emission, said processor being operative to subtract the first electrical response signal and the second electrical response signal from the third electrical response signal to substantially eliminate said linear portion.

18. The system of claim 17 wherein said second arbitrary waveform is substantially identical to said first arbitrary waveform except that it is delayed in time and scaled in amplitude.

19. The system of claim 18 wherein said delay time ranges from 0 to 10 milliseconds.

20. The system of claim 17 wherein said first and second waveforms are identical.

21. The system of claim 17 wherein the signal generator includes first and second digital-to-analog converters to generate the first and second electrical stimulus sets, respectively.

22. The system of claim 17 wherein said acoustic pressure transducer is a microphone.

23. The system of claim 17 wherein said first and second double-evoking stimulus sets comprise an arbitrary number, more than two, of stimulus signals, each having an arbitrary waveform, and the various superposition combinations of those stimulus signals, under the constraint that the arbitrary number of stimulus signals are of equal duration.

24. The system of claim 23 comprising said arbitrary number of source transducers in said probe assembly.

25. The system of claim 17 in which the first and second stimulus signals are first and second chirp signals, respectively, the first chirp having a first predetermined group delay, and the second chirp having a second predetermined group delay, the first and second group delays having a predetermined relationship.

26. The system of claim 25 in which said second chirp signal is substantially identical to said first chirp signal, but delayed in time and scaled in amplitude.

27. The system of claim 26 in which the first and second chirp signals are linear chirp signals with the first and second group delays each being a linear function of frequency.

28. The system of claim 26 in which the first and second chirp signals are logarithmic chirp signals with the first and second group delays each being a logarithmic function of frequency.

29. The system of claim 26 in which the first chirp signal is related to the second chirp signal such that each frequency of the second chirp signal at a given point in time is a fixed multiple of each frequency of the first chirp signal at the given point in time.

30. The system of claim 26, further including an inverse allpass filter within the processor to convert the electrical chirp response signal into a dechirped electrical response signal indicative of a dechirped cochlear response.

31. The system of claim 17 in which the first and second stimulus signals are first and second click signals, respectively.

32. The system of claim 17 further comprising a pump coupled to said probed assembly to control static pressure in the ear, said computer processor determining said double-evoked otoacoustic emission at an arbitrary value of static pressure in the ear.

33. A system for the measurement of a nonlinear coherence function for a double-evoked response for use in formulating the criteria to determine when a sufficient number of responses have been acquired, the system comprising:

a signal generator operative to generate a double-evoking stimulus set comprising a first stimulus signal having a first arbitrary waveform, a second stimulus signal having a second arbitrary waveform having the same duration as the first arbitrary waveform, and a third stimulus signal which is the superposition combination of the first and second stimulus signals, the output of said signal generator being first, second and third electrical input signals corresponding to said first, second and third stimulus signals, a probe assembly insertable into the ear canal, said probe assembly including a single source transducer coupled to the signal generator to receive the first, second and third electrical input signals and operative to emit into an ear canal a double-evoking acoustic stimulus set including first, second and third acoustic signals corresponding to said first, second and third electrical input signals, thereby to stimulate in the ear canal a double-evoked acoustic pressure response set including first, second and third acoustic pressure responses to said first, second and third acoustic signals respectively, said probe assembly including an acoustic pressure transducer insertable into the ear canal and operative to detect and convert said double-evoked acoustic pressure response set to a double-evoked electrical response set including first, second and third electrical response signals corresponding to said first, second and third acoustic pressure responses, and a processor coupled to the acoustic pressure transducer to receive the double-evoked electrical response set and operative to determine therefrom an evoked cochlear response to the double-evoking acoustic stimulus set, the double-evoked electrical response set including a linear portion and a nonlinear portion called the double-evoked response, said processor being operative to subtract the first electrical response signal and the second electrical response signal from the third electrical response signal to substantially eliminate said linear portion, said nonlinear portion comprising a distortion signal, a spectral analyzer to receive a first input signal comprised of one of said first, second and third electrical stimulus signals and a second input signal comprised of said distortion signal, and being operative to calculate a first autospectrum of the first input signal, a second autospectrum of the second input signal, and a cross-spectrum of the first and second input signals, said spectral analyzer being operative to calculate a nonlinear coherence as a function of frequency as the ratio of the squared magnitude of said cross-spectrum to the product of said first and second autospectra.

34. The system of claim 33 further comprising a processor operatively associated with said spectral analyzer for calculating a nonlinear signal-to-noise ratio in terms of nonlinear coherence.

35. A system for the measurement of a nonlinear coherence function for a double-evoked response for use in formulating the criteria to determine when to conclude data acquisition, the system comprising, a signal generator operative to simultaneously generate:

a first double-evoking stimulus set comprising a first stimulus signal $s_1(t)$ having a first arbitrary waveform, a zero values signal having the same duration as $s_1(t)$, and $s_1(t)$, and a second double-evoking stimulus set comprising said zero values signal, a second stimulus signal $s_2(t)$ having a second arbitrary waveform having the same duration as $s_1(t)$, and $s_2(t)$, the output of said signal generator being first and second electrical stimulus sets, said first electrical stimulus set including first, second and third electrical stimulus signals corresponding to the three signals of said first double-evoking stimulus set, and said second electrical stimulus set including fourth, fifth and sixth electrical stimulus signals corresponding to the three signals of said second double-evoking stimulus set, a probe assembly insertable into the ear canal, said probe assembly including first and second acoustic source transducers, the first source transducer being coupled to the signal generator to receive the first, second and third electrical stimulus signals and operative to emit into an ear canal a first double-evoking acoustic stimulus set including first, second and third acoustic signals corresponding to said first, second and third electrical stimulus signals, and the second source transducer being coupled to the signal generator to receive the fourth, fifth and sixth electrical stimulus signals and being operative to emit into the ear canal a second double-evoking acoustic stimulus set including fourth, fifth and sixth acoustic signals corresponding to said fourth, fifth and sixth electrical stimulus signals, thereby to stimulate in the ear canal a double-evoked acoustic pressure response set including first, second and third acoustic pressure responses to the summation in the ear canal of said first and second double-evoking acoustic stimulus sets, said probe assembly including an acoustic pressure transducer insertable into the ear canal and operative to detect and convert said double-evoked acoustic pressure response set to a double-evoked electrical response set including first, second and third electrical response signals corresponding to said first, second and third acoustic pressure responses, and a processor coupled to the acoustic pressure transducer to receive the double-evoked electrical response set and operative to determine therefrom an evoked cochlear response to the double-evoking acoustic stimulus set, the double-evoked electrical response set including a linear portion and a nonlinear portion called the double-evoked response, said processor being operative to subtract the first electrical response signal and the second electrical response signal from the third electrical response signal to substantially eliminate said linear portion, said nonlinear portion comprising a distortion signal, a spectral analyzer to receive a first input signal comprised of one of said first, second and third electrical stimulus signals and a second input signal comprised of said distortion signal, and being operative to calculate a first autospectrum of the first input signal, a second autospectrum of the second input signal, and a cross-spectrum of the first and second input signals, said spectral analyzer being operative to calculate a nonlinear coherence as a function of frequency as the ratio of the squared magnitude of said cross-spectrum to the product of said first and second autospectra.

36. The system of claim 35 further comprising a processor operatively associated with said spectral analyzer for calculating a nonlinear signal-to-noise ratio in terms of nonlinear coherence.

37. A method for measuring an acoustic pressure response in an ear canal using an artifact rejection technique for eliminating exceptionally noisy data, comprising emitting repetitive acoustic stimulus signals into an ear canal, thereby stimulating repetitive acoustic pressure responses in the ear canal, detecting and transducing said repetitive acoustic pressure responses to repetitive detected electrical response signals, converting said repetitive detected electrical response signals to repetitive digital electrical response signals forming a second vector of responses, obtaining a first vector of responses representative of the response of the ear in the presence of relatively low background noise, entering said first vector of responses into a first buffer, entering said second vector of responses into a second buffer, calculating the current degree of similarity of the vectors of responses in the first and second buffers, and classifying said second vector of responses into one of two categories, valid and invalid.

38. The method of claim 37 wherein said classifying step comprises establishing a threshold degree of similarity, discarding the second vector of responses upon the current degree of similarity being less than said threshold degree of similarity, and transmitting to a response averager the second vector of responses upon the current degree of similarity being greater than or equal to said threshold degree of similarity.

39. The method of claim 37 wherein data acquisition is begun by entering a first obtained current vector of responses into one of said first and second buffers and entering a second obtained current vector of responses into the other of said first and second buffer.

40. The method of claim 37 wherein said first vector of responses comprises the last saved second vector of responses classified as valid.

41. The method of claim 37 wherein the step of calculating the current degree of similarity comprises calculating the norm of the difference of the first and second vectors of responses.

42. The method of claim 37 wherein said classifying step comprises assigning a probability function for response validity that varies with the measure of relative similarity, thereby providing a stochastic classification rule weighted by the assigned probability function.

43. The method of claim 37 further comprising discarding both the first and second vectors of responses upon classifying said second vector of responses into the invalid category.

44. The method of claim 37 wherein the step of obtaining a first vector of responses comprises calculating a first vector of responses as a function of a plurality of second vectors of responses that were previously classified in the valid category.

45. The method of claim 44 wherein the step of calculating a first vector of responses comprises calculating a running average as the running sum of said plurality of second vectors divided by the number of said plurality of second vectors.

46. The method of claim 45 wherein the step of calculating a first vector of responses comprises calculating a time-weighted average in which the most recently classified valid second vectors of responses are more highly weighted than less recently classified valid second vectors of responses.

47. The method of claim 37 wherein said classifying step comprises selecting a classification parameter and classifying said second vector of responses according to said classification parameter, which may be varied during the operation of the artifact rejection technique.

48. The method of claim 47 wherein said classifying step comprises adjusting said threshold degree of similarity during the operation of the artifact rejection technique and classifying said second vector of responses according to said threshold, thereby controlling for a) variability between subjects in physiologic and other noise, b) state-dependent physiologic changes during data acquisition on a particular subject, and c) the degree of recency to use.

49. The method of claim 37 in which the repetitive acoustic pressure responses measured in the ear are used in a system to measure evoked otoacoustic emissions.

50. The method of claim 37 in which the repetitive acoustic pressure responses measured in the ear are used in a system to measure iso-level transfer functions of the ear.

51. The method of claim 37 in which the repetitive acoustic pressure responses measured in the ear are used in a system to measure nonlinear transfer functions.

52. The method of claim 37 in which the repetitive acoustic pressure responses measured in the ear are used in a system to measure auditory brainstem responses.

53. The system of claim 37 in which the repetitive acoustic pressure responses measured in the ear are used in a system to measure tympanograms.

54. The method of claim 37 wherein said entering steps and said calculating and classifying steps are performed in real time during data acquisition.

55. The method of claim 37 wherein said entering steps and said calculating and classifying steps are performed after a step of storing said first and second vectors of responses.

56. A system for the generation of a double-evoking stimulus signal in an ear canal and the measurement of a double-evoked set of iso-level transfer functions of the ear, the system comprising:

a stimulus signal generator operative to generate a double-evoking stimulus set comprising a first electrical stimulus signal $s_1(t)$ having a first arbitrary waveform, followed by a second electrical stimulus signal $s_2(t)$ having a second arbitrary waveform of the same duration as $s_1(t)$, and followed by a third electrical stimulus signal that is the superposition of $s_1(t)$ and $S_2(t)$;

a probe assembly positionable in operative relation to an ear having an ear canal;

an acoustic source transducer within said probe assembly and coupled to said signal generator to emit into the ear a double-evoking acoustic stimulus set in response to said double-evoking stimulus set, thereby to stimulate in the ear canal a double-evoked acoustic response set including first, second and third acoustic pressure signals, an acoustic pressure transducer within said probe assembly and operative to detect and convert said double-evoked acoustic response set to a double-evoked electrical response set including first, second and third electrical response signals corresponding to said first, second and third acoustic pressure signals, a computer processor operative to receive said double-evoked electrical response set and calculate a double-evoked set of iso-level transfer functions of the ear comprised of first, second and third iso-level transfer functions, said computer processor operative to determine said first iso-level transfer function based on said first electrical response signal, and a given representation of the equivalent circuit parameters of said acoustic source transducer and said acoustic pressure transducer, and said computer processor operative to determine said second iso-level transfer function based on said second electrical response signal, and a given representation of the equivalent circuit parameters of said acoustic source transducer and said acoustic pressure transducer, and said computer processor operative to determine said third iso-level transfer function based on said third electrical response signal, and a given representation of the equivalent circuit parameters of said acoustic source and said acoustic pressure transducer, said double-evoked set of iso-level transferfunction of the ear being indicative of the nonlinear acoustic response of the ear.

57. The system of claim 56 wherein said computer processor is operative to determine a nonlinear transfer function of the ear based on said double-evoked set of iso-level transfer functions of the ear, and said given representation of the equivalent circuit parameters of said acoustic source transducer and said acoustic pressure transducer.

58. The system of claim 56 wherein said iso-level transfer functions of the ear comprise time-domain iso-level functions of the ear.

59. The system of claim 56 wherein said time-domain iso-level transfer functions of the ear comprise a selected one of a set including a reflection function, a time-domain impedance function and a time-domain admittance function.

60. The system of claim 56 wherein said iso-level transfer functions of the ear comprise frequency-domain iso-level functions of the ear.

61. The system of claim 60 wherein said frequency-domain iso-level transfer functions comprise a selected one of a set including a reflection coefficient function, an impedance function, and an admittance function.

62. The system of claim 56 wherein said given representations of the equivalent circuit parameters of said acoustic source transducer and said acoustic pressure transducer are stored representations of the equivalent circuit parameters of said acoustic source transducer and said acoustic pressure transducer in said computer processor.

63. The system of claim 56 wherein said computer processor determines power absorbed by the ear based on said double-evoked set of iso-level transfer functions of the ear, said double-evoked electrical response set, and said given representation of the equivalent circuit parameters of said acoustic source transducer and said acoustic pressure transducer.

64. The system of claim 56 wherein said computer processor determines differential nonlinear power absorbed by the ear based on said double-evoked set of iso-level transfer functions of the ear, said double-evoked electrical response set, and said given representation of the equivalent circuit parameters of said acoustic source and said acoustic pressure transducer.

65. The system of claim 56 further comprising a pump coupled to said probe assembly to control static pressure in the ear, said computer processor determining a double-evoked set of iso-level transfer functions of the ear at an arbitrary value of static pressure in the ear.

66. The system of claim 57 further comprising a pump coupled to said probe assembly to control static pressure in the ear, said computer processor determining a nonlinear transfer function of the ear and at an arbitrary value of static pressure in the ear.

67. The system of claim 56 wherein said first and second stimulus signals are first and second click signals.

68. The system of claim 56 wherein said first and second stimulus signals are first and second chirp signals.

69. The system of claim 62 wherein said second arbitrary waveform is substantially identical to said first arbitrary waveform except that it is delayed in time and scaled in amplitude.

70. The system of claim 69 wherein said delay time ranges from 0 to 10 milliseconds.

71. The system of claim 62 wherein said first and second waveforms are identical.

72. The system of claim 56 wherein said computer processor determines a double-evoked otoacoustic reflected pressure response of the ear based on said double-evoked set of iso-level transfer functions of the ear, and said given representation of the equivalent circuit parameters of said acoustic source and said acoustic pressure transducer.

73. The system of claim 56 further comprising:

a set of one or more acoustic calibration waveguides, each having predetermined dimensions and having first end open and second end terminated in a specified manner;

said probe assembly positioned in each of one or more acoustic calibration waveguides to stimulate in each of said set of one or more acoustic calibration waveguides a corresponding set of one or more double-evoked acoustic calibration responses, each double-evoked acoustic calibration response including first, second and third acoustic calibration pressure signals in response to the output of said acoustic source transducer, the input of which is said double-evoking stimulus set, said probe assembly positioned in each of said set of one or more acoustic calibration waveguides including said acoustic pressure transducer operative to detect and convert each of said set of one or more double-evoked acoustic calibration responses to each of a set of one or more double-evoked electrical calibration response signals, each double-evoked electrical calibration response signal including first, second and third electrical calibration response signals corresponding to said set of first, second and third acoustic calibration pressure signals in each of said set of one or more double-evoked acoustic calibration responses, a computer processor containing a calibration waveguide model indicative of an acoustic transfer characteristic for each of said set of one or more acoustic calibration waveguides, and receiving said set of one or more double-evoked electrical calibration response signals, said computer processor determining said given representation of the equivalent circuit parameters of said acoustic source and said acoustic pressure transducer.

74. The system of claim 73 in which each of said set of one or more acoustic calibration waveguides is a cylindrical tube with said second end closed.

75. The system of claim 73 in which said calibration waveguide model incorporates viscothermal losses in each of said set of one or more acoustic waveguides.

76. A system for the generation of a double-evoking acoustic signal in an ear canal and the measurement of a double-evoked set of iso-level transfer functions of the ear, the system comprising, a stimulus signal generator operative to simultaneously generate two stimulus sets:
  a first double-evoking stimulus set comprising a first electrical stimulus signal $s_1(t)$ having a first arbitrary waveform, a second electrical stimulus signal of zero amplitude over the same duration as $s_1(t)$, and a third electrical stimulus signal $s_1(t)$, and
  a second double-evoking stimulus set comprising a fourth electrical stimulus signal of zero amplitude over the same duration as $s_1(t)$, a fifth electrical stimulus signal $s_2(t)$ having a second arbitrary waveform over the same duration as $s_1(t)$, and a sixth electrical stimulus signal $s_2(t)$, a probe assembly positionable in operative relation to an ear having an ear canal, first and second acoustic source transducers within said probe assembly coupled to said signal generator to simultaneously emit into the ear first and second double-evoking acoustic stimulus sets in response to said first and second double-evoking stimulus sets respectively, thereby to stimulate in the ear canal a double-evoked acoustic response set including first, second and third acoustic pressure signals corresponding in duration to said first, second and third electrical stimulus signals, respectively, an acoustic pressure transducer within said probe assembly and operative to detect and convert said double-evoked acoustic response set to a double-evoked electrical response set including first, second and third electrical response signals corresponding to said first, second and third acoustic pressure signals, a computer processor operative to receive said double-evoked electrical response set and calculate a double-evoked set of iso-level transfer functions of the ear comprised of first, second and third iso-level transfer functions, said computer processor operative to determine said first iso-level transfer function based on said first electrical response signal, and a given representation of the equivalent circuit parameters of said first acoustic source transducer and said acoustic pressure transducer, and said computer processor operative to determine said second iso-level transfer function based on said second electrical response signal, and a given representation of the equivalent circuit parameters of said second acoustic source transducer and said acoustic pressure transducer, and said computer processor operative to determine said third iso-level transfer function based on said third electrical response signal, and a given representation of the equivalent circuit parameters of said first and second acoustic source and said acoustic pressure transducer, said double-evoked set of iso-level transfer functions of the ear being indicative of the nonlinear acoustic response of the ear.

77. The system of claim 76 wherein said computer processor is operative to determine a nonlinear transfer function of the ear based on said double-evoked set of iso-level transfer functions of the ear, and said given representation of the equivalent circuit parameters of said first and second acoustic source transducers and said acoustic pressure transducer.

78. The system of claim 76 wherein said given representations of the equivalent circuit parameters of said first and second acoustic source transducers and said acoustic pressure transducer are stored representations of the equivalent circuit parameters of said first and second acoustic source transducers and said acoustic pressure transducer in said computer processor.

79. The system of claim 76 wherein said computer processor determines power absorbed by the ear based on said double-evoked set of iso-level transfer functions of the ear, said double-evoked electrical response set, and said given representation of the equivalent circuit parameters of said first and second acoustic source transducers and said acoustic pressure transducer.

80. The system of claim 76 wherein said computer processor determines differential nonlinear power absorbed by the ear based on said double-evoked set of iso-level transfer functions of the ear, said double-evoked electrical response set, and said given representation of the equivalent circuit parameters of said first and second acoustic source trandducers and said acoustic pressure transducer.

81. The system of claim 76 further comprising a pump coupled to said probe assembly to control static pressure in the ear, said computer processor determining a double-evoked set of iso-level transfer functions of the ear at an arbitrary value of static pressure in the ear.

82. The system of claim 76 wherein said second arbitrary waveform is substantially identical to said first arbitrary waveform except that it is delayed in time and scaled in amplitude.

83. The system of claim 77 wherein said first and second arbitrary waveforms are first and second click signals.

84. The system of claim 82 wherein said first and second stimulus signals are first and second chirp signals.

85. The system of claim 82 wherein said delay time ranges from 0 to 10 milliseconds.

86. The system of claim 76 wherein said first and second waveforms are identical.

87. The system of claim 76 wherein said computer processor determines a double-evoked otoacoustic reflected pressure response of the ear based on said double-evoked set of iso-level transfer functions of the ear, and said given representation of the equivalent circuit parameters of said first and second acoustic source transducers and said acoustic pressure transducer.

88. The system of claim 76 wherein said iso-level transfer functions of the ear comprise time-domain iso-level functions of the ear.

89. The system of claim 88 wherein said time-domain iso-level transfer functions of the ear comprise a selected one of a set including a reflection function, a time-domain impedance function and a time-domain admittance function.

90. The system of claim 76 wherein said iso-level transfer functions of the ear comprise frequency-domain iso-level functions of the ear.

91. The system of claim 90 wherein said frequency-domain iso-level transfer functions all comprise a selected one of a set including a reflection coefficient function, an impedance function, and an admittance function.

92. The system of claim 76 further comprising:
  a set of one or more acoustic calibration waveguides, each having predetermined dimensions and having first end open and second end terminated in a specified manner;

said probe assembly positioned in said first end of each of one or more acoustic calibration waveguides to stimulate in each of said set of one or more acoustic calibration waveguides a corresponding set of one or more double-evoked acoustic calibration responses, each double-evoked acoustic calibration response including first, second and third acoustic calibration pressure signals in response to the output of said first acoustic source transducer, the input of which is said first double-evoking stimulus set, and the output of said second acoustic source transducer, the input of which is said second double-evoking stimulus set, said probe assembly positioned in each of said set of one or more acoustic calibration waveguides including said acoustic pressure transducer operative to detect and convert each of said set of one or more double-evoked acoustic calibration responses to each of a set of one or more double-evoked electrical calibration response signals, each double-evoked electrical calibration response signal including first, second and third electrical calibration response signals corresponding to said set of first, second and third acoustic calibration pressure signals in each of said set of one or more double-evoked acoustic calibration responses, a computer processor containing a calibration waveguide model indicative of an acoustic transfer characteristic for each of said set of one or more acoustic calibration waveguides, and receiving said set of one or more double-evoked electrical calibration response signals, said computer processor determining said given representation of the equivalent circuit parameters of said first and second acoustic sources and said acoustic pressure transducer, said double-evoked set of iso-level transfer functions of the ear being indicative of the nonlinear acoustic response of the ear.

93. The system of claim 92 in which each of said one or more acoustic calibration waveguides is a cylindrical tube with said second end closed.

94. The system of claim 76 in which said calibration waveguide model incorporates viscothermal losses in the acoustic transfer characteristics of each of said set of one or more acoustic waveguides.

95. A method for generating an evoked otoacoustic emission stimulus signal in an ear canal and measuring the evoked otoacoustic emission while controlling for nonlinearities and being free of time-gating, comprising, generating a first stimulus signal having a first arbitrary waveform and a second stimulus signal having a second arbitrary waveform, said first and second stimulus signals forming a double-evoking three stimulus set comprising the first stimulus signal, the second stimulus signal, and a superposition combination of the first and second stimulus signals, providing a probe assembly operative to receive the first and second stimulus signals and to transduce the first and second stimulus signals into first and second acoustic signals, inserting said probe assembly into an ear having an ear canal, thereby stimulating in the ear canal an evoked otoacoustic emission in the form of detected acoustic pressure, detecting said detected acoustic pressure and transducing said detected acoustic pressure to detected electrical signals corresponding to the detected acoustic pressure, said detecting step comprising detecting an acoustic three stimulus response set from the ear in response to the three stimulus set and generating an electrical three stimulus response signal corresponding to the acoustic three stimulus response set, processing said electrical three stimulus response signal and thereby determining an evoked cochlear response to the acoustic three stimulus response set, said electrical three stimulus response signal including a linear portion and a nonlinear portion corresponding to the evoked otoacoustic emission and said processing step including subtracting the electrical response signal corresponding to the first stimulus signal and the electrical response signal corresponding to the second stimulus from the electrical response signal corresponding to the useful superposition combination of the first and second stimulus signals to substantially eliminate the linear portion.

96. The system of claim 17 in which the first and second stimulus signals are first and second sinusoid signals, respectively, the first sinusoid signal having a first amplitude, first frequency and first phase, and the second sinusoid signal having a second amplitude, second frequency and second phase, and the first and second amplitudes, first and second frequencies, and first and second phases each having a predetermined relationship with one another.

97. The system of claim 96 in which said second frequency of said second sinusoid signal is identical to said first frequency of said first sinusoid signal.

98. The system of claim 17 in which the first stimulus signal is a first tone burst created using a windowed first sinusoid and the second stimulus signal is selected from the group consisting of a second tone burst created using a windowed second sinusoid and a second sinusoid signal, the first stimulus signal having a first amplitude, first frequency and first predetermined phase, and the second stimulus signal having a second amplitude, second frequency, and second predetermined phase, and the first and second amplitudes, first and second frequencies, and first and second phases each having a predetermined relationship.

99. The system of claim 98 in which the first stimulus signal is a first tone burst created using a windowed first sinusoid and the second stimulus signal is a second tone burst created using a windowed second sinusoid, the first sinusoid having a first amplitude, frequency and first predetermined phase, and the second sinusoid having a second amplitude, frequency and second predetermined phase, and the first and second amplitudes, and the first and second phases each having a predetermined relationship, and the frequencies of the first and second sinusoids being identical.

100. The system of claim 17 in which said double-evoked otoacoustic emission is analyzed using time-frequency analysis to obtain a double-evoked otoacoustic emission time-frequency representation.

101. The system of claim 17 in which said double-evoked otoacoustic emission is analyzed using wavelet analysis to obtain a double-evoked otoacoustic emission wavelet representation.

* * * * *

UNITED STATES PATENT AND TRADEMARK OFFICE
CERTIFICATE OF CORRECTION

PATENT NO. : 5,792,073
DATED : August 11, 1998
INVENTOR(S) : Douglas H. Keefe

It is certified that error appears in the above-identified patent and that said Letters Patent is hereby corrected as shown below:

Title page,
Item [75], Inventor, add -- Robert Ling, Mercer Island, Wash. --

Signed and Sealed this

Twenty-first Day of September, 2004

JON W. DUDAS
*Director of the United States Patent and Trademark Office*